US009301756B2

(12) United States Patent
Wardle

(10) Patent No.: US 9,301,756 B2
(45) Date of Patent: Apr. 5, 2016

(54) SURGICAL COILS AND METHODS OF DEPLOYING

(76) Inventor: John L. Wardle, San Clemente, CA (US)

( * ) Notice: Subject to any disclaimer, the term of this patent is extended or adjusted under 35 U.S.C. 154(b) by 259 days.

(21) Appl. No.: 13/356,501

(22) Filed: Jan. 23, 2012

(65) Prior Publication Data
US 2012/0123469 A1 May 17, 2012

Related U.S. Application Data

(62) Division of application No. 12/109,291, filed on Apr. 24, 2008, now Pat. No. 8,128,641, which is a division of application No. 10/386,260, filed on Mar. 10, 2003, now abandoned.

(60) Provisional application No. 60/363,106, filed on Mar. 11, 2002.

(51) Int. Cl.
A61B 17/00 (2006.01)
A61B 5/00 (2006.01)
A61B 17/068 (2006.01)
(Continued)

(52) U.S. Cl.
CPC ............ *A61B 17/068* (2013.01); *A61B 17/0644* (2013.01); *A61B 17/06109* (2013.01); *A61B 17/072* (2013.01); *A61B 10/0275* (2013.01); *A61B 2017/00867* (2013.01); *A61B 2017/0409* (2013.01); *A61B 2017/0414* (2013.01); *A61B 2017/0416* (2013.01); *A61B 2017/0443* (2013.01); *A61B 2017/061* (2013.01); *A61B 2017/0649* (2013.01); *A61B 2017/0688* (2013.01); *A61B 2017/22061* (2013.01); *A61B 2019/5408* (2013.01); *A61B 2019/5416* (2013.01); *A61B 2019/5483* (2013.01); *A61B 2019/5487* (2013.01); *A61F 2/07* (2013.01); *A61F 2/2409* (2013.01); *A61F 2002/065* (2013.01)

(58) Field of Classification Search
USPC ......... 606/142, 144, 151, 153, 232, 116, 156; 600/431, 562; 128/899, 897
See application file for complete search history.

(56) References Cited

U.S. PATENT DOCUMENTS 4,548,202 A 10/1985 Duncan
4,616,656 A 10/1986 Nicholson et al.
(Continued)

FOREIGN PATENT DOCUMENTS

WO WO 03/077730 9/2003

OTHER PUBLICATIONS

International Search Report mailed on Oct. 1, 2003 in International Application No. PCT/US2003/07608 filed on: Mar. 11, 2003 and published as WO 03/077730 on Sep. 1, 2003.
(Continued)

Primary Examiner — Tuan V Nguyen
(74) Attorney, Agent, or Firm — Anderson IP, Inc.

(57) ABSTRACT

Surgical coils are disclosed for marking, anchoring, stapling and suturing. Such surgical coils may be implanted in the body by deforming them to a small cross section profile, sliding them through a low profile delivery device then deploying them from an embodiment of a delivery device at a targeted site. Embodiments of surgical coils when deployed revert back to a coiled configuration and circle tissue at the target site. Such surgical coils may be deployed about attachment members, such as suture lines, marker lines and the like for anchoring same.

11 Claims, 46 Drawing Sheets

(51) Int. Cl.
*A61B 17/06* (2006.01)
*A61B 17/064* (2006.01)
*A61B 17/072* (2006.01)
A61B 10/02 (2006.01)
A61B 17/04 (2006.01)
A61B 17/22 (2006.01)
A61B 19/00 (2006.01)
A61F 2/07 (2013.01)
A61F 2/24 (2006.01)
A61F 2/06 (2013.01)

(56) References Cited

U.S. PATENT DOCUMENTS

| | | | |
|---|---|---|---|
| 4,632,100 A | 12/1986 | Somers et al. | |
| 4,774,948 A | 10/1988 | Markham | |
| 4,843,651 A | 7/1989 | Gramza et al. | |
| 4,883,070 A | 11/1989 | Hanson | |
| 4,899,744 A | 2/1990 | Fujitsuka et al. | |
| 4,924,865 A | 5/1990 | Bays et al. | |
| 4,931,059 A | 6/1990 | Markham | |
| 4,935,027 A | 6/1990 | Yoon | |
| 4,938,760 A | 7/1990 | Burton et al. | |
| 5,002,548 A | 3/1991 | Campbell et al. | |
| 5,007,921 A | 4/1991 | Brown | |
| 5,013,316 A | 5/1991 | Goble et al. | |
| 5,018,530 A | 5/1991 | Rank et al. | |
| 5,030,224 A | 7/1991 | Wright et al. | |
| 5,104,399 A | 4/1992 | Lezarus | |
| 5,123,906 A | 6/1992 | Kelman | |
| 5,127,916 A | 7/1992 | Spencer et al. | |
| 5,129,906 A | 7/1992 | Ross et al. | |
| 5,141,520 A | 8/1992 | Goble et al. | |
| 5,179,962 A | 1/1993 | Dutcher et al. | |
| 5,186,922 A | 2/1993 | Shell et al. | |
| 5,219,358 A | 6/1993 | Bendel et al. | |
| 5,221,269 A | 6/1993 | Miller et al. | |
| 5,231,989 A | 8/1993 | Middleman et al. | |
| 5,486,183 A | 1/1996 | Middleman et al. | |
| 5,486,187 A * | 1/1996 | Schenck | 606/153 |
| 5,489,295 A | 2/1996 | Piplani et al. | |
| 5,522,820 A | 6/1996 | Caspari et al. | |
| 5,527,323 A | 6/1996 | Jervis et al. | |
| 5,556,410 A | 9/1996 | Mittermeir et al. | |
| 5,571,117 A | 11/1996 | Ahn | |
| 5,571,285 A | 11/1996 | Chow et al. | |
| 5,573,543 A | 11/1996 | Akopov et al. | |
| 5,597,378 A | 1/1997 | Jervis | |
| 5,601,572 A * | 2/1997 | Middleman et al. | 606/139 |
| 5,628,783 A | 5/1997 | Quiachon et al. | |
| 5,645,567 A | 7/1997 | Crainich | |
| 5,662,683 A | 9/1997 | Kay | |
| 5,693,083 A | 12/1997 | Baker et al. | |
| 5,738,474 A | 4/1998 | Blewett | |
| 5,810,851 A * | 9/1998 | Yoon | 606/148 |
| 5,816,258 A | 10/1998 | Jervis | |
| 5,853,366 A | 12/1998 | Dowlatshahi | |
| 5,902,310 A | 5/1999 | Foerster et al. | |
| 6,042,607 A | 3/2000 | Williamson, IV et al. | |
| 6,165,183 A | 12/2000 | Kuehn et al. | |
| 6,168,598 B1 | 1/2001 | Martello | |
| 6,171,338 B1 | 1/2001 | Talja et al. | |
| 6,188,932 B1 | 2/2001 | Lindegren | |
| 6,220,248 B1 | 4/2001 | Voegele et al. | |
| 6,228,055 B1 | 5/2001 | Foerster et al. | |
| 6,234,177 B1 | 5/2001 | Barsch | |
| 6,235,051 B1 | 5/2001 | Murphy | |
| 6,256,543 B1 | 7/2001 | Spence et al. | |
| 6,261,243 B1 | 7/2001 | Burney et al. | |
| 6,261,302 B1 | 7/2001 | Voegele et al. | |
| 6,270,464 B1 | 8/2001 | Fulton, III et al. | |
| 6,287,339 B1 | 9/2001 | Vazquez et al. | |
| 6,312,429 B1 | 11/2001 | Burbank et al. | |
| 6,312,447 B1 | 11/2001 | Grimes | |
| 6,325,816 B1 | 12/2001 | Fulton, III et al. | |
| 6,332,864 B1 | 12/2001 | Schweich, Jr. et al. | |
| 6,332,893 B1 | 12/2001 | Mortier et al. | |
| 6,413,274 B1 | 7/2002 | Pedros | |
| 6,432,064 B1 | 8/2002 | Hibner et al. | |
| 6,447,523 B1 | 9/2002 | Middleman et al. | |
| 6,508,829 B1 | 1/2003 | Levinson et al. | |
| 6,514,263 B1 | 2/2003 | Stefanchik et al. | |
| 6,520,974 B2 | 2/2003 | Tanner et al. | |
| 6,520,980 B1 | 2/2003 | Foerster | |
| 6,564,806 B1 | 5/2003 | Fogarty et al. | |
| 6,607,541 B1 | 8/2003 | Gardiner et al. | |
| 6,682,540 B1 * | 1/2004 | Sancoff et al. | 606/153 |
| 6,709,442 B2 * | 3/2004 | Miller et al. | 606/153 |
| 6,752,154 B2 | 6/2004 | Fogarty et al. | |
| 6,766,186 B1 | 7/2004 | Hoyns et al. | |
| 6,802,847 B1 * | 10/2004 | Carson et al. | 606/153 |
| 6,981,983 B1 | 1/2006 | Rosenblatt et al. | |
| 7,731,705 B2 | 6/2010 | Wardle | |
| 7,959,648 B2 | 6/2011 | Mas | |
| 8,128,641 B2 | 3/2012 | Wardle | |
| 8,287,553 B2 | 10/2012 | Wardle | |
| 8,608,725 B2 | 12/2013 | Wardle | |
| 2003/0225420 A1 | 12/2003 | Wardle | |
| 2004/0034357 A1 | 2/2004 | Beane et al. | |
| 2004/0193151 A1 | 9/2004 | To et al. | |
| 2005/0163821 A1 | 7/2005 | Sung | |
| 2005/0182390 A1 | 8/2005 | Shanley | |
| 2006/0151460 A1 | 7/2006 | Wardle | |
| 2008/0195146 A1 | 8/2008 | Wardle | |
| 2010/0204709 A1 | 8/2010 | Wardle | |
| 2012/0123469 A1 | 5/2012 | Wardle | |
| 2013/0006201 A1 | 1/2013 | Wardle | |

OTHER PUBLICATIONS

Office Action mailed on: Jan. 25, 2008 in U.S. Appl. No. 10/386,260, filed Mar. 10, 2003 and published as: US-2006-0151460 on: Jul. 13, 2006.

Office Action mailed on: Sep. 26, 2007 in U.S. Appl. No. 10/386,260, filed Mar. 10, 2003 and published as: US-2006-0151460 on: Jul. 13, 2006.

Office Action mailed on: May 8, 2007 in U.S. Appl. No. 10/386,260, filed Mar. 10, 2003 and published as: US-2006-0151460 on: Jul. 13, 2006.

Office Action mailed on: Apr. 17, 2006 in U.S. Appl. No. 10/386,260, filed Mar. 10, 2003 and published as: US-2006-0151460 on: Jul. 13, 2006.

Office Action mailed on: Nov. 3, 2011 in U.S. Appl. No. 12/109,291, filed Apr. 24, 2008 and published as: US-2008/0195146 on: Aug. 14, 2008, now issued as: U.S. Pat. No. 8,128,641 on Mar. 6, 2012.

Office Action mailed on: Dec. 22, 2010 in U.S. Appl. No. 12/109,291, filed Apr. 24, 2008 and published as: US-2008/0195146 on: Aug. 14, 2008, now issued as: U.S. Pat. No. 8,128,641 on Mar. 6, 2012.

Office Action mailed on: Aug. 25, 2010 in U.S. Appl. No. 12/109,291, filed Apr. 24, 2008 and published as: US-2008/0195146 on: Aug. 14, 2008, now issued as: U.S. Pat. No. 8,128,641 on Mar. 6, 2012.

Office Action mailed on: Feb. 19, 2010 in U.S. Appl. No. 11/328,884, filed Jan. 9, 2006 and published as: US-2006-0151460 on: Jul. 13, 2006, and issued as: U.S. Pat. No. 7,731,705 on Jun. 8, 2010.

Office Action mailed on: Aug. 5, 2009 in U.S. Appl. No. 11/328,884, filed Jan. 9, 2006 and published as: US-2006-0151460 on: Jul. 13, 2006, and issued as: U.S. Pat. No. 7,731,705 on Jun. 8, 2010.

Office Action mailed on: Jul. 2, 2012 in U.S. Appl. No. 12/765,743, filed Apr. 22, 2010 and published as: US-2010/0204709 on: Aug. 12, 2010.

Office Action mailed on: Mar. 29, 2012 in U.S. Appl. No. 12/765,743, filed Apr. 22, 2010 and published as: US-2010/0204709 on: Aug. 12, 2010.

Office Action mailed on: Dec. 27, 2011 in U.S. Appl. No. 12/765,743, filed Apr. 22, 2010 and published as: US-2010/0204709 on: Aug. 12, 2010.

(56) References Cited

OTHER PUBLICATIONS

Office Action mailed on: Mar. 30, 2011 in U.S. Appl. No. 12/765,743, filed Apr. 22, 2010 and published as: US-2010/0204709 on: Aug. 12, 2010.

Office Action mailed on: Apr. 2, 2013 in U.S. Appl. No. 13/610,733, filed Sep. 11, 2012 and published as: US-2013/0006201 on: Jan. 3, 2013.

Office Action mailed on: Aug. 20, 2013 in U.S. Appl. No. 13/610,733, filed Sep. 11, 2012 and published as: US-2013/0006201 on: Jan. 3, 2013.

* cited by examiner

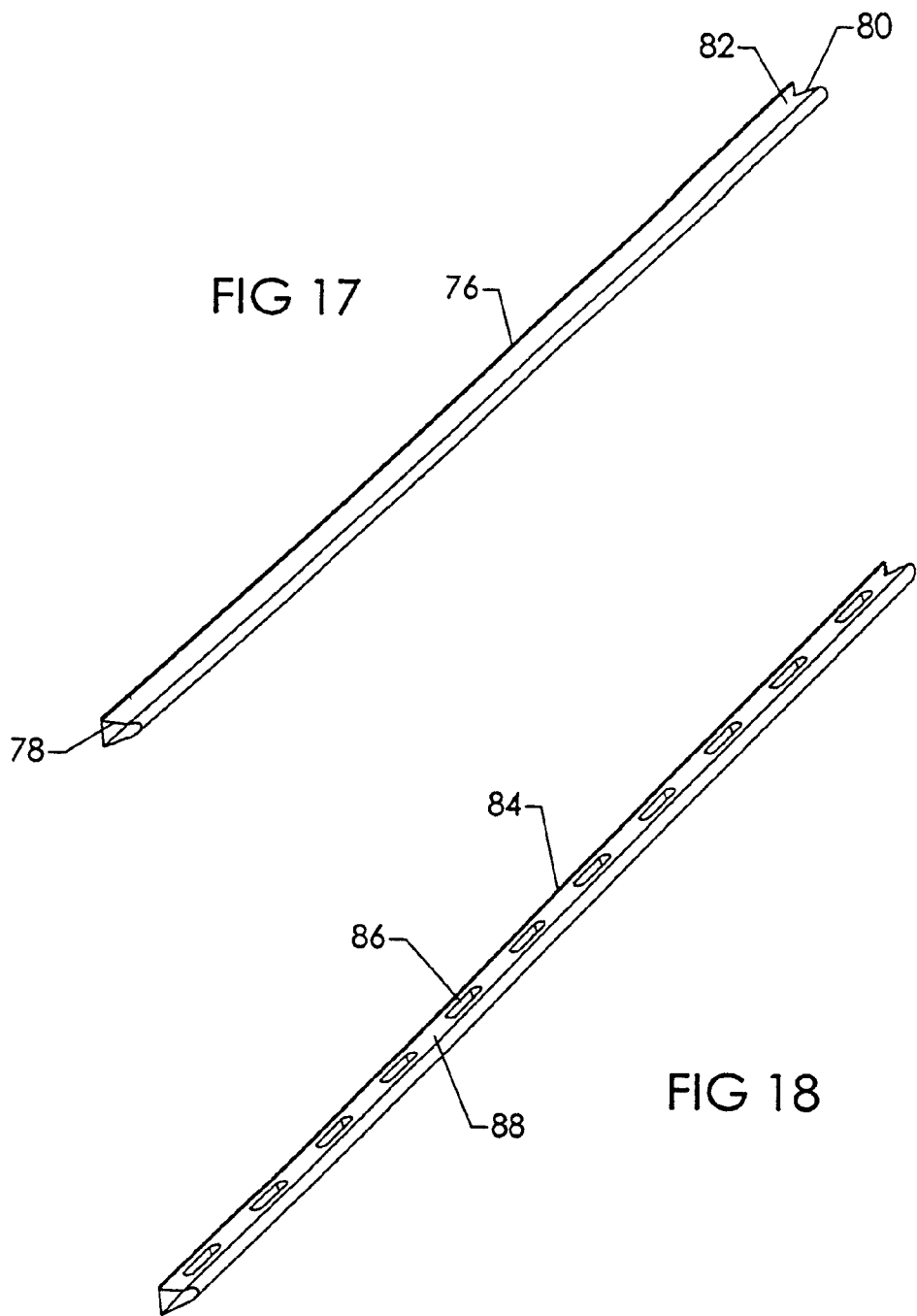

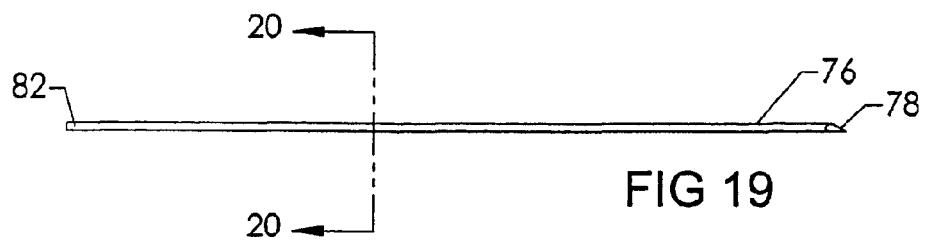
FIG 19
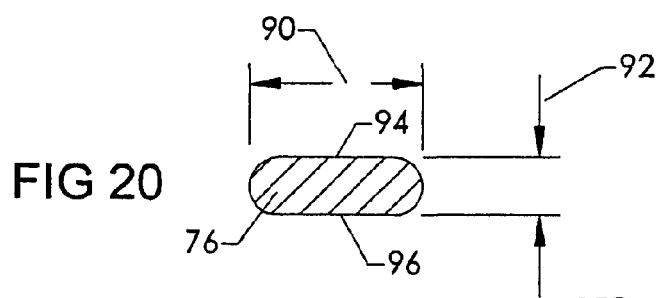
FIG 20
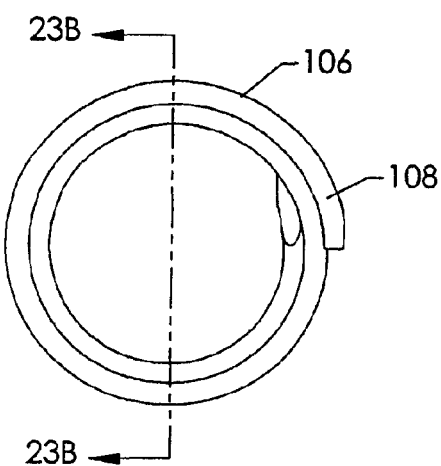
FIG 21
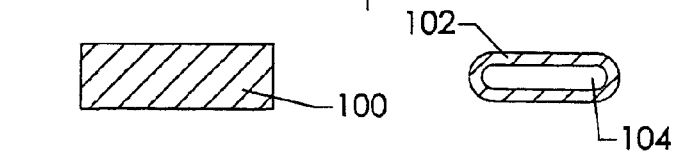
FIG 22
FIG 23
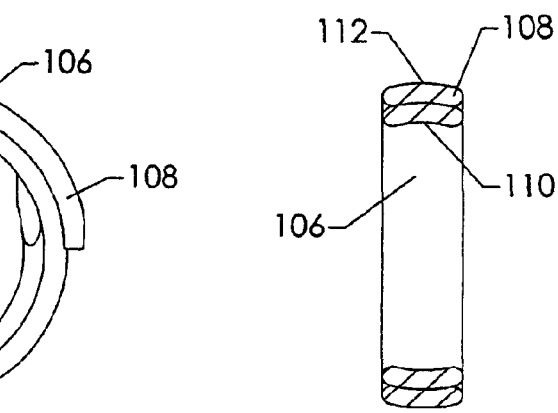
FIG 23A
FIG 23B

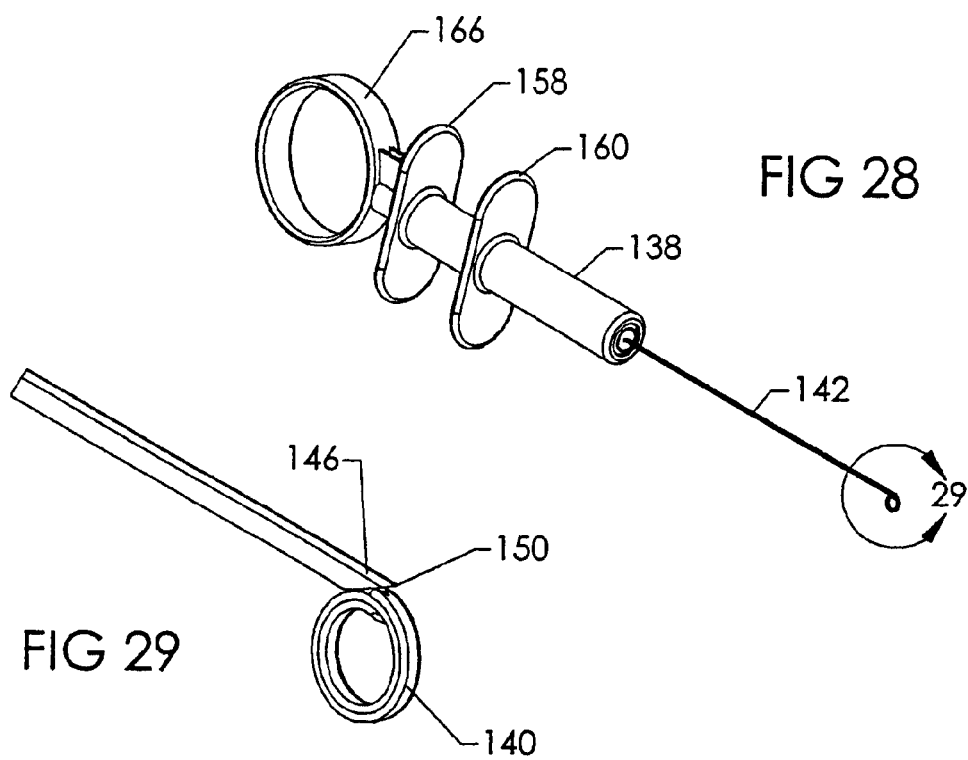
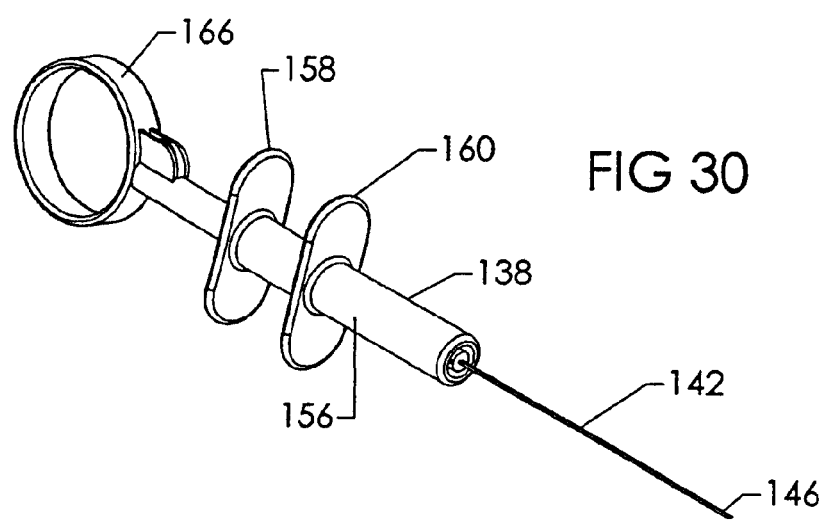

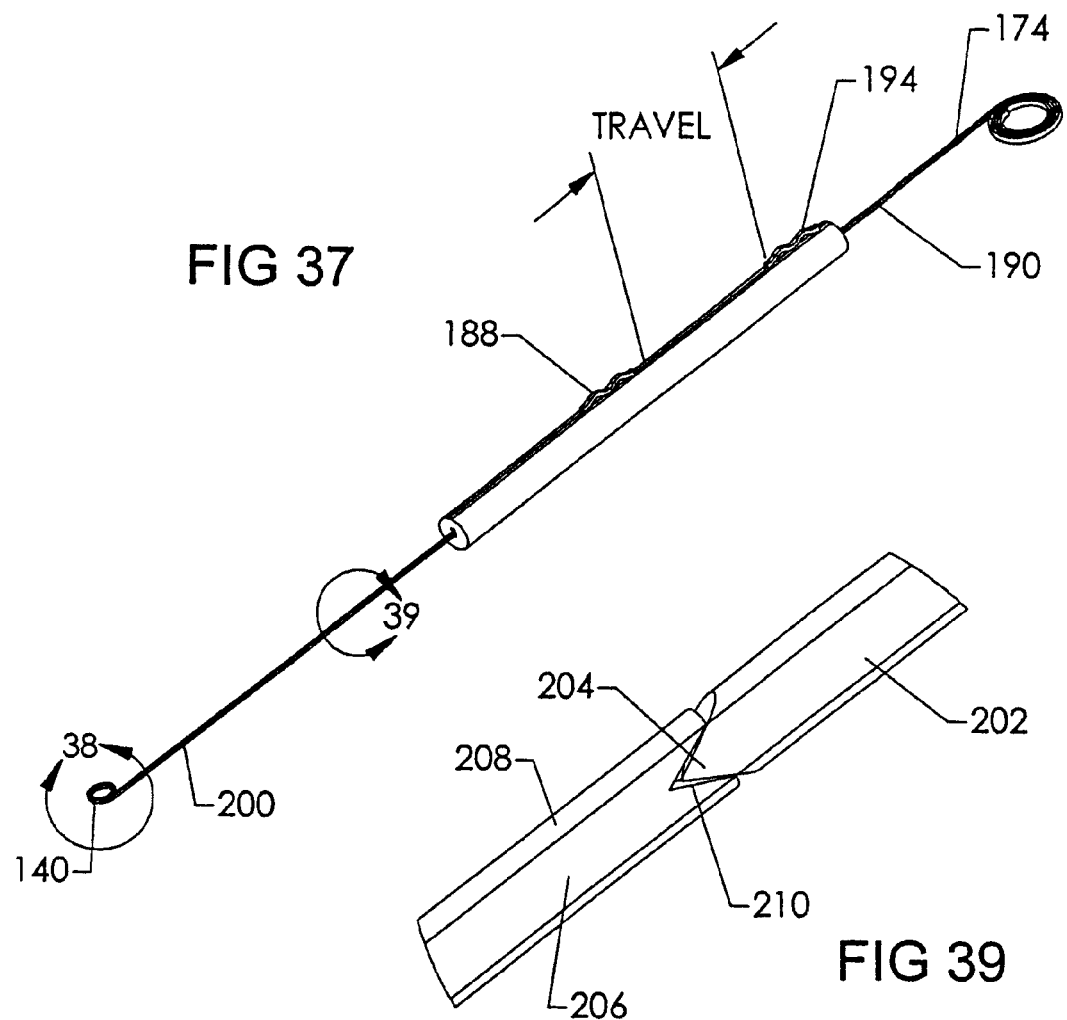
FIG 37
FIG 39
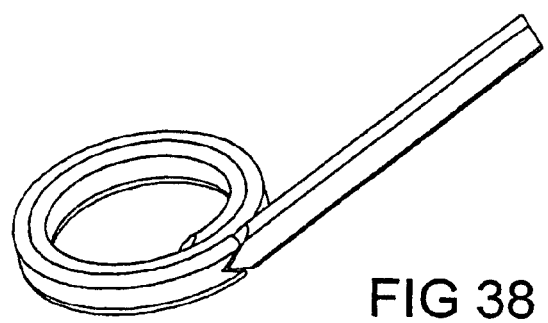
FIG 38

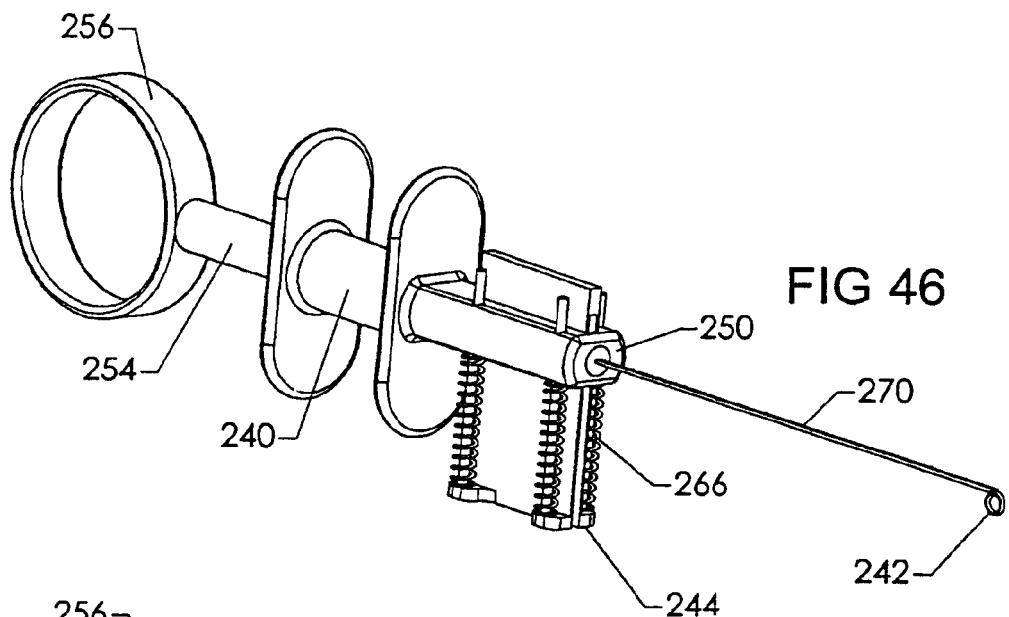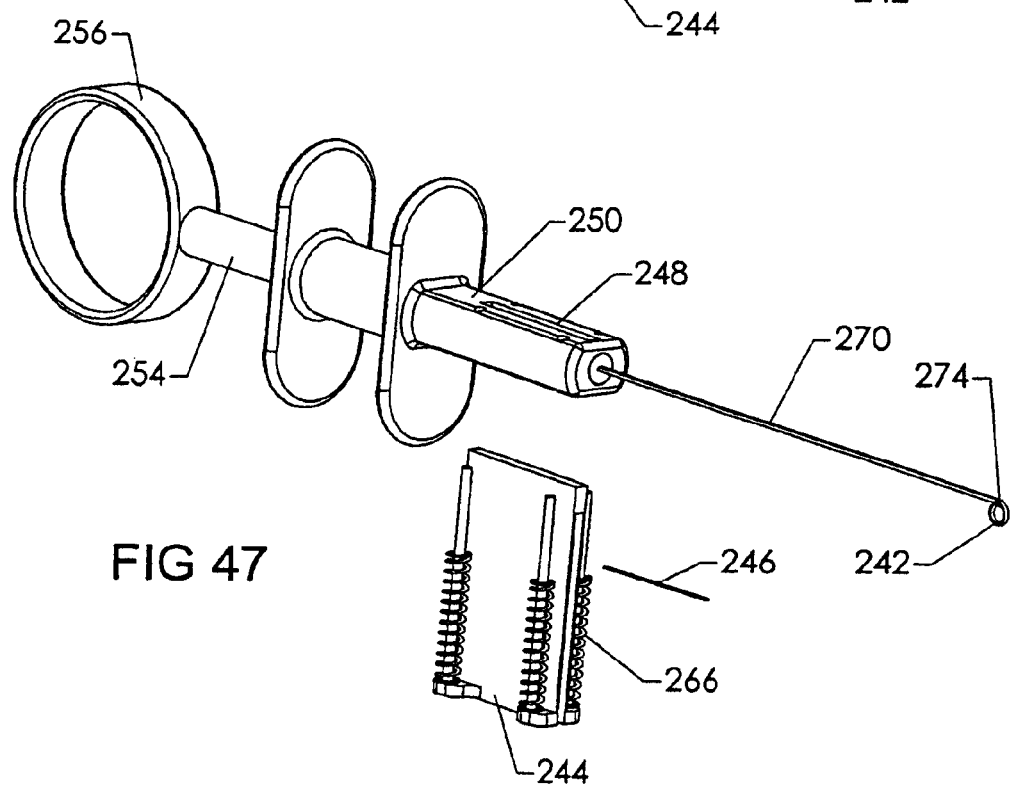

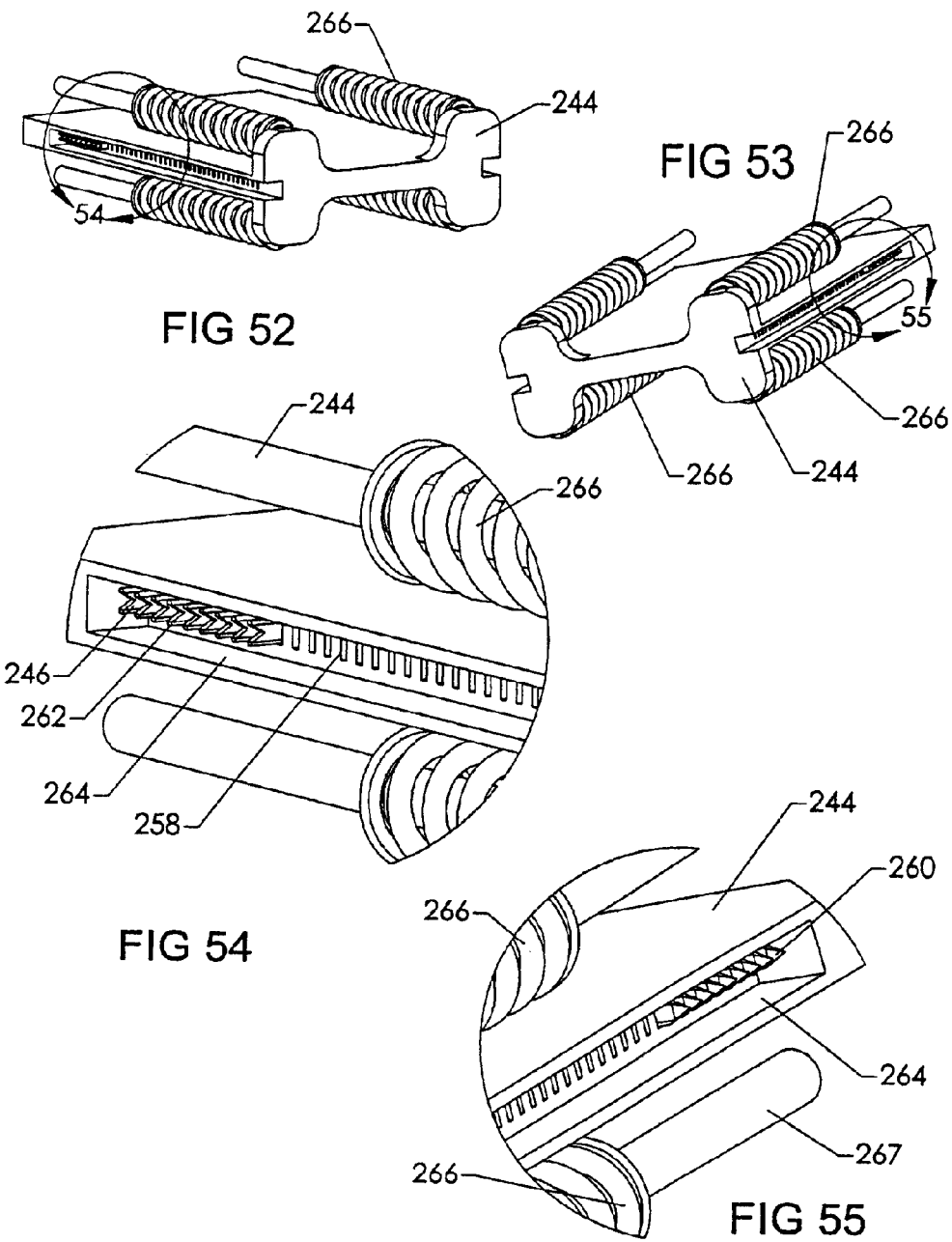

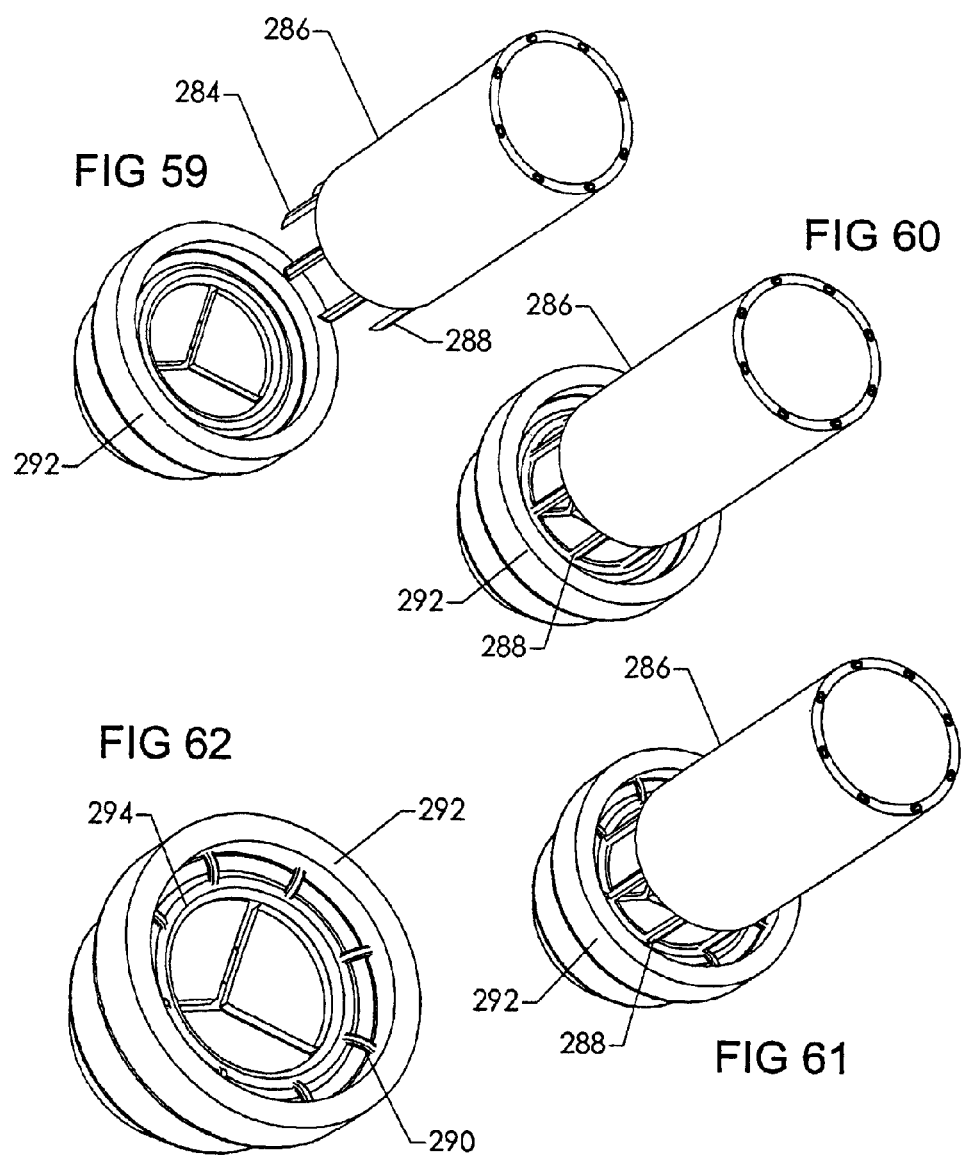

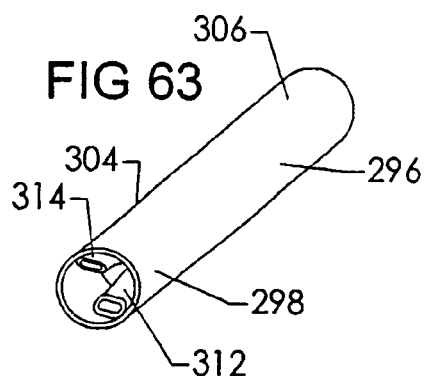
FIG 63
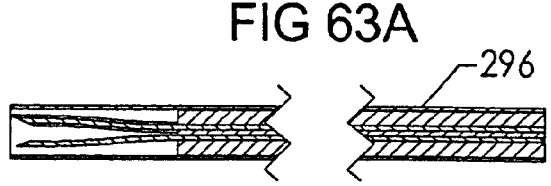
FIG 63A
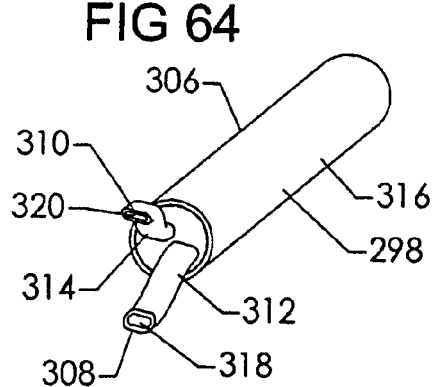
FIG 64
FIG 64A
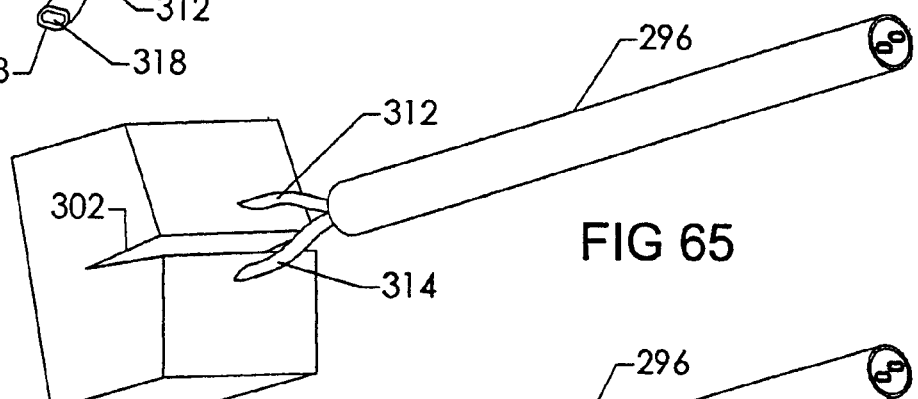
FIG 65
FIG 66

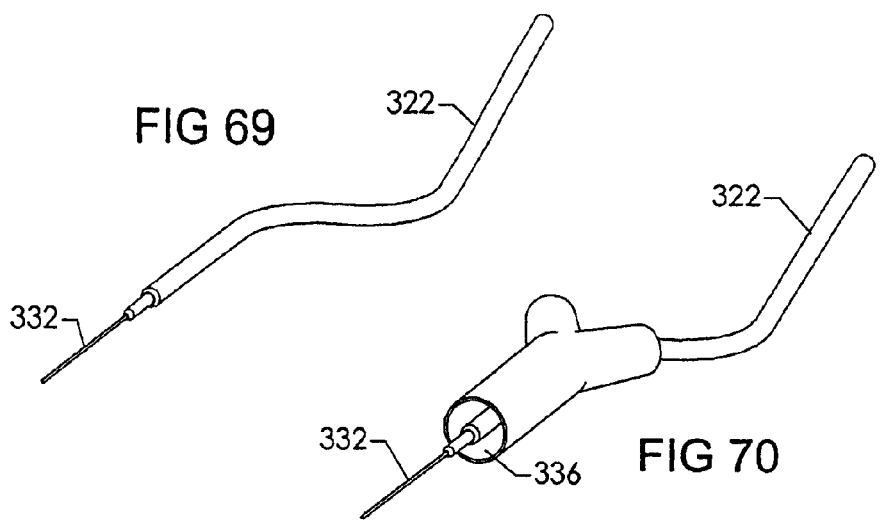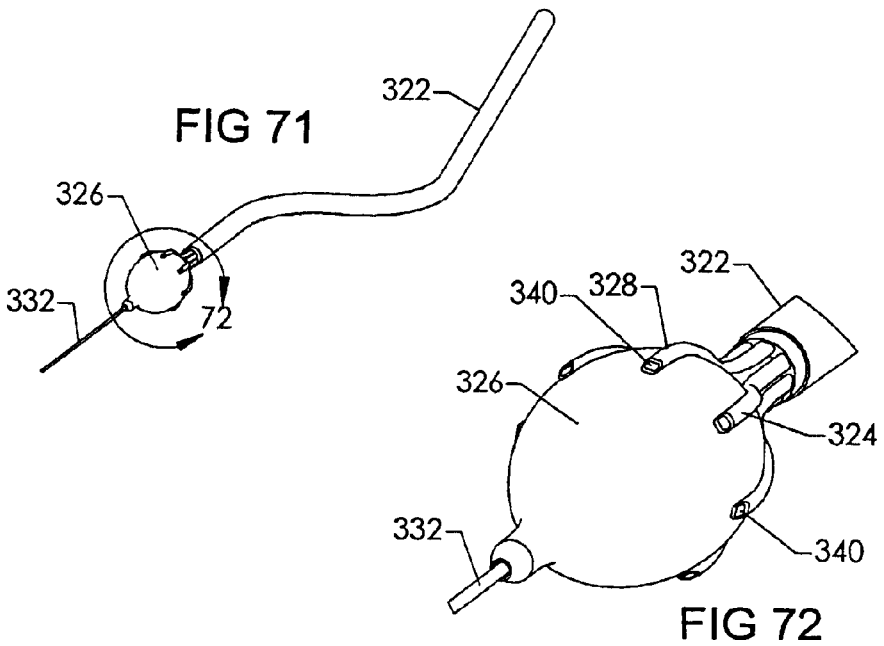

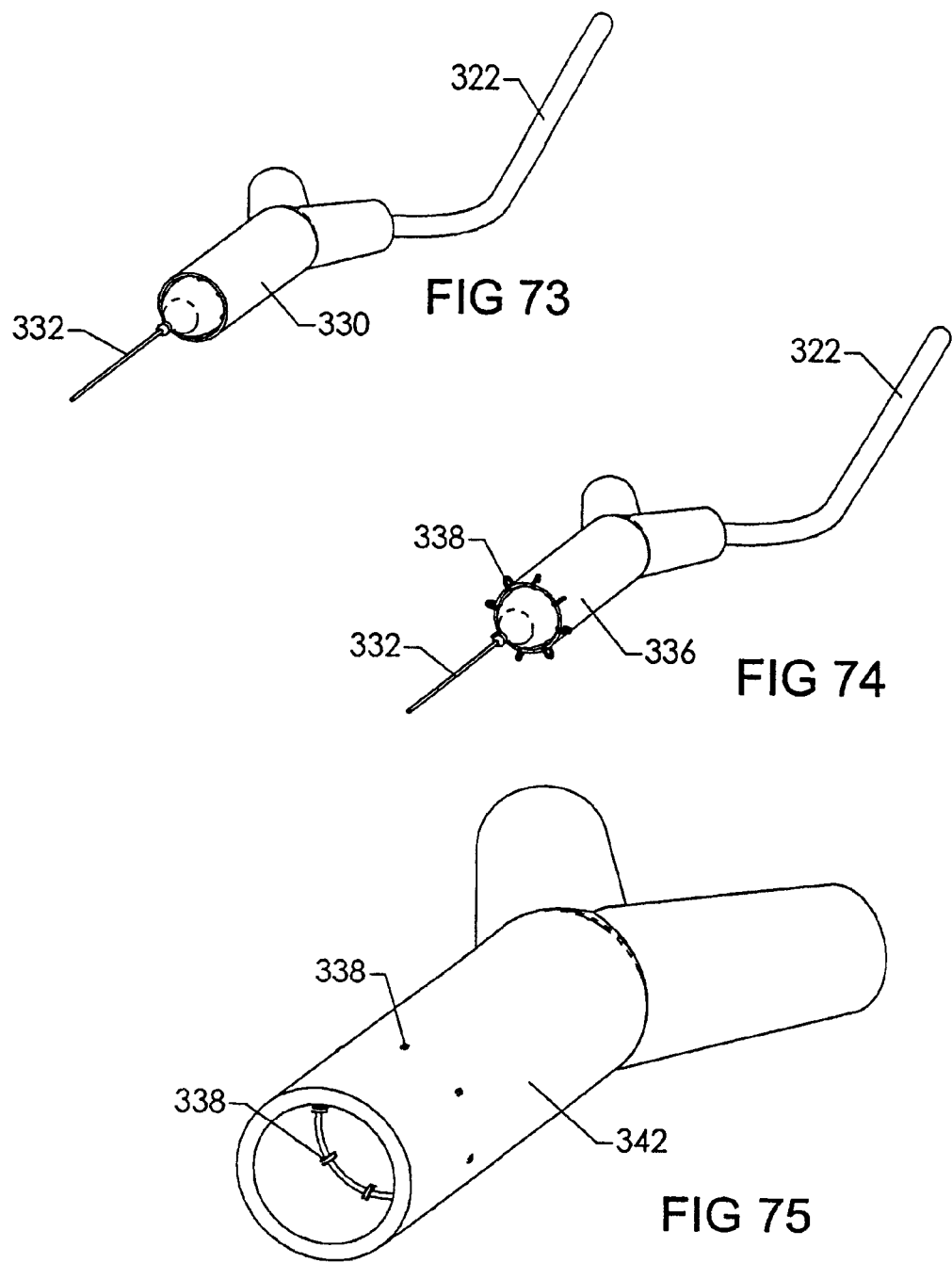

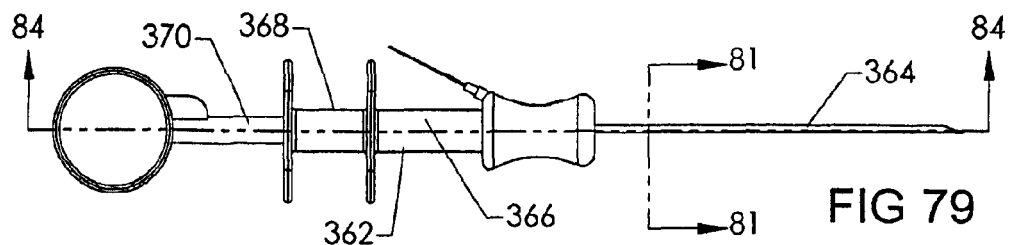
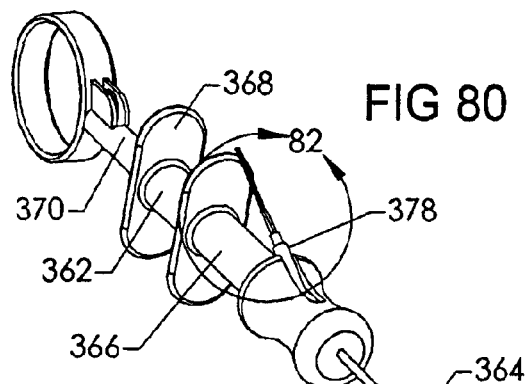
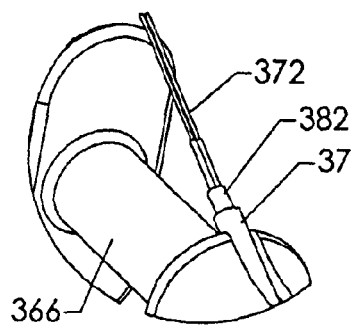
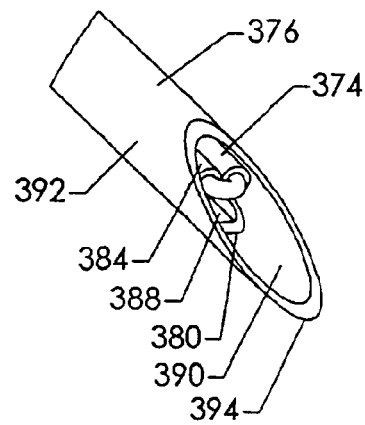
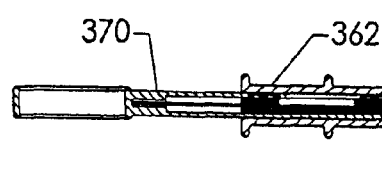

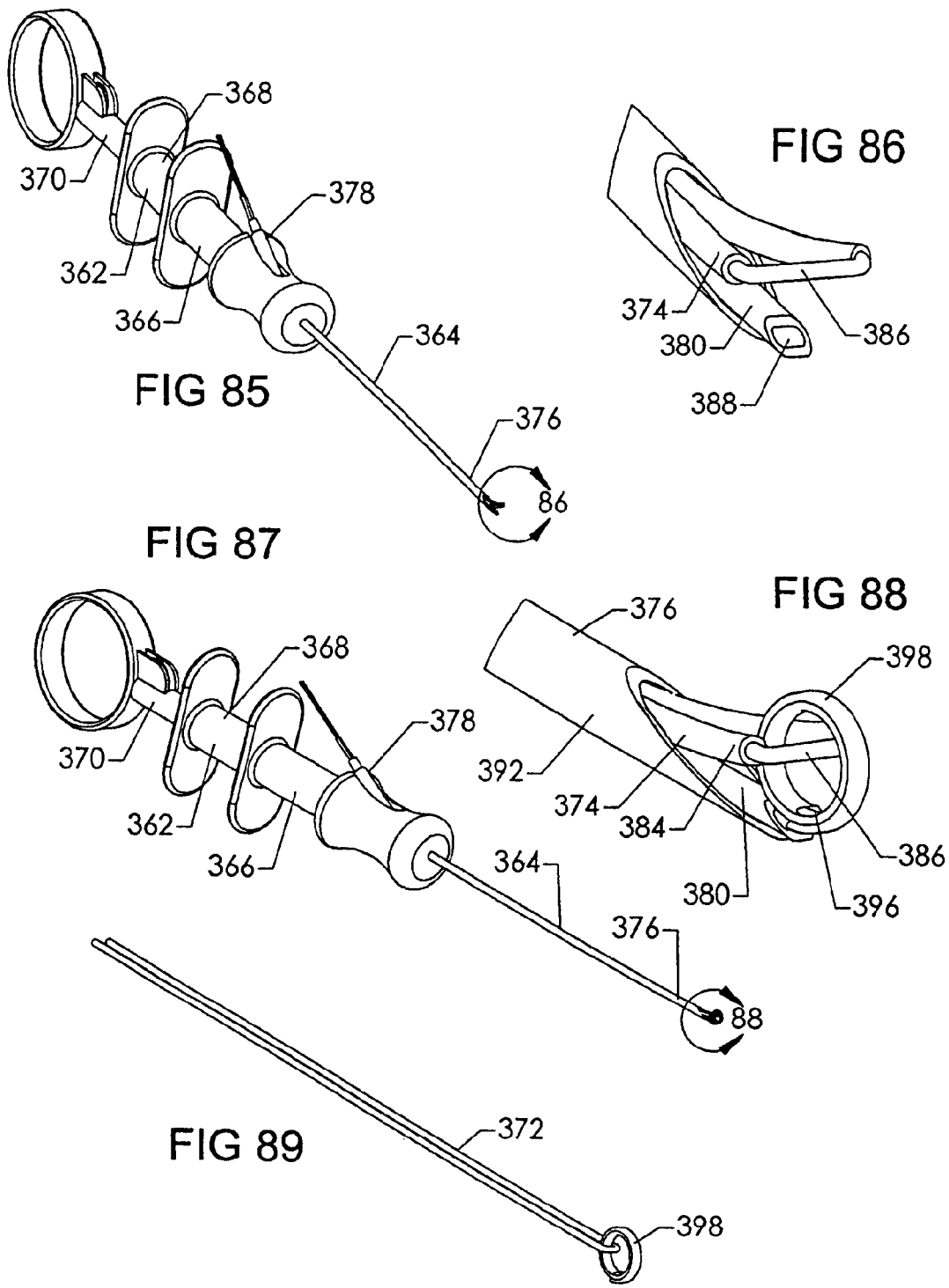

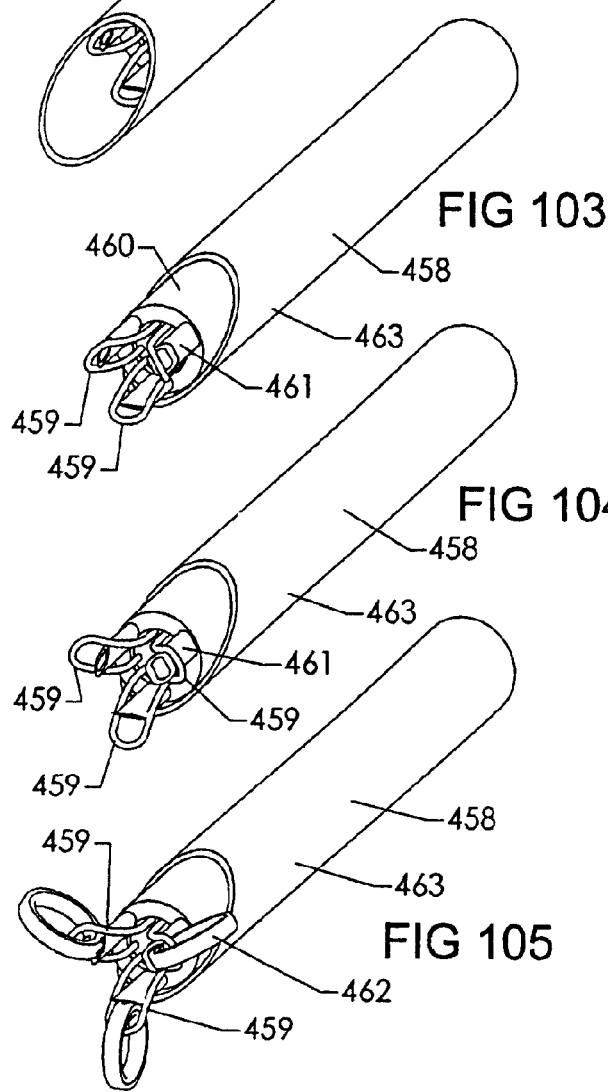

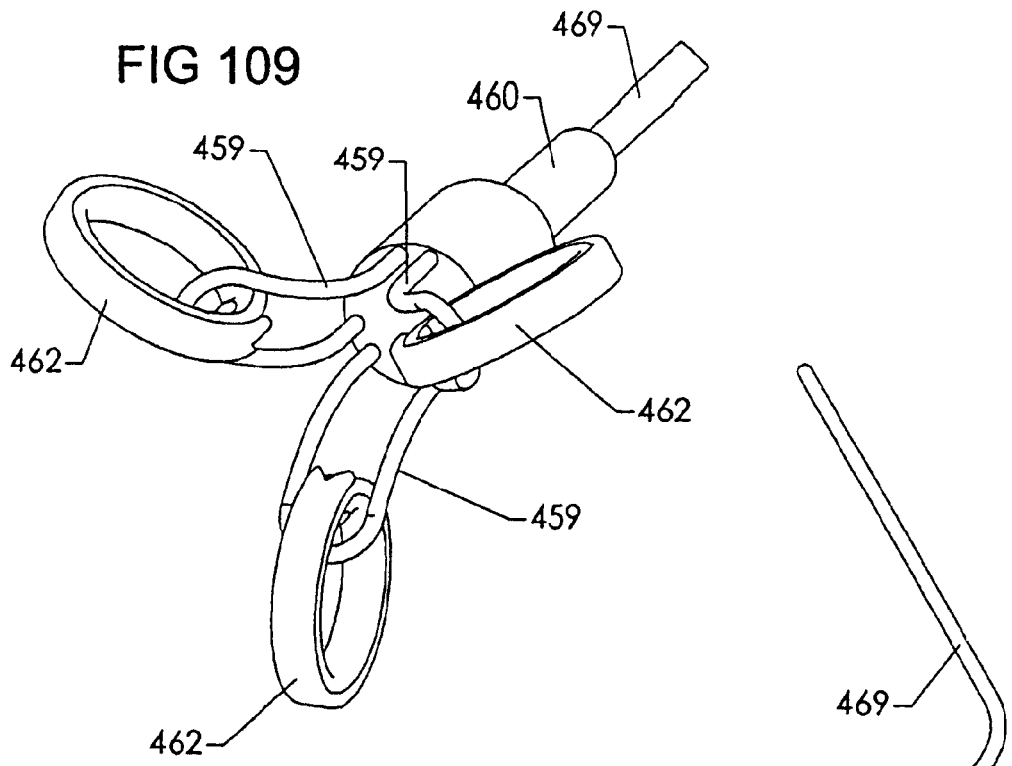
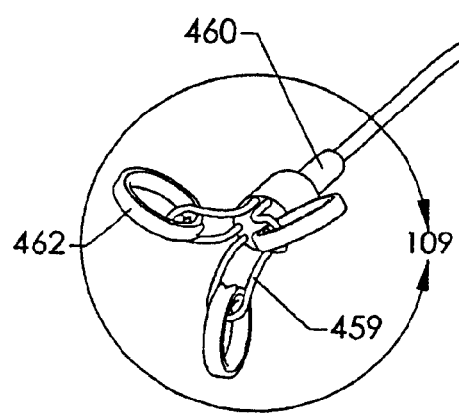

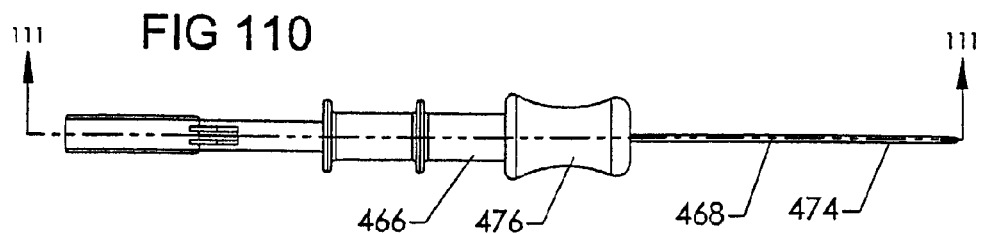
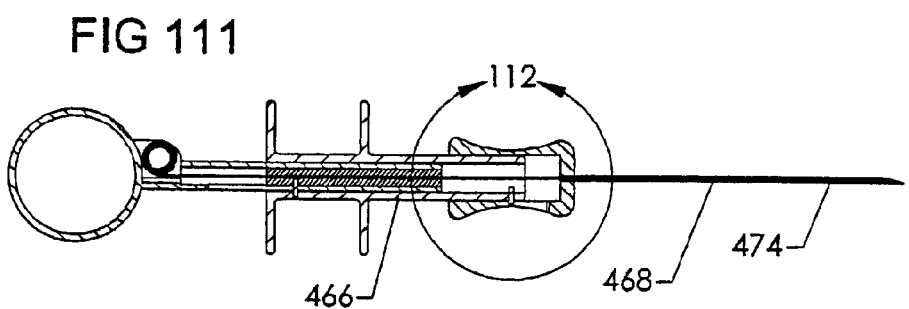
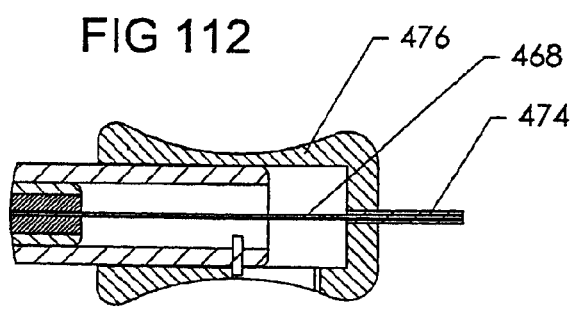
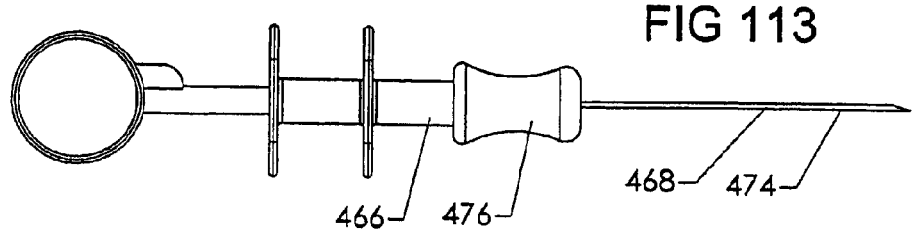

SURGICAL COILS AND METHODS OF DEPLOYING

RELATED APPLICATIONS

This application is a divisional of U.S. patent application Ser. No. 12/109,291, now U.S. Pat. No. 8,128,641, filed Apr. 24, 2008, by John L. Wardle, titled "Surgical Coils and Methods of Deploying", which is a divisional of U.S. patent application Ser. No. 10/386,260, filed Mar. 10, 2003, by John L. Wardle, titled "Surgical Coils and Methods of Deploying", which claims the benefit of priority from U.S. Provisional Patent Application Ser. No. 60/363,106, filed by John L. Wardle on Mar. 11, 2002, titled "Surgical Coils and Methods of Deploying", each of which are hereby incorporated by reference in their entirety.

BACKGROUND

Surgical stapling devices are widely used in surgical procedures to fasten body tissue quickly and efficiently by driving fasteners or staples into the tissue. In certain types of staplers, a single staple is typically formed around an anvil, e.g., skin staplers, for approximating tissue. Such staplers may employ staples having a variety of configurations, as for example a conventional U-shaped configuration and variations thereon. U-shaped staples have two opposed legs connected by a linear bridge. Therefore, the staple drivers have flat surfaces to correspond to the linear bridge portions of the staples. When deformed, such staples tend to form a B-shape, wherein the legs are curved towards the bridge and the chiseled end points are in a position to re-puncture the tissue being sutured. In such an orientation, a significant area of the deformed leg portions is not in extensive contact with the tissue.

In addition, suturing and suture line placement are necessary aspects of any surgical procedures. Surgeons have developed numerous techniques for tying sutures and placing suture lines over the years. Endoscopic surgical procedures such as arthroscopy, laparascopy, or thoroscopy are challenged with these tasks because development of a knot or placement of a suture line in a confined space is time consuming and requires great dexterity. Currently in endoscopic procedures, either the knots need to be tied externally to the body and inserted into the body and to the operative site using some kind of knot pushing device, or they need to be tied inside the body using long, instruments.

As such, what has been needed is to provide a device and method, which, secures tissue along a greater length and does so with a reduced tendency to re-puncture the tissue being secured. What has also been needed are simple approaches for placing sutures and suture lines in confined spaces. What has also been needed are devices and methods that could also be used as sutures to attach tissue, implant devices and surgical support materials for use in a wider range of none invasive surgical procedures. What has also been needed are device and methods for placing markers in tissue that do not have any sharp exposed points and do not migrate from the location of original deployment.

SUMMARY

The present invention relates to surgical coils and variety of devices that can effectively deploy surgical coils by different methods for a variety of clinical applications and indications. Techniques are also disclosed for simultaneously positioning and securing various attachment elements to surgical coils. Surgical coils disclosed herein can be used in numerous clinical applications including but not limited to tissue stapling, tissue anchoring including bone and suture anchors and tissue marking.

In one embodiment having features of the invention, a medical fastener is disclosed and includes an elongate element having a longitudinal axis and formed into an enclosed configuration with an overlapped portion with the elongate element making contact in the overlapped portion, the overlapped portion having a circumferential overlap of at least 300 degrees.

In another embodiment illustrating the features of the invention, a surgical marker for marking a position within the body of a patient is disclosed and includes an elongate element having a longitudinal axis and formed into an enclosed configuration with an overlapped portion with the elongate element making contact in the overlapped portion, and a contrast material in contact with the elongate element.

In yet another embodiment, a delivery device for deployment of a surgical coil is described and comprises an elongate delivery sheath having a proximal end and a distal end, an actuator body secured to a proximal portion of the elongate delivery sheath, a first ratchet member in substantially fixed relation with the actuator body having a grip feature configured to engage an advancing ribbon for prevent substantial proximal motion of the advancing ribbon relative to the delivery sheath, an actuator slidingly engaged with the actuator body, a second ratchet member having a grip feature configured to engage the advancing ribbon and being moveable with the actuator, and an advancing ribbon configured to apply axial force on an elongate element within the delivery sheath.

In another embodiment, a method for deploying a surgical coil in a patient's body is disclosed herein and includes positioning a distal end of a delivery sheath adjacent a deployment site, axially advancing a surgical coil through the delivery sheath, out of a distal port of the delivery sheath and into target tissue, and continuing to advance the surgical coil into the target tissue allowing an elongate element of the surgical coil to self-form into an enclosed configuration with an overlapped portion with the elongate element making contact with itself in the overlapped portion.

In still of another embodiment describing the features of the invention, a delivery device for simultaneous deployment of a plurality of surgical coils is disclosed and includes a delivery sheath housing, a plurality of delivery sheaths oriented and stabilized by the delivery sheath housing with each delivery sheath having a proximal end and a distal end, and plungers disposed within a a plurality of the delivery sheaths, and an actuator for applying axial force to advancing members that are axially translatable with respect to the delivery sheaths for distally advancing surgical coils disposed within the delivery sheaths.

In another embodiment illustrating the features of the invention, a method for deploying a plurality of surgical coils in a patient's body and includes positioning distal ends of a plurality of delivery sheaths stabilized by a delivery sheath housing adjacent a deployment site, axially advancing a plurality of surgical coils through the delivery sheaths, out of distal ports of the delivery sheaths and into target tissue, and continuing to advance the surgical coils into the target tissue allowing elongate elements of the surgical coils to self-form into an enclosed configuration with an overlapped portion of each elongate element making contact with itself in the overlapped portion.

In yet another embodiment, a delivery device for closure of a wound site and simultaneous deployment of a plurality of surgical coils across the wound is describe herein and includes a delivery sheath housing, a plurality of delivery sheaths oriented and stabilized by the delivery sheath housing with each delivery sheath having a proximal end, a distal end and a pre-formed outward radial bias away from other delivery sheaths for at least one distal end thereof, an outer sheath slidably disposed over at least a portion of the delivery sheath housing and delivery sheaths, and configured to constrain an outward radial displacement of the at least one distal end with the pre-formed bias when the outer sheath is disposed about the distal end with the pre-formed bias and to allow outward radial displacement of the distal end with the pre-formed bias when not disposed thereabout, plungers disposed within a plurality of the delivery sheaths for applying axial force to the delivery sheaths for distally advancing surgical coils disposed within the delivery sheaths.

In another embodiment, a method for forcing a wound closed and deploying a plurality of surgical coils across the wound to maintain closure and includes positioning distal ends of a plurality of delivery sheaths stabilized by a delivery sheath housing adjacent a deployment site with an outer sheath disposed about at least a portion of the delivery sheaths and delivery sheath housing in a proximally retracted position, advancing the distal ends of the delivery sheaths into target tissue at the deployment site with at least one delivery sheath disposed on either side of the wound, advancing the outer sheath distally in order to reduce an outward radial displacement of a distal end of at least one of the delivery sheaths thereby reducing the distance between the distal ends of at least two delivery sheaths and at least partially closing the wound, axially advancing a plurality of surgical coils through the delivery sheaths, out of distal ports of the delivery sheaths and into target tissue, and continuing to advance the surgical coils into the target tissue allowing elongate elements of the surgical coils to self-form into an enclosed configuration with an overlapped portion of each elongate element making contact with itself in the overlapped portion.

In still another embodiment describing the features of the invention, a delivery device for simultaneous deployment of a plurality of surgical coils from within a channel and has a delivery sheath housing, a plurality of delivery sheaths oriented and stabilized by the delivery sheath housing with each delivery sheath having a proximal end and a distal end, an outer sheath slidably disposed over at least a portion of the delivery sheath housing and delivery sheaths, an expanable member disposed between distal portions of the plurality of delivery sheaths and configured to expand the distal portions of the delivery sheaths in an outward radial direction when in an expanded state, and plungers disposed within a plurality of the delivery sheaths for applying axial force to a surgical coil within the delivery sheaths for distally advancing surgical coil.

In another embodiment, a method for deploying a plurality of surgical coils from within a channel is disclosed and includes positioning distal ends of a plurality of delivery sheaths stabilized by a delivery sheath housing at a deployment site within a cavity, expanding an expandable member which is surrounded by the the plurality of delivery sheaths until distal ends of the delivery sheaths are disposed against target material, axially advancing a plurality of surgical coils through the delivery sheaths, out of distal ports of the delivery sheaths and into target material, and continuing to advance the surgical coils into the target tissue allowing elongate elements of the surgical coils to self-form into an enclosed configuration with an overlapped portion of each elongate element making contact with itself in the overlapped portion.

In still another embodiment describing the features of the invention, a delivery device for deployment of a surgical coil and attachment member is disclosed which includes an elongate deployment shaft assembly including an elongate delivery sheath having a proximal end and a distal end, an attachment member having an attachment loop disposed adjacent a distal port of the delivery sheath which is configured to direct a surgical coil deployed from the distal port to surround the attachment loop, and an outer sheath slidably disposed about at least a portion of the delivery sheath and attachment member, and an actuator body secured to a proximal portion of the elongate deployment shaft configured to advance a surgical coil distally from the delivery sheath.

In another embodiment, a method for deploying a surgical coil and attachment member in a patient's body is described and includes positioning a distal end of a deployment shaft assembly adjacent a deployment site, axially advancing a surgical coil through a delivery sheath of the deployment shaft assembly, out of a distal port of the delivery sheath, into target tissue and around an attachment loop of the attachment member, continuing to advance the surgical coil into the target tissue allowing an elongate element of the surgical coil to self-form into an enclosed configuration with an overlapped portion with the elongate element making contact with itself in the overlapped portion.

In another embodiment illustrating the features of the invention, a deflectable delivery device for deployment of a surgical coil is described which includes an elongate deployment shaft assembly including an elongate delivery sheath having a proximal end, a distal end and a distal end portion that can be constrained to a straightened configuration and assumes a deflected curved configuration when the restraint is removed, and an outer sheath slidably disposed about at least a portion of the delivery sheath, and an actuator body secured to a proximal portion of the elongate deployment shaft assembly including a first actuator configured to advance the delivery sheath relative to the outer sheath and a second actuator configured to advance the surgical coil distally from a distal port of the delivery sheath.

In another embodiment, a method for deploying a surgical coil in a patient's body is disclosed which includes positioning a distal end of a deployment shaft assembly adjacent a deployment site, activating a first actuator to advance a delivery sheath distally from an outer sheath of the deployment shaft assembly until a distal end of the delivery sheath extends beyond a distal port of the outer sheath and extends in an outward radial direction from the distal port, activating a second actuator that axially advances a surgical coil through the delivery sheath, out of a distal port of the delivery sheath, into target tissue, continuing to advance the surgical coil into the target tissue allowing an elongate element of the surgical coil to self-form into an enclosed configuration with an overlapped portion with the elongate element making contact with itself in the overlapped portion.

These and other advantages of embodiments of the invention will become more apparent from the following detailed description when taken in conjunction with the accompanying exemplary drawings.

BRIEF DESCRIPTION OF THE DRAWINGS

FIG. 17 shows a perspective view of a surgical coil similar to that of FIGS. 2 and 3 in a straightened configuration.

FIG. 18 shows an alternative embodiment of a surgical coil in a straightened configuration, illustrating longitudinal slots cut into the elongate member of the surgical coil.

FIG. 19 illustrates an elevational view of a surgical coil in a straightened configuration.

FIG. 20 shows a transverse cross sectional view of the elongate member of the surgical coil of FIG. 19, taken along lines 20-20 of FIG. 19.

FIGS. 21-23 illustrate transverse cross sectional views of alternative embodiments of elongate members of surgical coils.

FIG. 23A is an elevational view of a surgical coil embodiment having an interlocking or self-aligning configuration.

FIG. 23B is a transverse cross sectional view of the surgical coil of FIG. 23A taken along lines 23B-23B of FIG. 23A illustrating a concave transverse cross sectional configuration of the elongate element of the surgical coil.

FIG. 28 is a perspective view of the delivery device of FIGS. 25-27 with the thumb ring of the delivery device in a completely advanced distal position with the surgical coil being completely deployed from a distal end of the delivery sheath of the delivery device.

FIG. 29 is an enlarged view of the encircled portion 29 of FIG. 28 showing the surgical coil of FIG. 28 being completely deployed from a distal end of the delivery sheath of the delivery device.

FIG. 30 is a perspective view of the delivery device of FIG. 25 with the thumb ring retracted back to a proximal position and ready to deploy another surgical coil disposed within the delivery sheath.

FIG. 37 is a perspective view of some of the interior components of the delivery device of FIG. 25 with some of the components removed for the purposes of illustration.

FIG. 38 is an enlarged perspective view of the encircled portion 38 of FIG. 37 showing the surgical coils at a distal portion of the delivery device.

FIG. 39 is a further enlarged perspective view of the encircled portion 39 of FIG. 38 showing a junction between a distal end of a first elongate member of a surgical coil and a proximal end of an elongate member of a second surgical coil.

FIG. 46 is a perspective view of a ratchet delivery device that is configured to accept a surgical coil cassette for deploying a large number of surgical coils from a single delivery device.

FIG. 47 is a perspective view of the delivery device of FIG. 46 with the surgical coil cassette removed from the delivery device.

FIG. 52 is a perspective view of the surgical coil cassette shown in FIGS. 46 and 47.

FIG. 53 is another perspective view of the surgical coil cassette shown in FIG. 52.

FIG. 54 is an enlarged perspective view of the encircled portion 54 of FIG. 52 showing the surgical coil cassette.

FIG. 55 is an enlarged perspective view of the encircled portion 55 of FIG. 53 showing the surgical coil cassette.

FIG. 59 is a perspective view of a delivery device configured to deploy 8 surgical coils simultaneously with 8 delivery sheaths extended distally from the delivery device and extending toward an artificial heart valve.

FIG. 60 is a perspective view of the delivery device of FIG. 59 shown with distal ends of the 8 delivery sheaths engaged and penetrating a surface of the heart valve.

FIG. 61 is a perspective view of the delivery device of FIG. 60 with the 8 surgical coils being deployed from the 8 delivery sheaths.

FIG. 62 is a perspective view of the artificial heart valve of FIG. 61 shown with the 8 surgical coils fully deployed.

FIG. 63 is a perspective view of a distal portion of a delivery device configured to deploy 2 surgical coils simultaneously in order to close a cut or incision in soft tissue.

FIG. 63A illustrates an elevational view in section of the delivery device of FIG. 63 with the delivery sheaths retracted within an outer sheath.

FIG. 64 is a perspective view of the distal portion of the delivery device of FIG. 63 shown with an outer sheath of the delivery device retracted proximally in order to allow distal ends of the delivery sheaths to be exposed and expand in a radial direction prior to engagement of tissue.

FIG. 64A illustrates an elevational view in section of the delivery device of FIG. 63 with the delivery sheaths extended from the outer sheath with the delivery sheaths expanded in an outward radial direction.

FIG. 65 is a diagrammatic view in perspective of the delivery device of FIG. 64 with the exposed delivery sheaths engaging the surface of tissue adjacent an open incision.

FIG. 66 shows the delivery device of FIG. 65 with the distal ends of the delivery sheaths penetrating the tissue adjacent the incision with the outer sheath advanced slightly distally in order to decrease the radial gap between the distal ends of the delivery sheaths and close the incision in the tissue.

FIG. 69 is a perspective view of a distal portion of a balloon delivery device which is configured to deploy multiple surgical coils to the wall of a passageway from within the passageway.

FIG. 70 is a diagrammatic view in perspective of the delivery device of FIG. 69 disposed within a passageway of an AAA stent.

FIG. 71 is a perspective view of the distal portion of the delivery device of FIG. 69 shown with an expansion balloon of the distal end of the delivery device in an expanded state forcing distal ends of multiple delivery sheaths to expand in an outward radial direction.

FIG. 72 is an enlarged view in perspective of the encircled portion 72 in FIG. 71 showing the distal end of the delivery device.

FIG. 73 is a diagrammatic view in perspective of the distal end of the delivery device shown in FIG. 72 in an expanded state within the passageway of the AAA stent with the distal ends of the delivery sheath pressed in an outward radial direction against an inside wall of the AAA stent.

FIG. 74 shows the delivery device of FIG. 73 with the surgical coils deployed from the delivery device through a proximal end of the AAA stent with the aorta adjacent the delivery device not shown for purposes of illustration.

FIG. 75 shows a perspective view of the AAA stent within an aorta of a patient with the surgical coils of FIG. 74 deployed through the proximal end of the AAA stent and the adjacent tissue of the aorta so as to secure the proximal end of the AAA stent to the aortic wall.

FIG. 79 is a perspective view of a delivery device that is configured to deploy a surgical coil with a suture attachment.

FIG. 80 is a perspective view of the delivery device of FIG. 79.

FIG. 81 is a transverse cross sectional view of the delivery device of FIG. 79 taken along lines 81-81 of FIG. 79.

FIG. 82 is an enlarged view in perspective of encircled portion 82 shown in FIG. 80.

FIG. 83 is an enlarged view in perspective of the encircled portion 83 shown in FIG. 80 illustrating more detail of a distal end of the delivery device.

FIG. 84 is a bottom view in partial section taken along lines 84-84 of FIG. 79.

FIG. 85 is a perspective view of the delivery device of FIG. 79 with an outer sheath of the delivery device retracted proximally to expose suture alignment tubes at the distal end of the delivery device.

FIG. 86 is an enlarged view in perspective of encircled portion 86 of FIG. 85 showing more detail of the distal end of the delivery device with the suture alignment tubes exposed.

FIG. 87 is a perspective view of the delivery device illustrating a surgical coil being deployed from the distal end of a delivery sheath of the delivery device.

FIG. 88 is an enlarged view in perspective of the encircled portion 88 of FIG. 87 illustrating more detail of the surgical coil being deployed about a portion of the suture line and tissue (not shown) simultaneously.

FIG. 89 is a perspective view of a surgical coil deployed about a portion of a suture line within tissue (not shown) with the delivery device retracted.

FIG. 102 is a perspective view of a distal portion of a deployment shaft assembly configured for delivery of a plurality of surgical coils.

FIGS. 103 and 104 are perspective views of the deployment shaft assembly of FIG. 102 with an outer sheath of the assembly retracted proximally with respect to the delivery sheath housing, allowing three flexing loop wires of the attachment to expand radially outward from a longitudinal axis of the deployment shaft assembly.

FIG. 105 is a perspective view of the deployment shaft assembly of FIG. 104 with three surgical coils deployed about the respective flexing loop wires.

FIG. 106 is an end view of the deployment shaft assembly in a state of deployment shown in FIG. 102.

FIG. 107 is an end view of the deployment shaft assembly in a state of deployment shown in FIG. 105.

FIG. 108 is a perspective view of the attachment member wherein the three flexing loop wires are respectively secured to three surgical coils within tissue (not shown) and an attachment line is secured to and extending proximally from the attachment housing.

FIG. 109 is an enlarged view of the encircled portion 109 in FIG. 108. FIG. 110 is a top view of a deployment device having a deflecting delivery sheath in a deployment shaft assembly.

FIG. 111 is an elevational view in partial section of the delivery system of FIG.

110 taken along lines 111-111 of FIG. 110.

FIG. 112 is an enlarged view in partial section of the encircled portion 112 of FIG. 111 illustrating a finger grip, pin and slot arrangement of the delivery device.

FIG. 113 is an elevational view of the delivery device of FIG. 110.

Figure 114:

FIG. 114 is a perspective view of the delivery device of FIG. 113 wherein the sliding finger grip is positioned distally and a distal end portion of a deflecting delivery sheath is extending from a distal end of the deployment shaft assembly with a distal port of the deflecting delivery sheath being directed radially away from a longitudinal axis of the deployment shaft assembly and being radially displaced from same.

Figure 115:
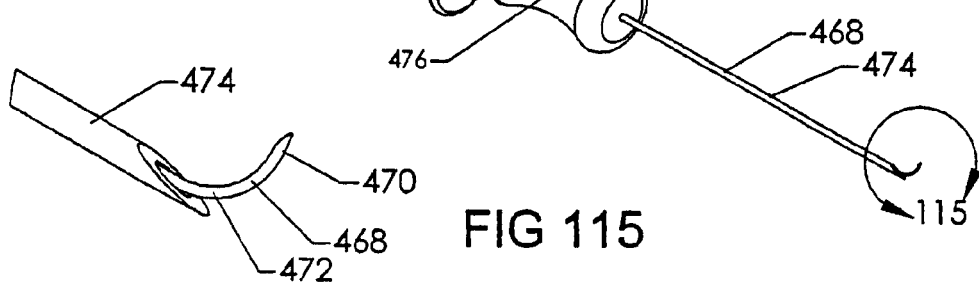

FIG. 115 is an enlarged view of the encircled portion 115 of FIG. 114.

Figure 116:

FIG. 116 is a perspective view of the delivery device of FIG. 114 wherein a thumb ring is in an advanced distal position and a surgical coil is being deployed from a distal end of the deflecting delivery sheath.

Figure 117:
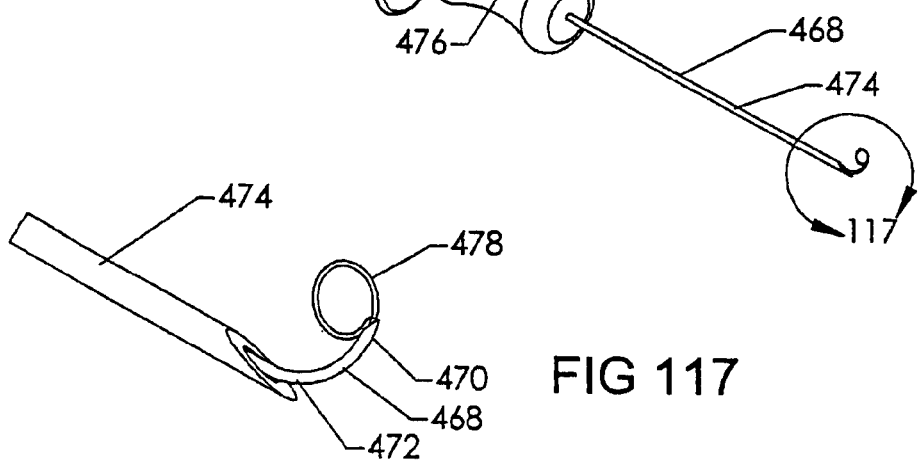

FIG. 117 is an enlarged view of encircled portion 117 of FIG. 116 illustrating a surgical coil being deployed from a distal end of the deflecting delivery sheath.

Figure 118:
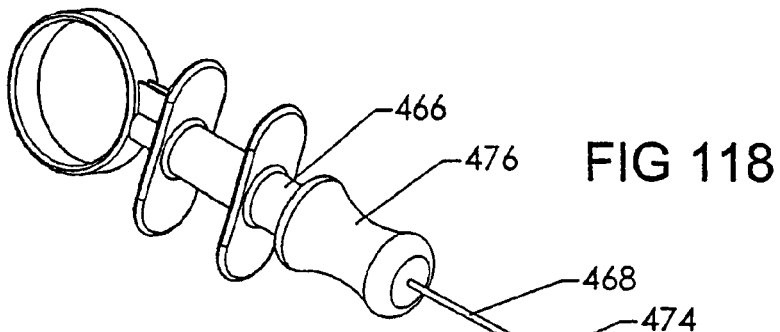

FIG. 118 is a perspective view of of the delivery device with the thumb ring fully advanced distally.

Figure 119:
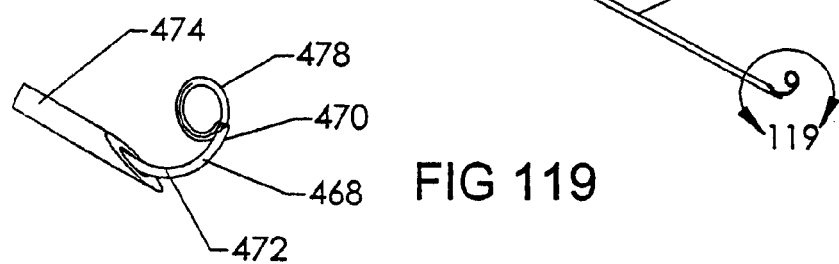

FIG. 119 is an enlarged view of encircled portion 119 illustrating a surgical coil being deployed from a distal end of the deflecting delivery sheath.

Figure 120:
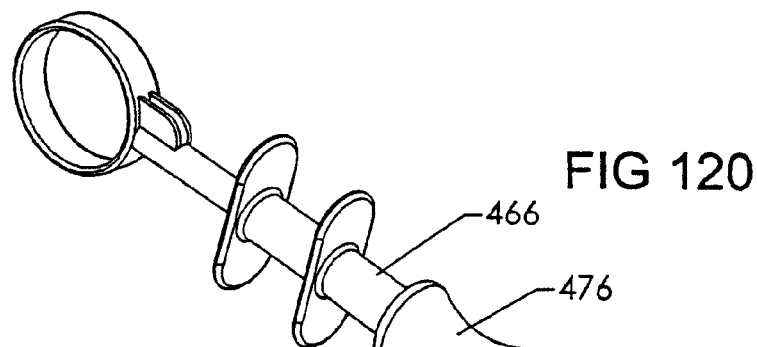

FIG. 120 is a perspective view of the delivery device with the thumb ring retracted proximally after deployment of the surgical coil as show in FIG. 118.

Figure 121:
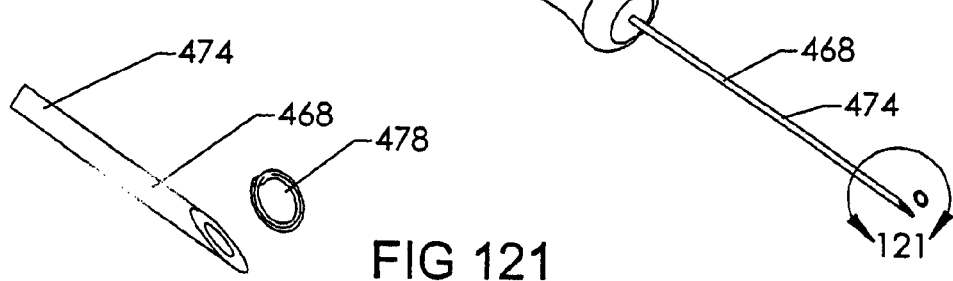

FIG. 121 is an enlarged view of encircled portion 121 of FIG. 120 illustrating the surgical coil fully deployed in adjacent tissue (not shown).

Figure 122:
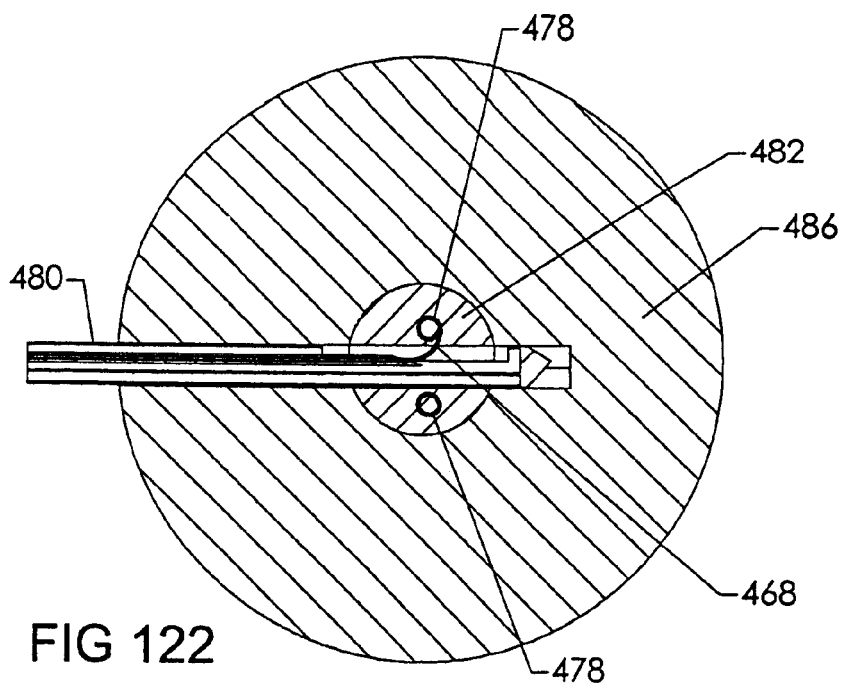

FIG. 122 is a schematic view in partial section of tissue with a distal portion of a mammatome biopsy device disposed within a lesion of the tissue with a distal portion of a delivery sheath extending radially from a lateral aperture in the mammatome and a surgical marking coil being deployed from the distal portion of the delivery sheath into the lesion.

Figure 123:
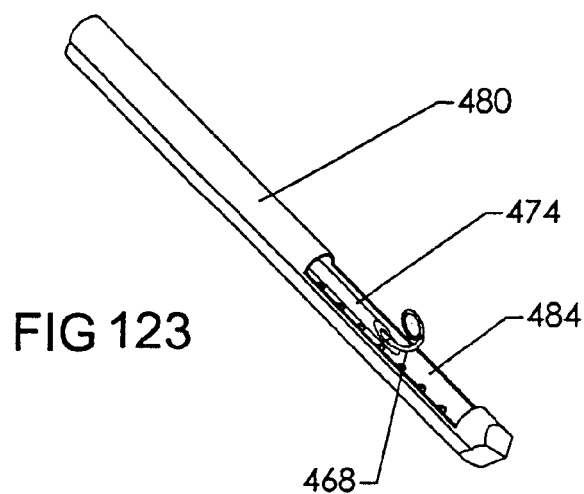

FIG. 123 is a perspective view of a distal portion of a mammatome bipsy device with a lateral aperture with a distal portion of a delivery sheath extending radially from the lateral aperture in the mammatome and a surgical marking coil being deployed from the distal portion of the delivery sheath into the lesion.

Figure 124:
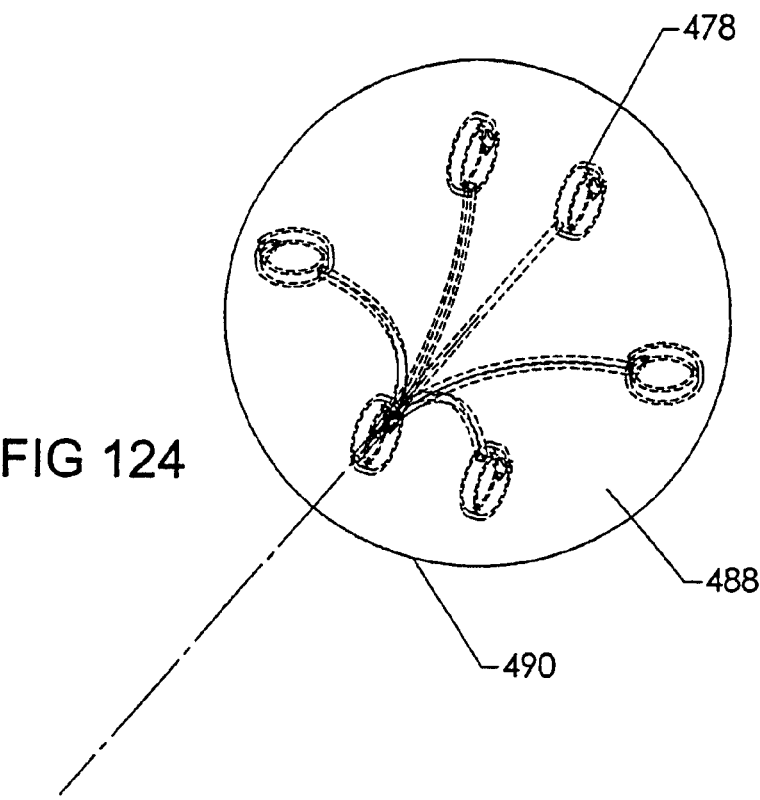

FIG. 124 is a perspective view of a deployment pattern for surgical coil markers illustrating a plurality of surgical coil markers deployed at a distal extremity and several radially extended positions which can serve to define the boundaries of a suspect tissue mass for imaging by medical imaging methods.

Figure 125:
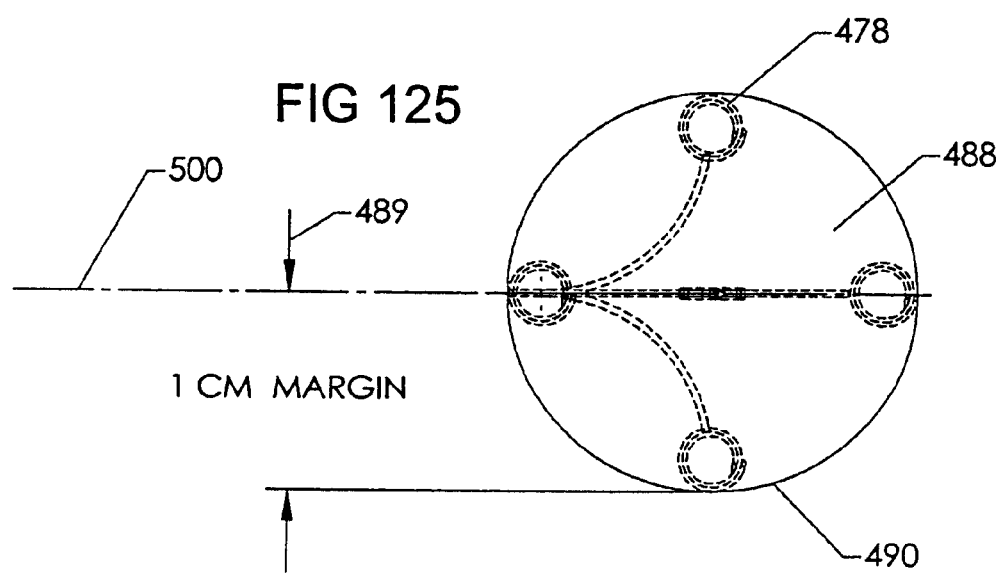

FIG. 125 is an elevational view of the deployment pattern for surgical coil markers of FIG. 124 illustrating a plurality of surgical coil markers deployed at a distal extremity, proximal extremity and radially extended positions which can serve to define the boundaries of a suspect tissue mass for imaging by medical imaging methods.

Figure 126:
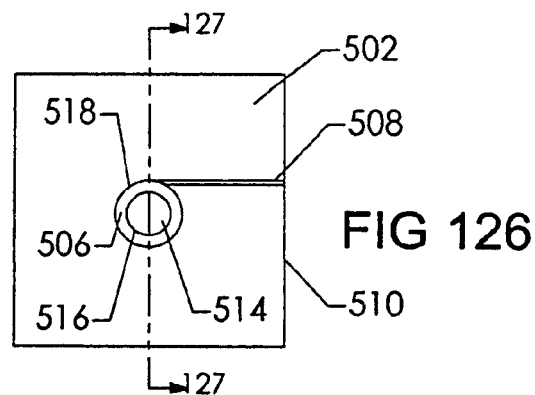

FIG. 126 is a top view of an embodiment of a surgical coil shape forming jig.

Figure 127:
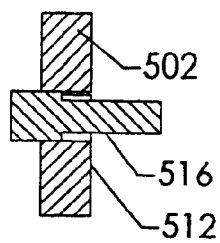

FIG. 127 is a transverse cross sectional view of the shape forming jig of FIG. 126 taken along lines 127-127 of FIG. 126.

Figure 128:
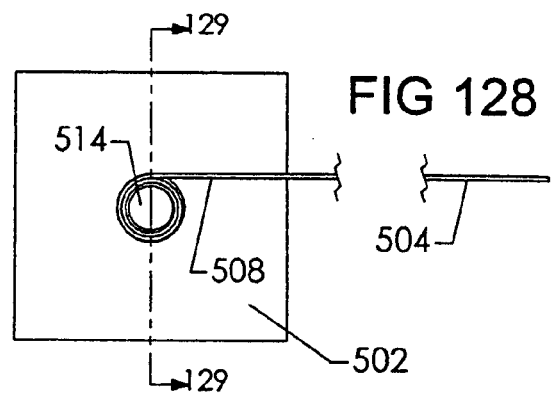

FIG. 128 is top view of the shape forming jig of FIG. 126 with a portion of metallic ribbon material inserted into the jig.

Figure 129:
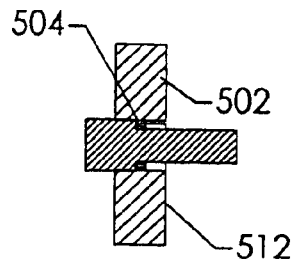

FIG. 129 is a transverse cross sectional view of the jig and metalic ribbon material of FIG. 128 taken along lines 128-128 of FIG. 127.

Figure 130:
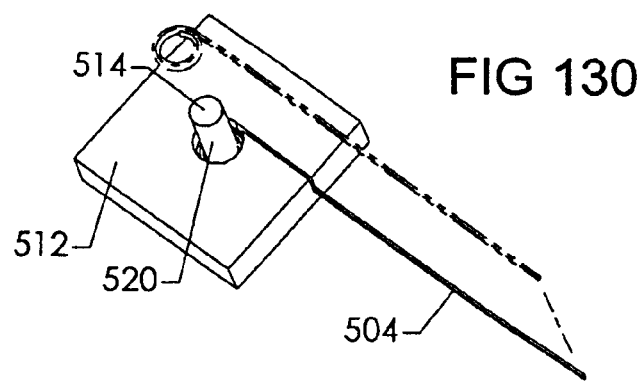

FIG. 130 is a perspective view of the jig of FIG. 129 illustrating removal of the metallic ribbon material after shape setting of the ribbon material.

Figure 131:
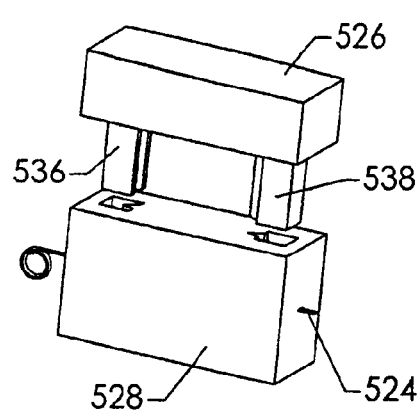

FIG. 131 is a perspective view of a punch and die configured to cut the shape formed metallic ribbon shown if FIG. 130, which is shown disposed within the die, to length and form a sharp distal tip and wedged proximal end of a surgical coil.

Figure 132:
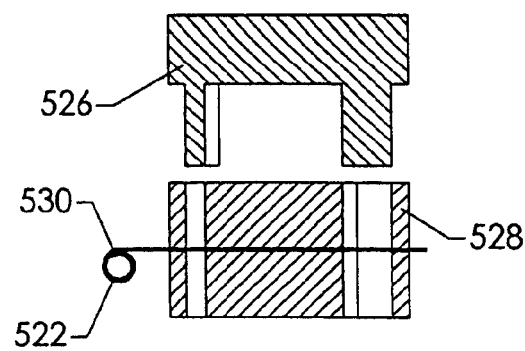

FIG. 132 is an elevational view in partial section of the punch and die shown if FIG. 130, with a non-shape formed portion of the metallic ribbon disposed within the die.

Figure 133:
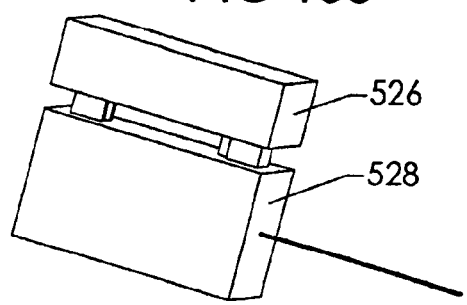

FIG. 133 is a perspective view of the punch and die of FIG. 131 with the punch partially inserted into the die adjacent the shape formed portion of the metallic ribbon material which has been pulled into the die to align the shape formed portion with the die cavities.

Figure 134:
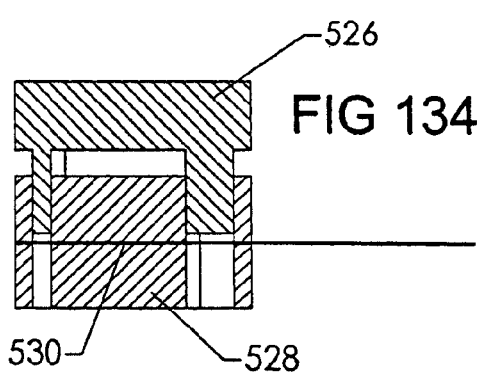
Figure 135:
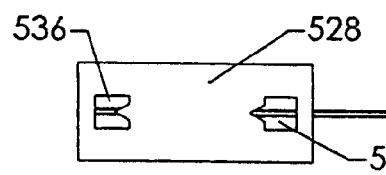

FIG. 135 is a bottom view of the punch and die of FIG. 134 with the shape formed portion of the metallic ribbon material aligned with the die cavities.

Figure 136:
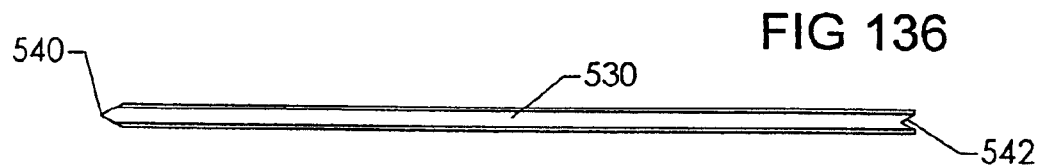

FIG. 136 shows an elongate element embodiment.

DETAILED DESCRIPTION

Embodiments of surgical coils are disclosed which can secure tissue along a significant length and do so with a minimal tendency to re-puncture the tissue being secured. Embodiments of the present device also place surgical coils that complete a full circular path and can be used as sutures to attach tissue, implant devices and surgical support materials in addition to being made small in profile in order to make a wide range of non-invasive surgical procedures possible.

Suturing and suture line placement are necessary aspects of most surgical procedures. Embodiments of the current device provide devices and methods for placing sutures and suture lines in confined spaces. Suture anchors can be used to mount suture to bone for subsequent attachment of ligaments, tendons, or other tissue. Some known suture anchors are inserted into pre-drilled holes in the bone, while others are "self-tapping" and are threaded into the bone through the bone surface. In either case, ridges, which extend outwardly from the exterior surface of the suture anchor facilitate retention of the anchor in the bone tissue.

Anchors of this type typically use up a large surface area relative to the size of the suture and so the number of anchors that can be used in any single location of placement is limited due to the confined surgical space at the site of installation. Another limitation of these known anchors is that they only can only be reliably used when the full length of the anchor is embedded in bone. Embodiments of the current invention provide devices and methods for reliable bone anchoring sutures that require minimal bone surface disruption space and skill to install and can also be reliably attached to thin cross sections of bone.

It is desirable and often necessary to perform procedures for detecting, sampling, and testing lesions and other abnormalities in the tissue of humans particularly in the diagnosis and treatment of patients with cancerous tumors, pre-malignant condition and other diseases or disorders. It can be of considerable benefit in many circumstances to be able to permanently mark the location or margins of such a lesion prior to or immediately after removing a sample of the tissue for testing. Marking tissue of a lesion prior to removal helps to ensure that the entire lesion is excised, if desired. Alternatively, a lesion is inadvertently removed in its entirety, marking the biopsy site immediately after the procedure would enable reestablishment of its location for future identification.

Known tissue marking devices and methods typically attach a micro-staple device to an internal wall of a cavity of a biopsy site, these types of staples, clips or open medical screws can be easily dislodged in some circumstances, and, as such, can be unreliable in accurately defining a target site. In addition, they generally have sharp exposed points that can be a hazard to a surgeon who subsequently has to remove the marked area. A marker with sharp exposed points can puncture or tear a surgical glove along with the surgeon's skin. As a result, both physician and patient are at risk of transmitted immunodeficiency virus or hepatitis, as well as other high risk contagions. Embodiments of the present invention provide reliable marking methods and markers with little or no exposed sharp points.

In addition, in some clinical settings identification and localization of a suspect mass is performed by a radiologist who, using current methods, places a localization wire or "Kopan's" wires into the breast of a patient to define and locate the tissue mass to be removed. A hollow needle, containing the localization wire, is inserted into the breast under local anesthesia. The localization wire is inserted while the breast is under compression during the imaging procedure, until the distal end of the localization wire passes through the suspect mass. The localization wire is anchored distally beyond the mass by means such as a barb or hook at the distal end of the wire.

The needle is then removed from the body, leaving the wire in place and extending from the body as a marker for the surgeon. However, this type of known localization wire can move relative to the lesion when the breast is released from compression. Specifically, the distal end of the wire often migrates and thus shifts position with respect to the targeted tissue mass. This may lead to inaccurate placement of the incision for the biopsy, with the result that either an excess of tissue outside of the target tissue mass is removed, or less than all of the target tissue mass is removed. In addition, the wire is sometimes inadvertently severed, or pulled out during surgery.

In addition, there is frequently a day or two time delay between placement of the localization wire and surgical removal of the suspect tissue mass so the patent may have to tolerate a localization wire protruding from the breast during this time period. Embodiments of the present invention provide devices and methods for reliable tissue anchoring that will not migrate from a target tissue mass, and can include a flexible attachment line for a surgeon to follow to the target lesion and which can be left in place and not inconvenience a patient excessively while waiting for surgery.

Figure 1:
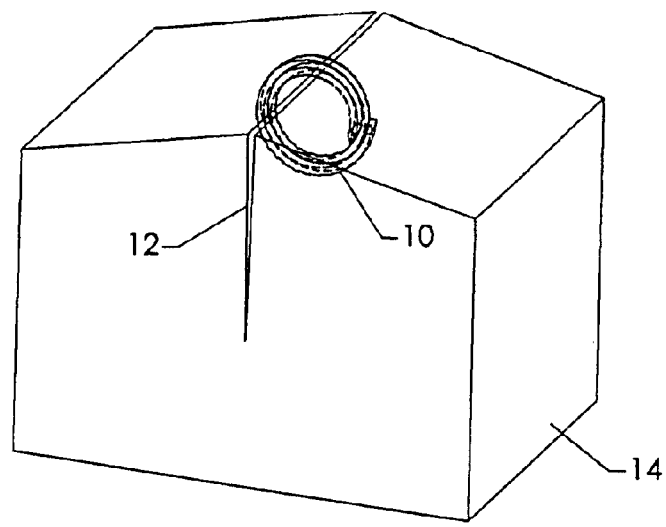
FIG. 1 shows a perspective view, partially cut away, of a surgical coil deployed within the surface of tissue holding an incision closed.

FIG. 1 shows an embodiment of a surgical coil 10 deployed across a cut 12 in a portion of tissue 14 serving to hold the cut in the tissue portion closed. The surgical coil 10 is shown in more detail in the perspective views of FIGS. 2 and 3, wherein an elongate element 16 having a ribbon-like configuration is coiled upon itself with a significant amount of overlap or circumferential overlap of adjacent portions of the elongate element 16. In some embodiments of the surgical coil 10, the overlapped portions of elongate element 16 are tightly coiled and in contact with each other. A wedge shaped tissue penetrating distal tip 18 is configured on a distal end 20 of an elongate element 16 of the surgical coil 10. A wedge shaped recess 22 is formed into a proximal end 24 of the elongate element 16 of the surgical coil 10.

Figure 4:
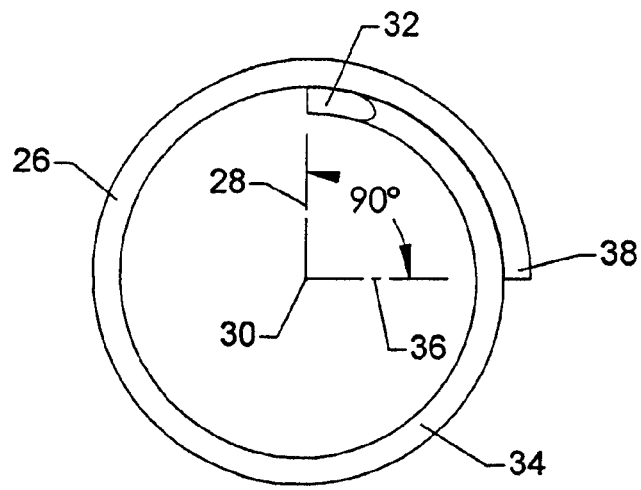
FIG. 4 is an elevational view of a surgical coil embodiment having about 90 degrees of circumferential overlap in the coils.
Figure 5:
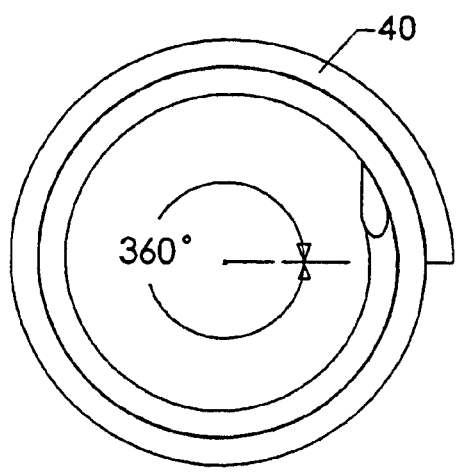
FIG. 5 is an elevational view of a surgical coil embodiment having about 360 degrees of circumferential overlap in the coils.

FIGS. 4 and 5 demonstrate circumferential overlap of coil embodiments. FIG. 4 shows an embodiment of a surgical coil 26 having about 90 degrees of circumferential overlap. The circumferential overlap is delineated by the angle formed between a line 28 drawn from an axis 30 of the surgical coil 26 to a first end 32 of an elongate element 34, and a line 36 drawn from the axis 30 to a second end 38 of the elongate element 34, inclusive of full rotational angles, i.e., 360 degrees for each full rotation of overlap of the elongate element 34 of the surgical coil 26. FIG. 5 illustrates a surgical coil 40 having about 360 degrees of circumferential overlap.

Figure 6:
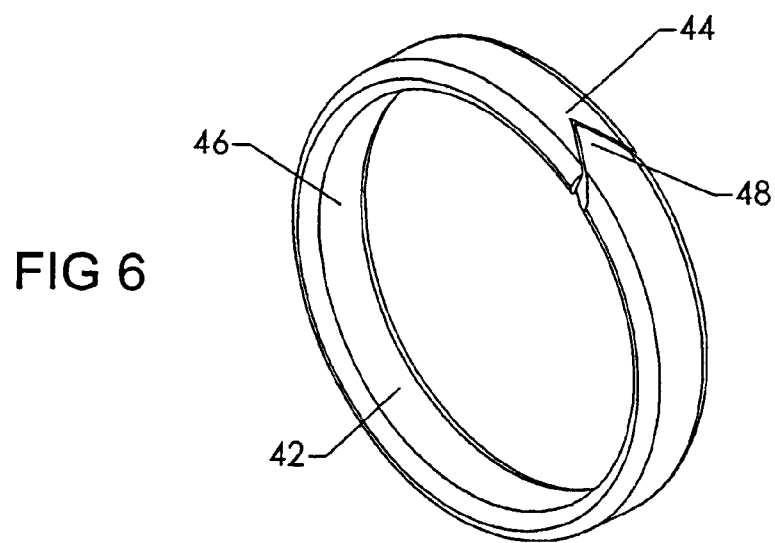
FIG. 6 is a perspective view of a surgical coil with no overlap in the coils and having the distal end of the elongate element of the coil engaged with the proximal end of the elongate element.
Figure 7:
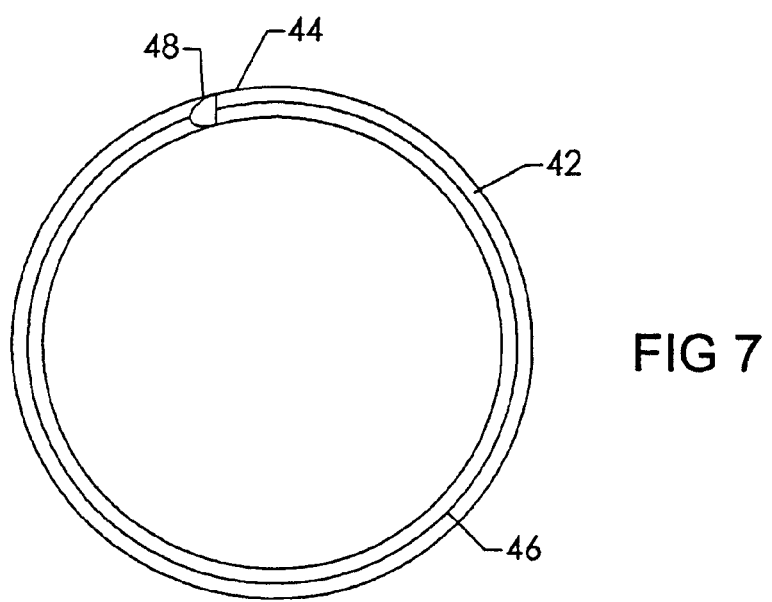
FIG. 7 is an elevational view of the surgical coil of FIG. 6.

FIGS. 6 and 7 illustrate a surgical coil 42 having substantially no circumferential overlap wherein the proximal end 44 of an elongate element 46 of the surgical coil 42 directly engages a distal end 48 of the elongate element 46 of the surgical coil 42 in a smooth and continuous circular configuration. Such a configuration may be useful as a surgical coil marker where the surgical coil 42 is not likely to be subjected to high stress loads.

Figure 8:
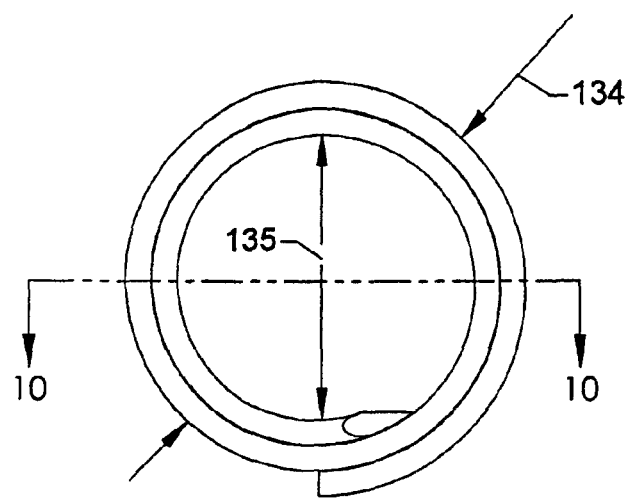
FIG. 8 is an elevational view of a surgical coil, similar to the surgical coil of FIGS. 1 and 2, illustrating the tightly wound nature of the elongate element of the surgical coil which has approximately 360 degrees of circumferential overlap.
Figure 9:
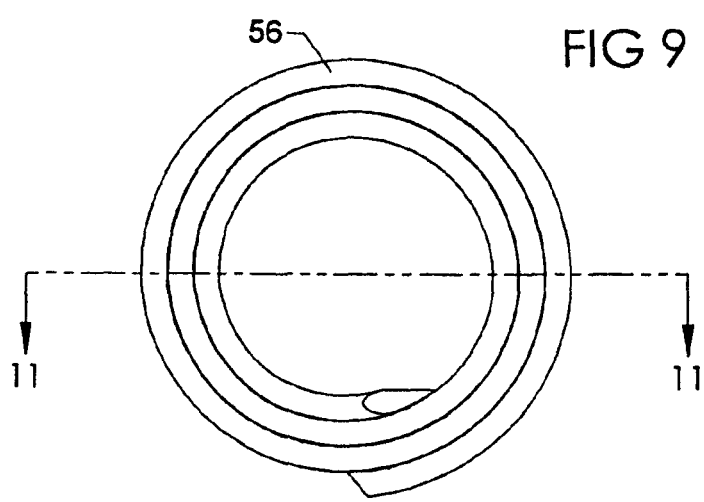
FIG. 9 is an elevational view of a surgical coil, similar to that of FIG. 8, but having approximately 720 degrees of circumferential overlap.
Figure 10:
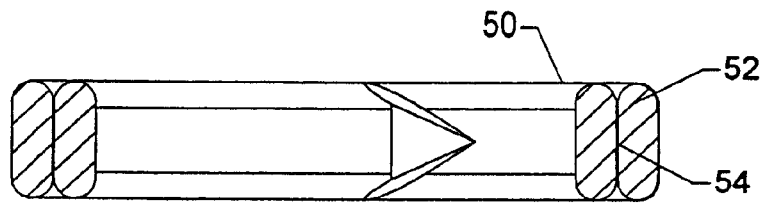
FIG. 10 is transverse cross sectional view of the surgical coil of FIG. 8 taken along lines 10-10 of FIG. 8.
Figure 11:
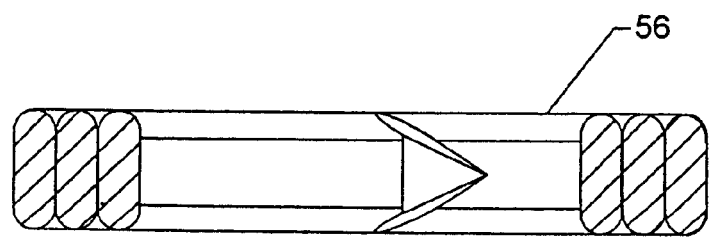
FIG. 11 is a transverse cross sectional view of the surgical coil of FIG. 9 taken along lines 11-11 of FIG. 9.

FIGS. 8-11 illustrate two additional embodiments of surgical coils. FIG. 8 is a side or elevational view of a surgical coil 50 having about 360 degrees of circumferential overlap. A transverse cross sectional view of the surgical coil 50 of FIG. 8 can be seen in FIG. 10 which shows a transverse cross section of the elongate element 52 of the surgical coil 50. As can be seen from both FIG. 8 and FIG. 10, a junction 54 between overlapped adjacent portions of the elongate element 52 are in close contact, forming a tightly wound surgical coil 50. FIGS. 9 and 11 illustrate similar views of a surgical coil 56 having a circumferential overlap of about 700 degrees to about 740 degrees. FIGS. 8 and 10 illustrate surgical coil 50 having a circumferential overlap of about 360 degrees, however, similar and useful embodiments may have a circumferential overlap of at least about 300 degrees. Other surgical coil 50 embodiments may have a circumferential overlap of about 300 to about 420 degrees, more specifically, about 340 to about 380 degrees. Still other embodiments of surgical coils 50 may have a circumferential overlap of about 350 degrees to about 750 degrees.

Figure 12:
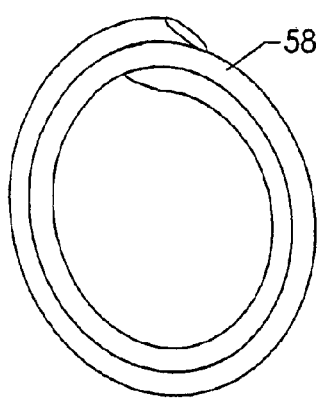
FIGS. 12-14 illustrate various embodiments of surgical coil winding configurations.
Figure 14:
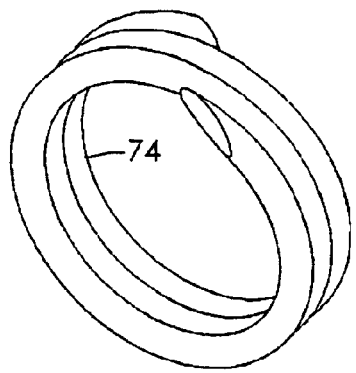
Figure 13:
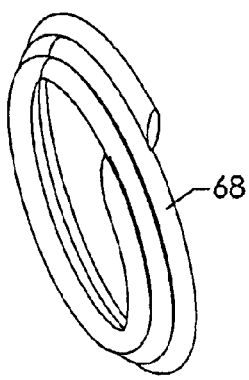
Figure 15:
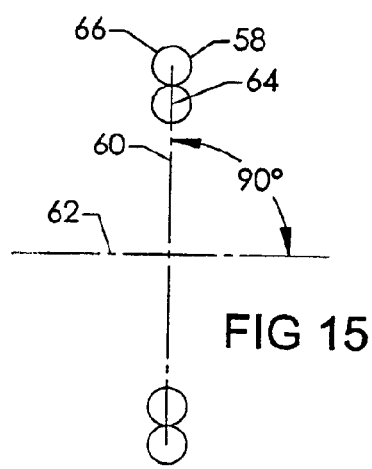
FIG. 15 shows a transverse cross sectional view of a surgical coil having a coil configuration similar to that of FIG. 12 illustrating an element axis of the surgical coil of about 90 degrees with respect to the coil axis.

FIGS. 12-14 show three different embodiments of surgical coils having element axes forming differing angles with respect to an axis of the respective surgical coils. FIG. 15 illustrates a transverse cross sectional view of the surgical coil 58 of FIG. 12 with an element axis 60 that forms an angle of about 90 degrees with an axis 62 of the surgical coil 58. The element axis line 60 is formed by a line extending through a longitudinal axis 64 of the elongate element 66 of the surgical coil 58 on each side of the section shown in FIG. 15. In FIG. 15, such a line 60 is shown making an angle of about 90 degrees with the coil axis 62.

Figure 16:
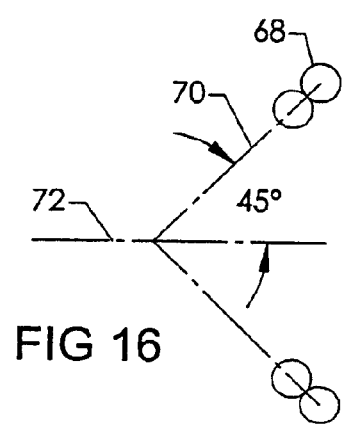
FIG. 16 shows a transverse cross sectional view of a surgical coil having a coil configuration similar to that of FIG. 13 illustrating an element axis of the surgical coil of about 45 degrees with respect to the coil axis.

FIG. 16 illustrates a transverse cross sectional view of the surgical coil 68 of FIG. 13 with an element axis 70 that forms an angle of about 45 degrees with an axis 72 of the surgical coil 68. Such a surgical coil 68 has a somewhat conical configuration overall. FIG. 14 shows a surgical coil 74 embodiment wound similar to a tightly wound coil spring having an element axis that is substantially parallel to an axis (not shown) of the coil 74, or put another way, forming a zero angle with an axis of the coil. Such a coil would have a substantially cylindrical configuration.

FIGS. 17-19 illustrate various embodiments of elongate elements of surgical coils in a straightened configuration. FIG. 17 shows an elongate element 76 having a wedge shaped trocar-like tissue cutting distal tip 78 and a wedge shaped recess 80 at a proximal end 82. FIG. 18 shows an elongate element 84 having a plurality of axially consecutive longitudinal slots 86 cut into the elongate element 84. Such slots 86 can be formed into one surface 88 of the elongate element 84, or may extend completely through the elongate element 84. Such slots or cavities 86 may be used to hold image contrast materials such as radiopaque materials or materials that can be readily imaged by ultrasonic imaging, MRI imaging or any other suitable imaging technique. The slots or cavities 86 could also be used to hold bioactive agents such as antibiotic agents, growth factors, anti-inflammatory agents and the like. The cavities 86 can have configurations other than the slots 86 shown, which are merely illustrative. The cavities 86 and any material disposed within them may also be covered with a gas or liquid permeable membrane (not shown) which may be used to regulate the rate of delivery or elution of the agents.

FIG. 20 is a transverse cross sectional view of the elongate element 76 of FIG. 19. The elongate element 76 has a major transverse dimension 90 and a minor transverse dimension 92 and has a substantially oval configuration overall, but with a somewhat flattened top surface 94 and bottom surface 96. In some embodiments of elongate elements 76, a length of the major transverse dimension 90 may be at least about 2 times a length of the minor transverse dimension 92, in other embodiments at least 3 times the length of the minor transverse dimension 92. In still other embodiments, the major transverse dimension of the elongate element 76 may have a length of about 2 to about 8 times the length of the minor transverse dimension 92, specifically, about 3 to about 6 time the length of the minor transverse dimension 92. FIGS. 21-23 illustrate transverse cross sections of other embodiments of elongate elements. FIG. 21 shows a transverse cross section of an elongate element 98 having a substantially round cross section, FIG. 22 illustrates an elongate element 100 with a substantially rectangular transverse cross section, and FIG. 23 illustrates a transverse cross section of an elongate element 102 similar to that of the elongate element 76 of FIG. 20, but with a longitudinal cavity or lumen 104 extending through the elongate element 102. The lumen 104 of elongate element 102 may be used as a cavity for image contrast materials or bioactive agents as discussed above and may have one or more openings (not shown) that may optionally be covered with permeable membranes (not shown).

Figure 23C:
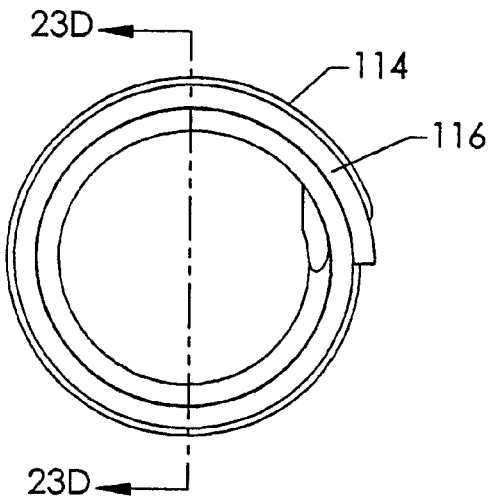
FIG. 23C is an elevational view of a surgical coil having an embodiment of an interlocking or self-aligning coil configuration.
Figure 23D:
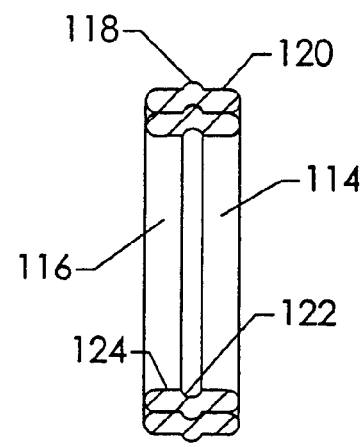
FIG. 23D is a transverse cross sectional view of the surgical coil of FIG. 23A taken along lines 23B-23B of FIG. 23A illustrating an interlocking groove and raised ridge on the elongate element of the surgical coil.

FIGS. 23A-23D illustrate two embodiments of surgical coils which have elongate elements that interlock when deployed. FIG. 23A shows a surgical coil 106 having approximately 360 degrees of circumferential overlap and a curved elongate element 108 with an interlocking cross sectional configuration. FIG. 23B is a transverse cross sectional view of the surgical coil 106 of FIG. 23A which illustrates the curved elongate element 108. The elongate element 108 has a concave inner surface 110 which interlocks laterally with a convex outer surface 112 when the inner surface 110 and outer surface 112 are in a tightly coiled configuration as shown in FIG. 23B. FIG. 23C illustrates an embodiment of a surgical coil 114 with an elongate element 116 having an interlocking configuration. FIG. 23D is a transverse cross sectional view of the surgical coil 114 of FIG. 23C which shows a raised ridge 118 extending longitudinally on a first surface 120 of the elongate element 116 which is configured to mate and interlock with a groove 122 extending longitudinally along a second surface 124 of the elongate element 116. An interlocking engagement between the raised ridge 118 and groove 122 can be seen in FIG. 23D where two adjacent overlapped portions of the elongate element 116 are in contact with each other.

Figure 24:
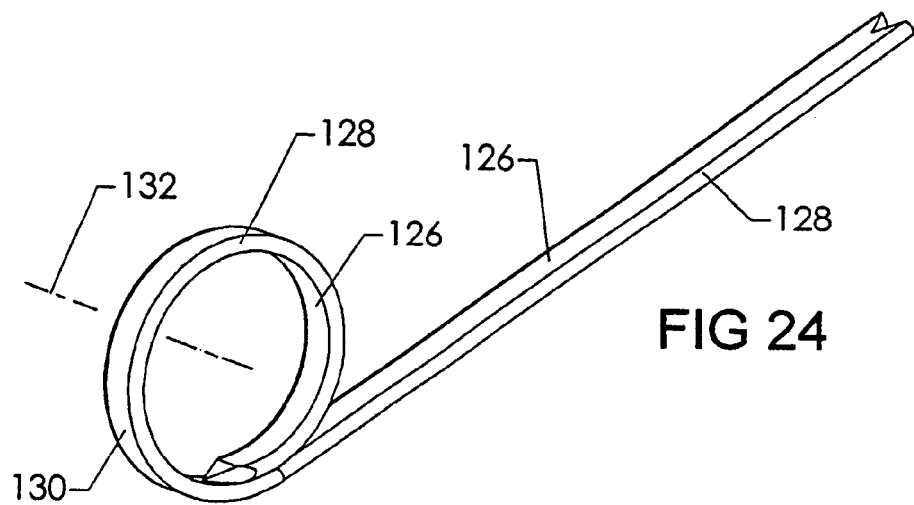
FIG. 24 is a perspective view of a surgical coil in a partially deployed state about the axis of the surgical coil with a proximal portion of the partially deployed coil in a straightened configuration.

FIG. 24 shows an elongate element 126 partially deployed and formed into a surgical coil 130 about an axis 132 of the surgical coil 130. A proximal portion of the elongate element 128 is in a substantially straightened configuration as may be the case inside a delivery sheath of a delivery system (not shown). In some embodiments, a series of elongate elements may be loaded into a delivery sheath which constrains the elongate elements 126 into a substantially straightened configuration for deployment.

Figure 2:
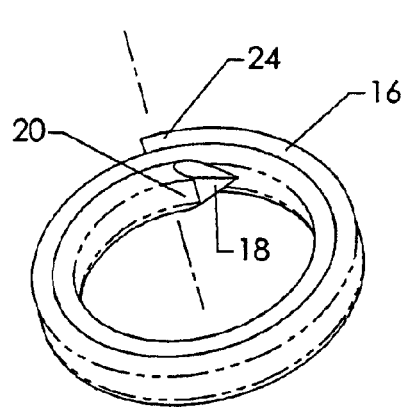
FIGS. 2 and 3 illustrate a perspective view of a surgical coil having features of the invention.
Figure 3:
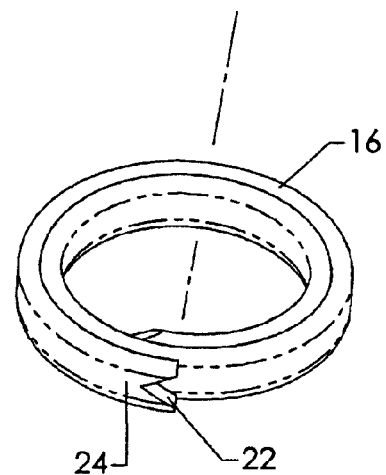

Surgical coils 10 intended for placement in tissue can be fabricated with a distal point to facilitate tissue penetration when the coil 10 is ejected or deployed from the delivery device. After deployment, embodiments of the surgical coil 10 assume a self-forming coiled shape. In doing so the surgical coil 10 creates full circumferential path through adjacent tissue that the coil 10 traps itself within. In a deployed configuration, both ends of an elongate element 16 of the surgical coil 10 can be in contact with each other in overlapped portions as shown in FIGS. 2 and 3. As such, movement of the surgical coil 10 is limited to rotation of the coil 10 about its own axis because the tissue captured within the axis of the surgical coil prevents tranlation of the surgical coil 10 through tissue.

In some applications surgical coils 10 are required to support a pulling force from another component to which it has been secured. Such other components may be referred to as attachments throughout this document. These attachments can include sutures and can be easily joined to the coil 10 as part of the surgical coil deployment process as discussed in more detail below.

Surgical coils 10 may be configured so that any pointed or sharp ends 18 do not protrude away from and are encased within the surgical coil 10. Surgical coils 10 with this feature are shown generally in FIGS. 2, 14, 23A and 23C. This feature can help to protect medical staff from accidentally sticking themselves on sharp edges when palpating a tissue mass having a surgical coil 10 disposed therein during or after surgical removal of the tissue mass. This feature also prevents the surgical coil 10 from opening up if it rotates by not allowing an end of an elongate element 16 of a surgical coil 10 to core another path and deviate from the original target site.

Surgical coils 10 can be made from a variety of materials including those that exhibit either great elasticity or shape memory properties. Suitable materials for fabrication include but are not limited to nickel titanium alloys (Nitinol), stainless steel, Elgiloy, MP35N or other high strength biocompatible materials. The cross section profile of the elongate element 16 of the surgical coils 10 illustrated in the embodiments of FIGS. 1-22 may be oval or round but can be any other suitable shape.

Various clinical applications or indications can require a specific surgical coil configuration. The number of rotations or amount of circumferential overlap that the surgical coil 10 will have can be dependant on whether or not it has to support any load, such as a tensile load, from an attachment, and, if so, the amount of load the surgical coil 10 is required to support and the strength of tissue surrounding the surgical coil 10.

Surgical coils 10 can vary significantly in the various dimensions and configurations, depending on the intended use. One embodiment of a surgical coil has 50 an outside diameter 134, see FIG. 8, from about 0.060" to about 0.300", and a transverse dimension of about 0.002" to about 0.040". The number coil rotations for one embodiment can range from about 1 to about 5, which corresponds to a circumferential overlap of about 0 to about 1,440 degrees. The circumferential overlap of surgical coil embodiments creates a complete circular structure that is enclosed an prevents attachments, such as sutures and marking devices from pulling out or slipping out of the ring-like structure of the surgical coils. Surgical coils having no circumferential overlap could allow attachments to slip or pull through the joint between ends of the structure is a force is applied to the attachment. In addition, the size and strength of a surgical coil can be dependent on the type of tissue within which it is being deployed. For example, in strong fibrous tissue, such as muscle or tendon, a small surgical coil can be used. However, for soft tissue deployment, a larger surgical coil which encompasses or encircles a larger amount of tissue may be necessary in order to adequately anchor or fix the surgical coil in the tissue.

In some embodiments, it is desirable that the inside diameter 135 of the surgical coil 50 (see FIG. 8) be as small as possible. The smaller the inside diameter 135 for a given surgical coil 50, generally the higher the pull or tensile force it can withstand before opening up or otherwise mechanically failing. In addition, pull force performance may be substantially increased by adding more revolutions of coiled material and increasing the overall coil thickness (stacking the coils). The surgical coil 56 configuration shown in FIG. 9 with an additional wind or 720° of circumferential overlap can have an increase in pull force performance of approx 50% in comparison to the configuration of the surgical coil 50 shown in FIG. 8.

Many variations of surgical coil wind geometries are are contemplated, as illustrated in FIGS. 12-14. In addition to variations in surgical coil wind geometries, embodiments are shown that add slots 86 to the surgical elongate element 84 as shown in FIG. 18 (the surgical coil is shown here flattened out to clearly show the slots) and or use a hollow structure, a cross section of which is illustrated in FIG. 23. These slotted or hollow features could be used as reservoirs for drugs and the surgical coil used for site-specific drug delivery. The slots 86 shown in FIG. 18 may also make the device more visible with ultrasound imaging systems and the like. The surgical coil 10 embodiments of FIGS. 1-11 have a "V" groove at the proximal end of the surgical coils 10 which may be used for embodiments of delivery methods.

Surgical coils 10 may be used as tissue markers with a small dimensional configuration. One embodiment of a surgical coil marker 42 can have an outer diameter of about 0.060" to about 0.100". In addition, if a surgical 42 coil is to be used as a marker and will not be subjected to significant stresses, the surgical coil marker can have a low number of coil rotations or small to non-existant amount of circumferential overlap. Surgical coil markers 42 used to identify specific target areas within tissue are generally not required to carry any load and need only to be large enough to be detected by suitable medical imaging devices. Surgical coils 10 used as soft tissue or bone anchors may be larger than surgical coil markers, with some embodiments having an outer diameter of about 0.100" to about 0.300". Such surgical coils can have 2 or more coil rotations, i.e., 360 degrees or more of circumferential overlap, and can be attached to a second component or attachment member if desired. Such a surgical coil anchor may be used to anchor itself at a specific target tissue area and support the joined attachment.

Surgical coils 10 used for suturing and stapling applications may have a wide range of dimensions and configurations. Such embodiments may have to keep a wound closed so circumferential overlap is required to support the load between two sections of tissue being held together. The outer diameter of some embodiments can be from about 0.06 inch to about 0.30 inch. Circumferential overlap of at least about 90 degrees may be suitable for these applications. A surgical coil 10 for these indications may perform both the function of suturing and stapling, and so, can be considered a hybrid device. Metallic suture materials are often desirable in applications where a permanent suture is required because they generally produce low tissue reactivity. However, metallic sutures are rarely used due to difficulty in tying reliable knots and cutting the metallic material. A surgical coil 10 used for suturing eliminates the need to tie a knot or cut the material and provides full circular fixation of tissue within the surgical coil.

Figure 25:
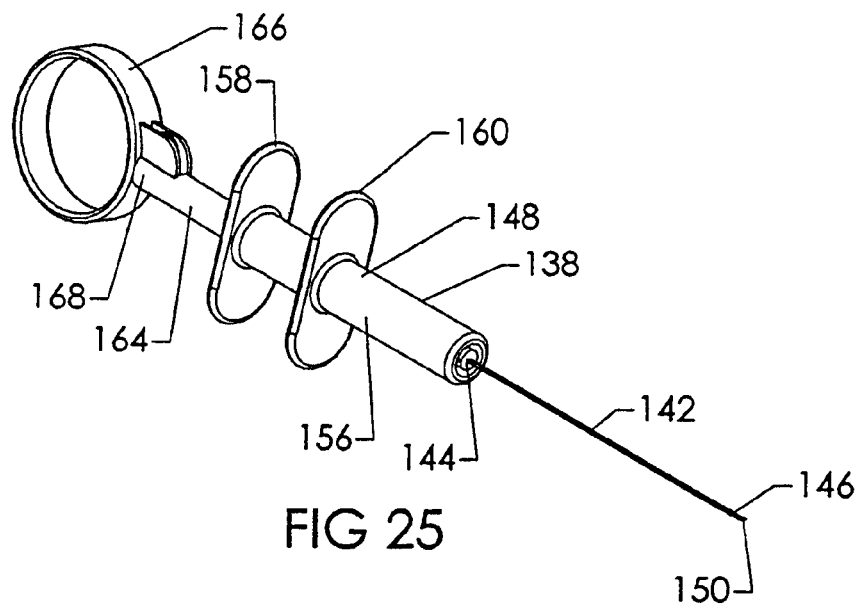
FIG. 25 is a perspective view of a ratcheting delivery device configured to deliver and deploy surgical coils, with a thumb ring of the delivery device in a proximal retracted position.

FIGS. 25-45 illustrate an embodiment of a delivery device 138 and methods of using the delivery device 138 for deployment of surgical coils 140. FIG. 25 is a perspective view of an embodiment of a delivery device 138 having an elongate delivery sheath 142 with a proximal end 144 a distal end and a delivery actuator 148 secured to the proximal end 144 of the delivery sheath 142. As shown in FIG. 34A, an embodiment of the delivery sheath can have a sharpened distal end with an angle indicated by arrow 143, of about 15 to about 30 degrees. The delivery sheath is an elongate hollow tube having a sharpened distal tip 150 shown in FIG. 27. The delivery sheath 142 has an interior lumen 152, shown in FIG. 34, which is configured to constrain an elongate element 154 of a surgical coil 140 and allow the constrained elongate element 154 to be advanced through the lumen 152 of the delivery sheath 142 to a deployment site. For the configuration shown, the delivery sheath 142 can be made from any suitable high strength metal, composite or polymer.

Suitable metals include stainless steel, Nitinol, MP35N and the like. The delivery actuator 148 has an elongate cylindrically shaped body portion 156 with a proximal flange 158 and a distal flange 160. The body portion 156 has an internal bore 162 that is sized to accept a cylindrical actuator 164 in sliding relation to the body portion 156. A thumb ring 166 is disposed at a proximal end 168 of the cylindrical actuator 164 to facilitate the grip of an operator of the delivery device 138. The body portion 156 and cylindrical actuator 164 can be made from a variety of suitable medical grade materials, including metals, composites and polymers. Specifically, polymers such as ABS plastic, PVC, polycarbonate and the like may be used.

Figure 32:
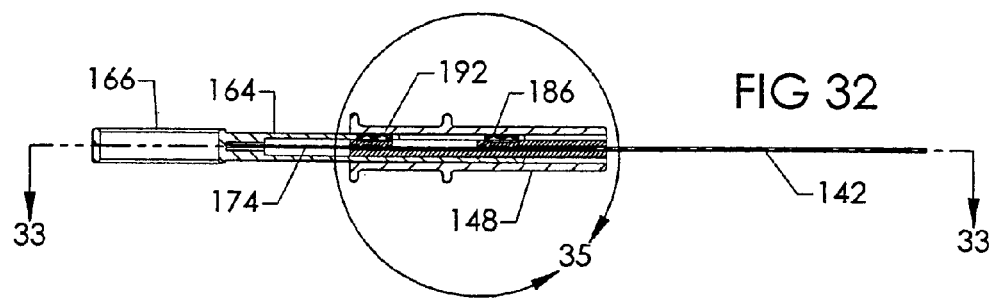
FIG. 32 is an elevational view in partial section of the delivery device of FIG. 31 taken along lines 32-32 of FIG. 31.
Figure 33:
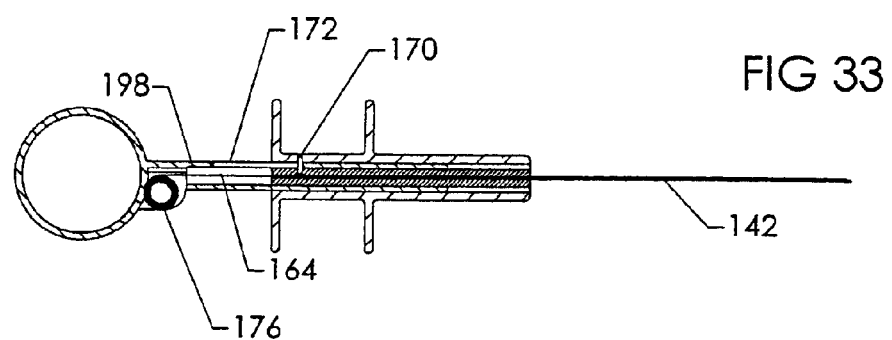
FIG. 33 is a top view in partial section of the delivery device of FIG. 32 taken along lines 33-33 of FIG. 32.
Figure 35:
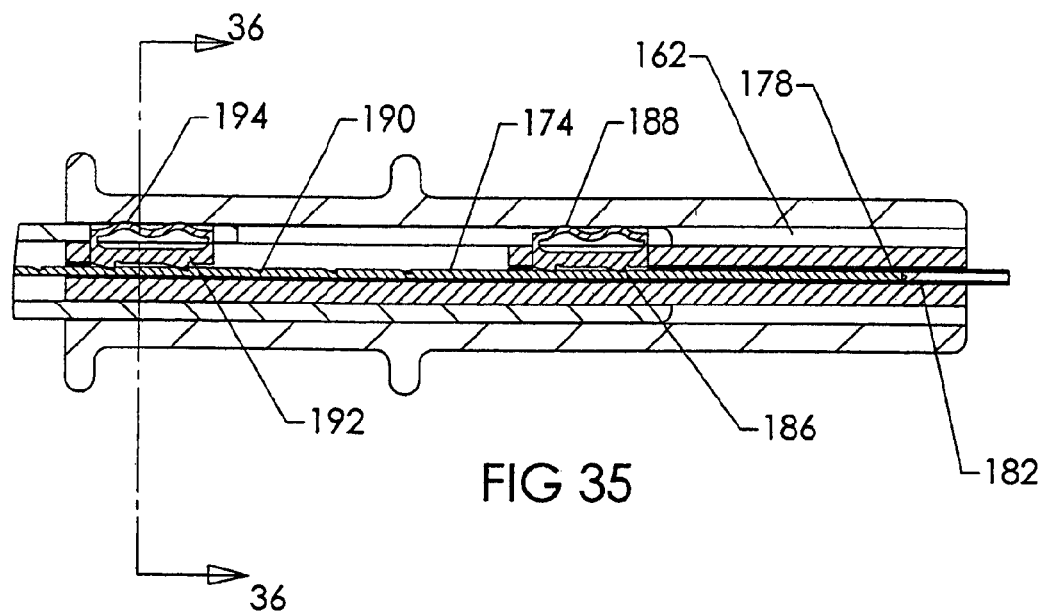
FIG. 35 is an enlarged elevational view in section of the encircled portion 35 of FIG. 32 showing the delivery device.
Figure 36:
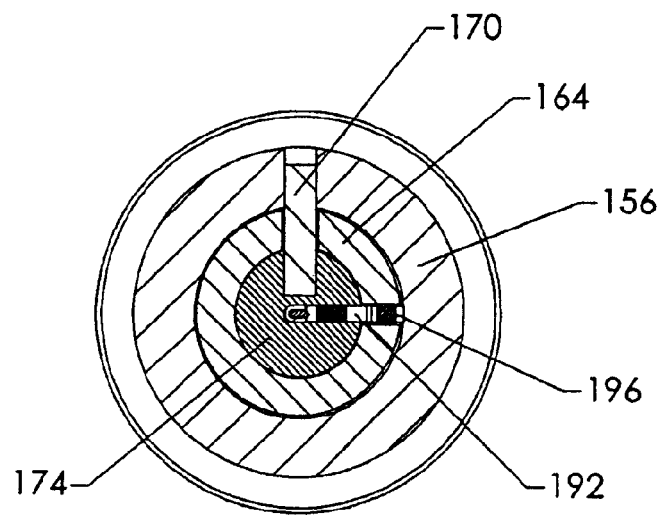
FIG. 36 is a transverse cross sectional view of the delivery device of FIG. 35 taken along lines 36-36 of FIG. 35.
Figure 40:
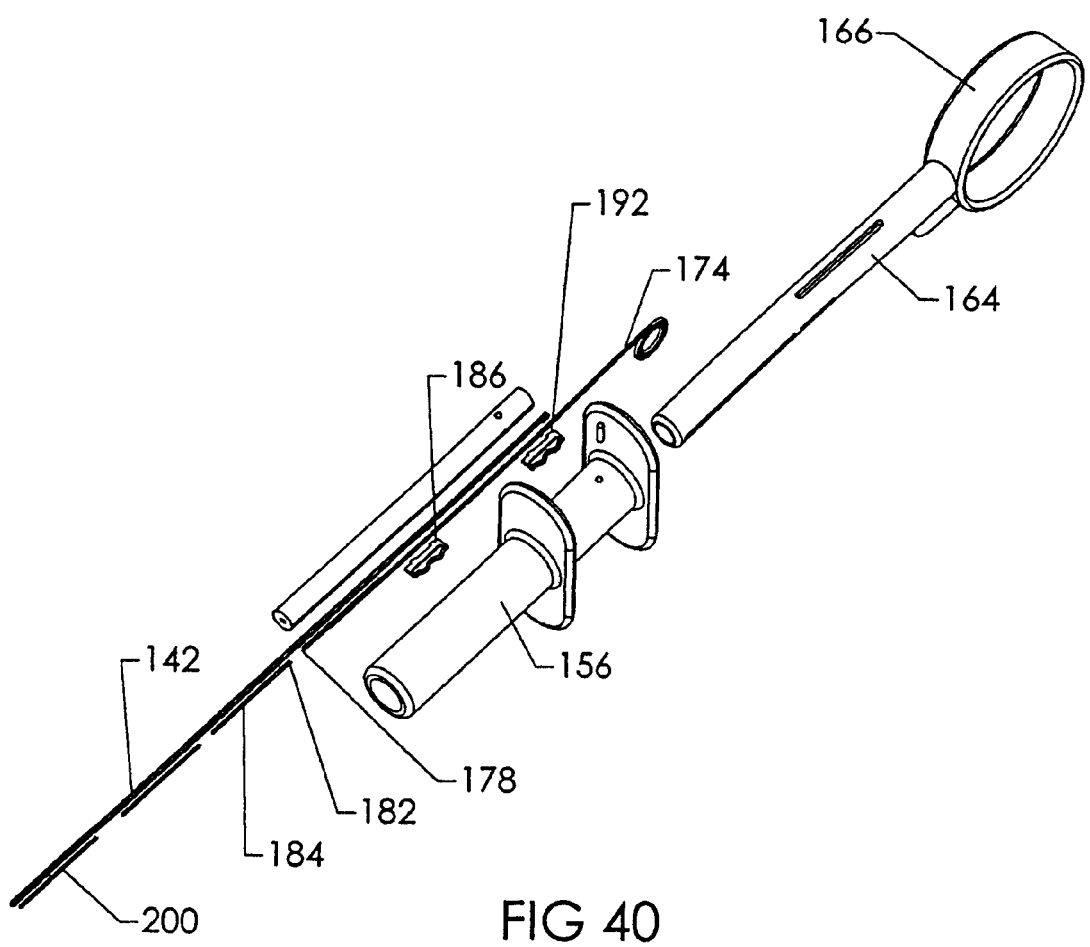
FIG. 40 is an exploded view of the delivery device of FIG. 25.

Referring to FIG. 33, a limit pin 170 is secured to the body portion 156 and slidingly engages a slot 172 in the cylindrical actuator 164 that is configured to limit the relative travel between the cylindrical actuator 164 and the body portion 156. An advancing ribbon 174 is coiled in a compartment 176 adjacent the thumb ring 166 and has a distal end 178 which extends into a proximal end 180 of the delivery sheath 142 and contacts a proximal end 182 of an elongate element 184 disposed in the delivery sheath 142 ready for deployment, as shown in FIG. 40. Referring to FIGS. 32 and 35, a first or distal ratchet member 186 having a bias member, such as spring 188, is fixed relative to the body portion 156 with regard to relative axial movement and is configured to translate in a radial direction under force of the spring 188 in order for the first ratchet member 186 to releasably engage the advancing ribbon 174 and prevent proximal translation of the advancing ribbon 174. The advancing ribbon 174 has a series of notches 190 which are configured to releasably engage the first ratchet member 186. A second ratchet member 192 having a bias member, such as spring 194, is disposed on the cylindrical actuator 164 proximally of the first ratchet member 186. The second ratchet member 192 is configured to engage the advancing ribbon 174 similarly to the first ratchet member 186 and moves axially with the cylindrical actuator 165 while the slot 196 within which the second ratchet member 192 is disposed allows radial motion.

Figure 42:
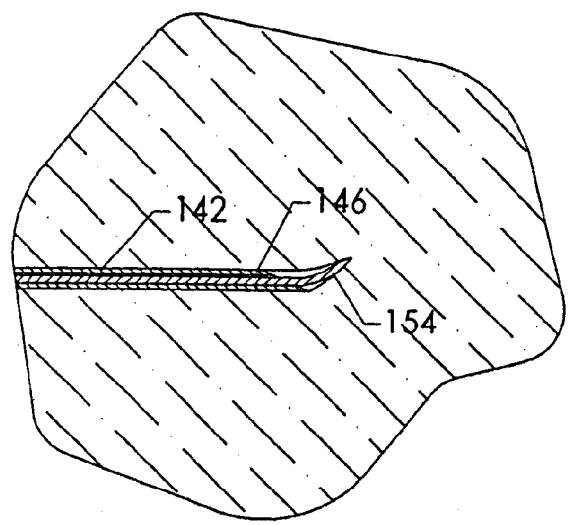
FIG. 42 illustrates a sharpened distal tip of a surgical coil penetrating tissue during deployment.
Figure 43:
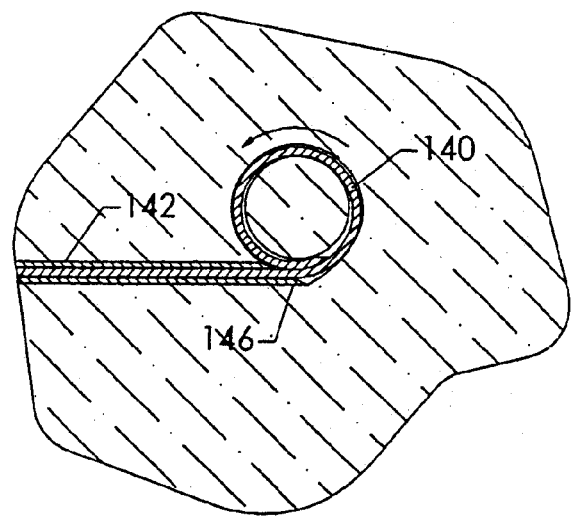
FIG. 43 illustrates a schematic view of the surgical coil of FIG. 42 in a further deployed configuration, the direction of deployment being indicated by the arrow.
Figure 44:
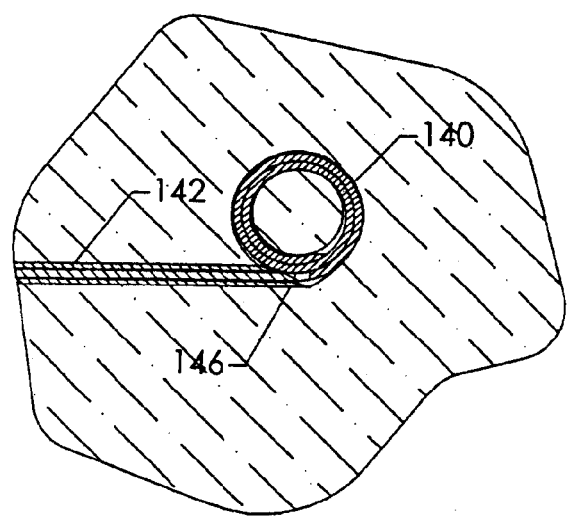
FIG. 44 illustrates a schematic view of the surgical coil in a completely deployed state within tissue.

When the cylindrical actuator 164 is advanced distally, the second ratchet member 192 engages one of the notches 190 in the advancing ribbon 174 and translates the advancing ribbon 174 forward in a distal direction until the limit pin 170 engages a proximal end 198 of the limit slot 172 of the cylindrical actuator 164. At this point, the first ratchet member 186 engages another notch 190 in the advancing ribbon 174 and prevents proximal translation of the advancing ribbon 174. Referring to FIG. 40, during the distal advancement of the advancing ribbon 174, the distal end 178 of the advancing ribbon 174 pushes against a proximal end 182 of the proximal most elongate element 184 loaded within the lumen 152 of the delivery sheath 142 and advances the proximal most elongate element 184 which then translates the distal motion to a distal most elongate element 200. The distal translation movement deploys the distal most elongate element 200 during the advancement cycle as shown in FIGS. 42-44. Thereafter, the cylindrical actuator 164 can then be proximally retracted and the delivery device 138 is then ready to begin another surgical coil deployment cycle.

For the delivery device 138, a feature to enable elongate elements 184 to be deployed that may be important is the ability of elongate elements 184 to push against each other axially without compromising the sharp distal tip of the elongate element 184 pushing on an elongate element ahead of it. In FIG. 39, a first elongate 202 element has a distal tip 204 engaged with a proximal end 206 of a second elongate element 208. In the embodiments shown, a wedge shaped recess 210 of the second elongate element 208 has a wedge recess angle that is less than a wedge angle of the sharpened distal tip 204 of the first elongate element 202. Such a configuration serves to protect the sharpened distal tip 204 of the first elongate element 202 from being dulled due to contact with the proximal end 206 of the second elongate element 208. The amount of force to move an elongate element through a delivery sheath can be significant because of the frictional force generated by the elongate element pushing against the constraining force of the delivery sheath.

Figures 41, 41A:
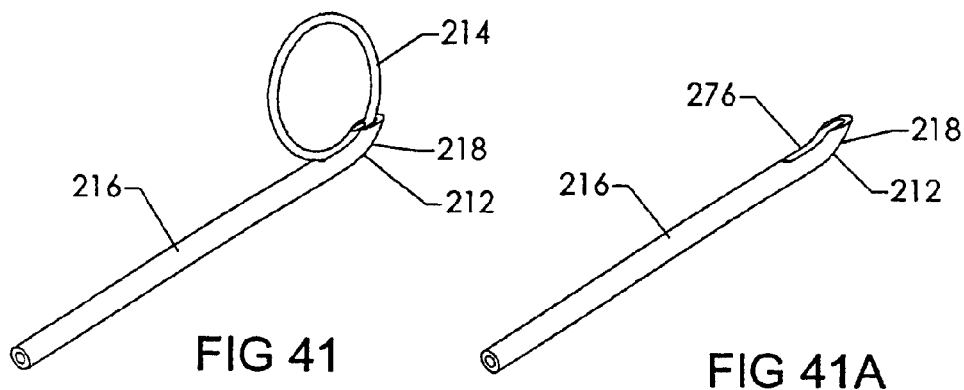
FIG. 41 is a perspective view of a distal section of a delivery sheath of a delivery device and a surgical coil being formed by a coil forming member at the distal end of the delivery sheath the delivery sheath also having a directional capability that is suitable for directing the deployment direction of a surgical coil having a transverse cross sectional configuration which is substantially round.
FIG. 41A is a perspective view of the distal section of the delivery sheath of FIG. 41 with the surgical coil not shown for clarity of illustration.
Figure 41B:
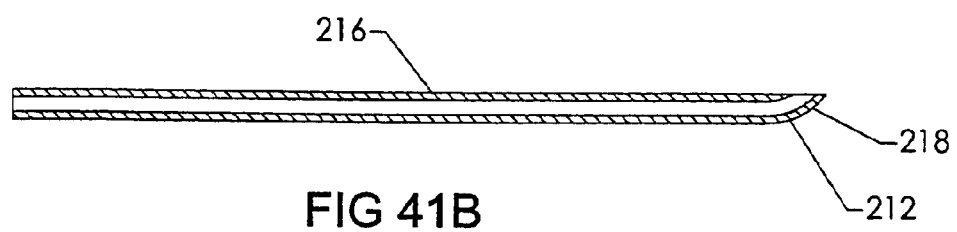
FIG. 41B is an elevational view in section of the delivery sheath of FIG. 41A.
Figure 41C:
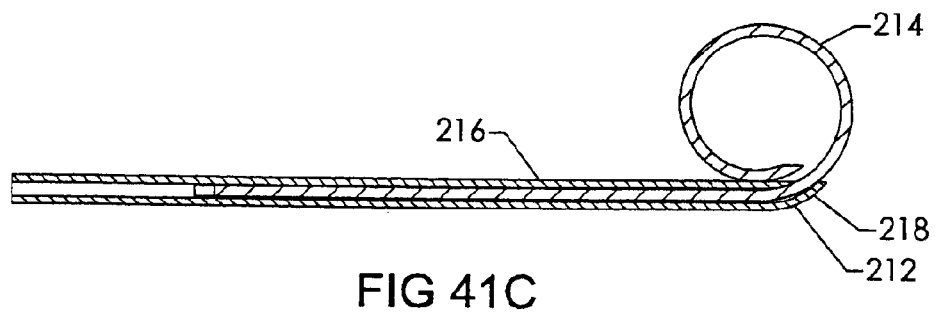
FIG. 41C is an elevational view in section of a delivery sheath forming a surgical coil from an elongate element during deployment of the surgical coil.

A surgical coil 140 being deployed from a distal end 146 of the delivery sheath 142 as shown in FIGS. 42-44 can be a self-forming member, wherein the elongate element 154 returns to a coiled configuration, that is the configuration in a relaxed state, as the elongate element 154 exits the distal end 146 of the delivery sheath 142 and the constraint of the delivery sheath 142 is removed. Alternatively, the distal end 146 of the delivery sheath 142 may include, or be disposed adjacent, a coil forming member 212 which strains an elongate element into a coiled configuration as it is deployed through the delivery sheath 142, as can be seen in FIGS. 41B-41C. In this embodiment, an elongate element 214 has a substantially straight or non-coiled configuration in a relaxed state without any constraints thereon. As the elongate element 214 is pushed out of the delivery sheath 216, it passes through or by a coil forming member 212 which permanently strains the material of the elongate element 214 which then assumes a coiled configuration outside the delivery sheath 216 as shown in FIG. 41C. For the embodiment of FIGS. 41-41C, the coil forming member 212 is a bent portion of a distal section 218 of the delivery sheath 216, however, any other suitable arrangement could be used. The coil forming member 212 can also serve to add directional capability that is suitable for directing the deployment direction of a surgical coil having a transverse cross sectional configuration which is substantially round.

Figure 45:
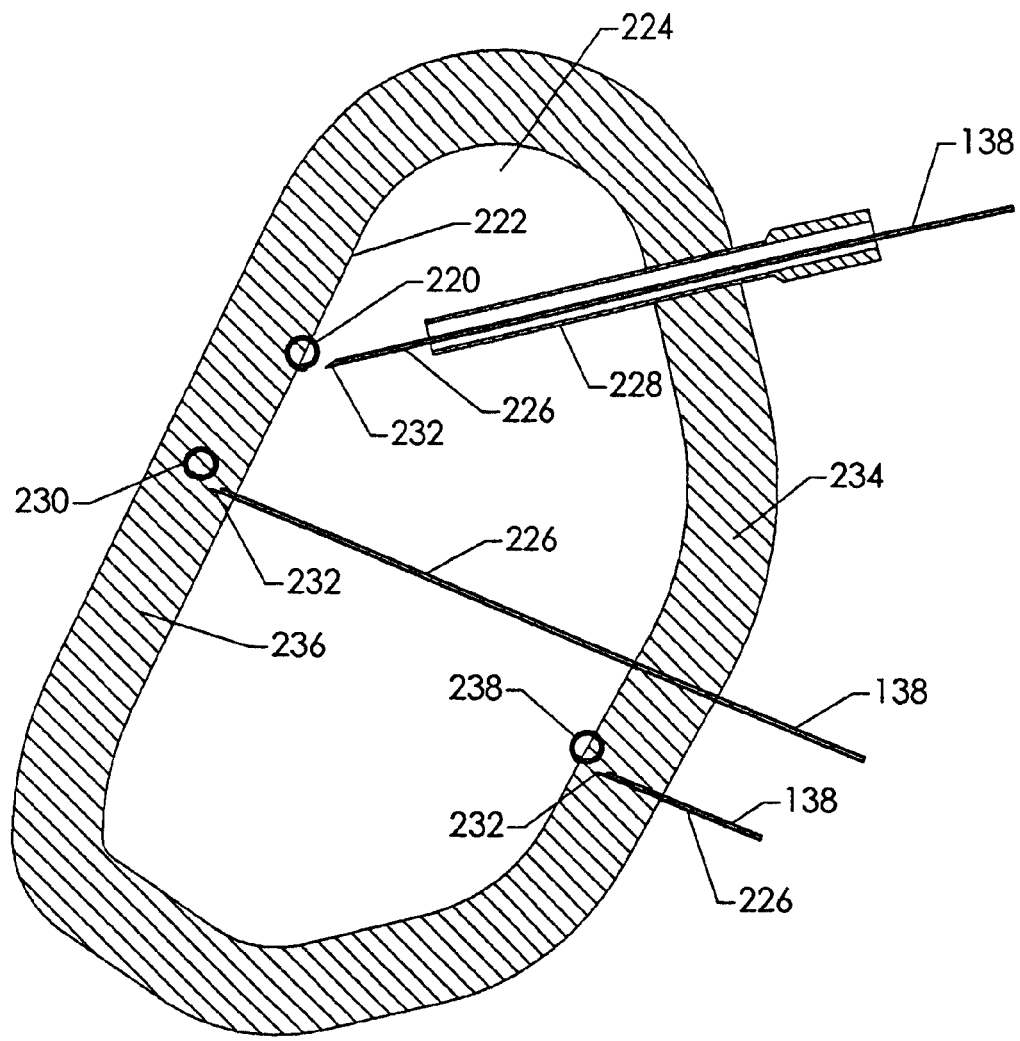
FIG. 45 shows three surgical coils deployed in a variety of deployment configurations by a variety of deployment methods with respect to tissue surfaces.
Figure 48:
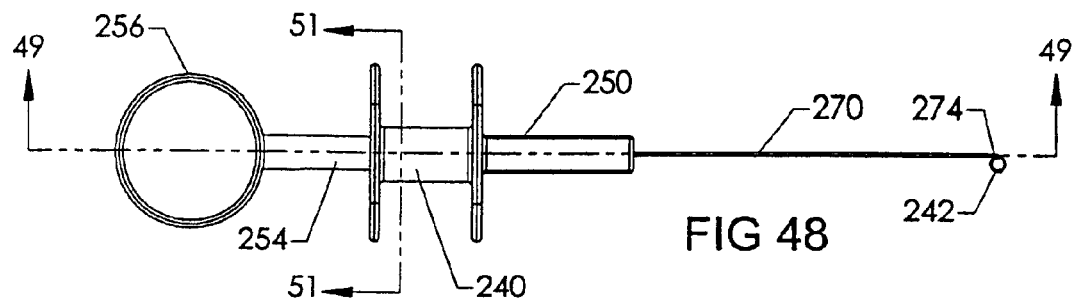
FIG. 48 is an elevational view of the delivery device of FIG. 46.
Figure 49:
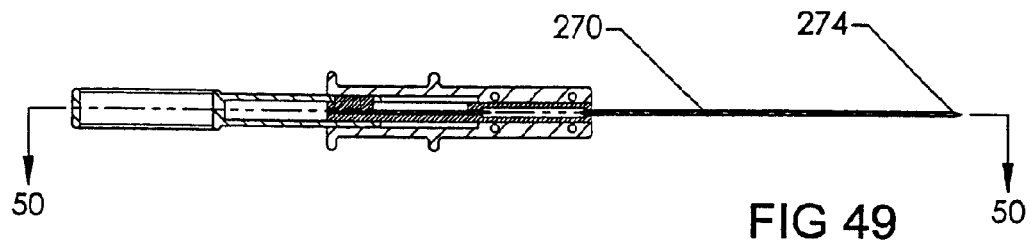
FIG. 49 is a top view in partial section of the delivery device of FIG. 48 taken along lines 49-49 of FIG. 48.
Figure 50:
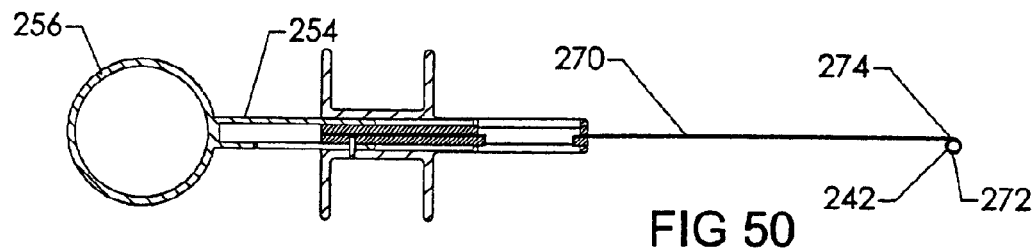
FIG. 50 is an elevational view in partial section of the delivery device of FIG. 49 taken along lines 50-50 in FIG. 49.
Figure 51:
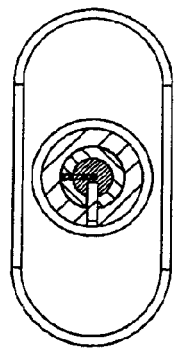
FIG. 51 is a transverse cross sectional view of the delivery device of FIG. 48 taken along lines 51-51 of FIG. 48.
Figure 56:
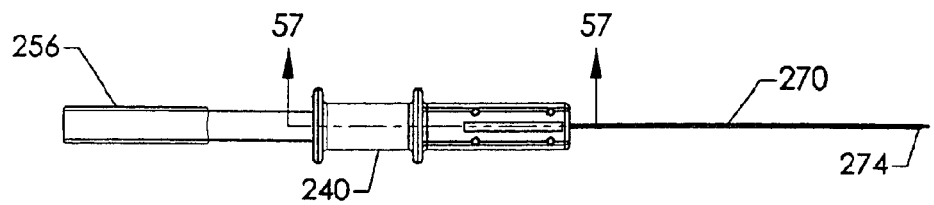
FIG. 56 is a top view of the delivery device shown in FIG. 46.

FIG. 45 illustrates a variety of deployment methods and configurations that could be used with the delivery device 138 and similar devices discussed herein. The delivery device 138 has the capability to serially deliver a plurality of surgical coils in a variety of configurations with respect to a tissue surface. A surgical coil 220 is shown deployed in an inner surface 222 of a patient's chest cavity 224 with a portion of the surgical coil 220 exposed. The surgical coil 220 has been delivered by a delivery sheath 226 introduced through a cannula member 228. Another surgical coil 230 is shown disposed beneath the inner surface 222 of the chest cavity 224 with no portion of the surgical coil 230 exposed. The surgical coil 230 having been deployed by a delivery sheath 226 having a sharpened tissue penetrating distal tip 232 which has penetrated an anterior wall 234 of the chest cavity 224 and been advanced into and beneath the inner surface 222 of a posterior wall 236 of the chest cavity 224. Finally, another surgical coil 238 has been deployed in the anterior wall 234 of the chest cavity 224 by inserting a sharpened delivery sheath 226 through the anterior chest wall portion 234 and deploying the surgical coil 238 from within the chest wall. A portion of the surgical coil is exposed above the inner surface 222 of the chest cavity 224.

Figure 34:
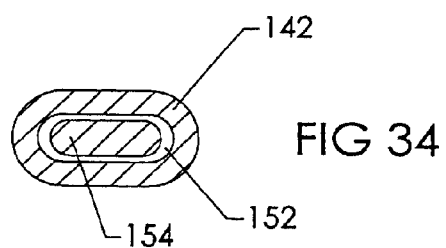
FIG. 34 is a transverse cross sectional view of the elongate member of the surgical coil and the delivery sheath of the delivery device of FIG. 32 taken along lines 34-34 of FIG. 32.
Figure 34A:
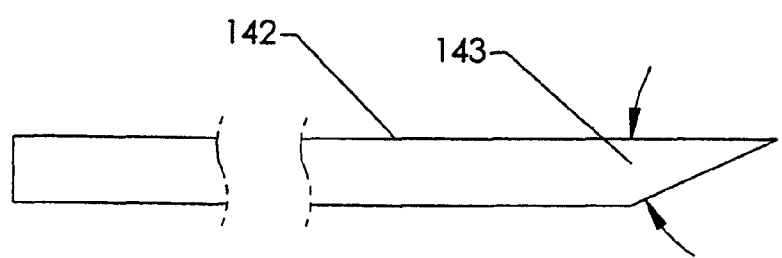
FIG. 34A illustrates the distal end of a delivery sheath with an arrow indicating the angle of the sharpened distal end of the delivery sheath.

Embodiments of delivery devices 138 and 240 shown in FIGS. 25 and 46 may use low profile delivery sheaths in the form of hollow needles with sharpened distal ends to deliver surgical coils to the target site. The delivery sheath 142 is a straight tube with a distal tissue penetrating point 150, as shown in FIG. 29, and is stiffer than a surgical coil 140 to be delivered therethrough. The geometry of the distal point of the delivery sheath 142 can be important in some embodiments. The distal point 150 needs to easily penetrate tissue while also providing clearance for the surgical coil 140 as it is being delivered without substantial restriction to assume the relaxed geometry of the surgical coil 140. For some delivery sheath 142 embodiments, the distal point can have an angle of about 25 degrees. As seen in FIG. 34A and the discussion thereof, other angles can also be used. Delivery sheaths 142 may have an internal profile that can slidably receive an elongate element 154 of surgical coils 140 along their full length, as shown in FIG. 34, and will straighten them out into a substantially straight configuration in doing so. Surgical coils 140 can be pre-loaded into the delivery sheath 142 prior to use. The maximum number of surgical coils 140 that a delivery sheath 142 can accommodate is limited by its length, however, some applications may require only a single surgical coil 140 be used. In a delivery device 138 having a multiple coil 140 configuration, surgical coils 140 can be stacked end to end within the delivery sheath 142. A surgical coil 140 configuration to preserve a sharpness of a tissue penetrating point of an elongate element 154 of a surgical coil 140 from damage by a proximal end of an adjacent elongate element of a surgical coil 140 is shown in FIGS. 38 and 39.

The delivery device 138 configuration shown in FIGS. 33-40 uses a ratchet system with a moving ratchet member 192 and a fixed spring ratchet member 186. When the thumb ring 186 is moved distally the moving ratchet teeth (FIG. 35) grip in the notches 190 of the advancing ribbon and move it also. The fixed spring ratchet 186 at this time slides up and over the notches 190 of the advancing ribbon 174 (the wave profile spring compresses to facilitate this). When the thumb ring 166 is returned to the proximal position the moving ratchet 192 slides over the advancing ribbon 174 while the fixed spring ratchet 186 stops any motion of the advancing ribbon 174. The distance of travel of the thumb ring 166 equals the length of a surgical coil 140 so that each time the thumb ring 166 is fully depressed a surgical coil 140 is ejected from the device 138. The advancing ribbon 174 has a profile that is slidably fits the sheath 142 and can be advanced the full length of the delivery sheath 142.

Figure 26:
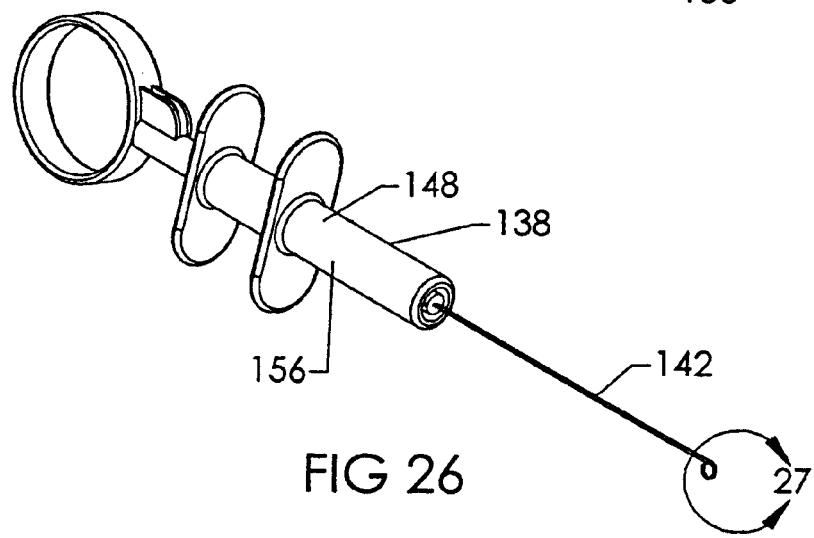
FIG. 26 is a perspective view of the delivery device of FIG. 25 with the thumb ring of the delivery device in an advanced distal position with a surgical coil being deployed from a distal end of a delivery sheath of the delivery device.
Figure 27:
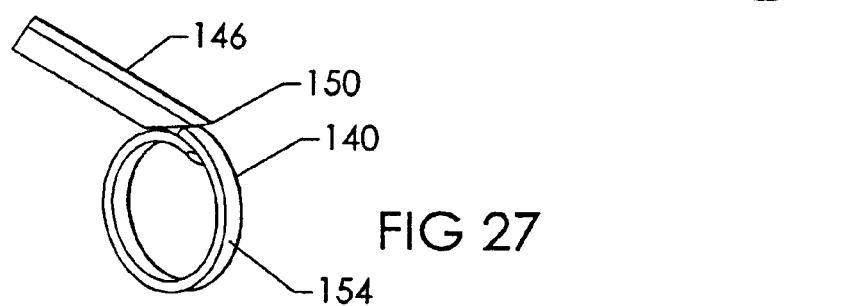
FIG. 27 is an enlarged view, in perspective, of the encircled portion 27 of FIG. 26 showing a distal section of the delivery device.
Figure 31:
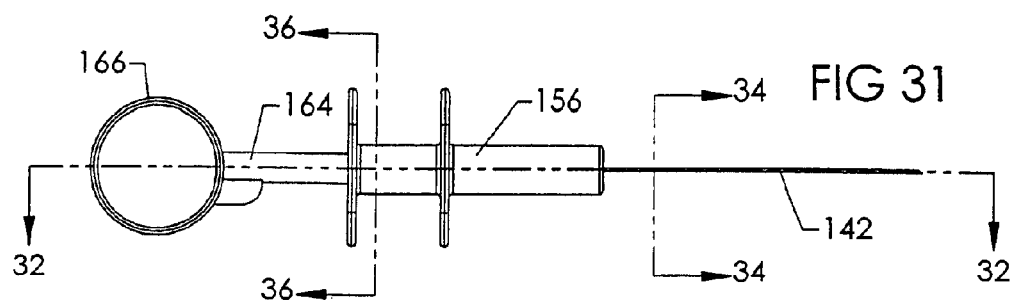
FIG. 31 is an elevational view of the delivery device of FIG. 25.

In one embodiment of use, the distal end 146 of the delivery sheath 142 is placed at a target site, a thumb ring 166 of the cylindrical actuator 164 is then moved distally as shown in FIG. 26 which pushes an advancing ribbon 174 (see FIGS. 35 and 57) which in turn pushes the most proximal surgical coil 174 which then ejects the most distal surgical coil 200 a from the device 138 as shown in FIG. 27. Drawings of two configurations of this device 138 and 240 are provided. FIGS. 33-40 show a configuration that will eject or deploy only the number of surgical coils 140 that are pre-loaded into the delivery sheath 142. FIGS. 46-57 show a configuration that houses surgical coils 242 in a cassette 244 and therefore the number of coils 242 can be delivered is limited only by the number of coils 242 the cassette 244 can accommodate.

Figure 58:
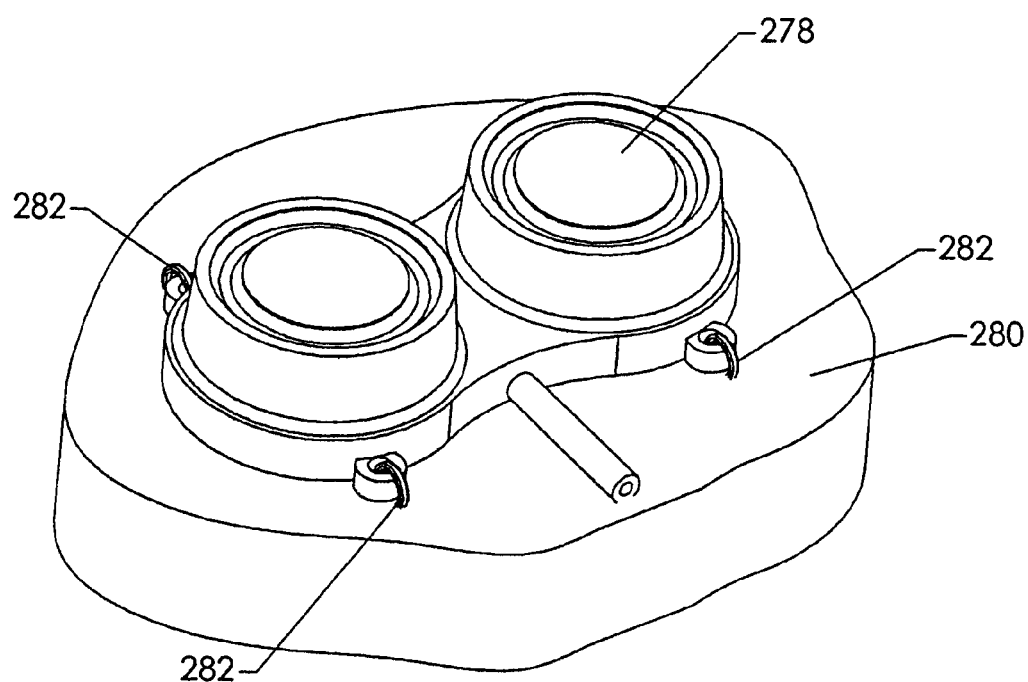
FIG. 58 is a perspective view of a vascular access port secured to chest muscle tissue by 4 surgical coils.

There are varieties of techniques that can be employed with these low profile delivery devices 138 and 240 to access target sites. The delivery sheath 142 can be used in the same manner as a hypodermic needle is for drug delivery (direct incision). Alternatively they can be placed within the working channel of an endoscope or cannula. All methods allow the physician to completely or partially implant a coil in tissue at an anterior or posterior location. Some illustrations of delivery techniques are shown in FIG. 45. Fully implanted coils 230 are typically used for tissue marking or site specific drug delivery with drug coated or impregnated coils 220 and 238, partially implanted coils can be used to attach suture lines for procedures such as bladder neck suspension or to create a group of purse string sutures. Coils can be delivered so that they interlock in linear or radial patterns to create palpable masses or linked as group for strong tissue anchor point. Embodiments can also be used to suture in place devices or components such as pacemakers, pacemaker leads, catheters or tissue supporting surgical materials such as Gore-Tex or hernia patch materials. An example of this use is illustrated in FIG. 58.

Figure 57:
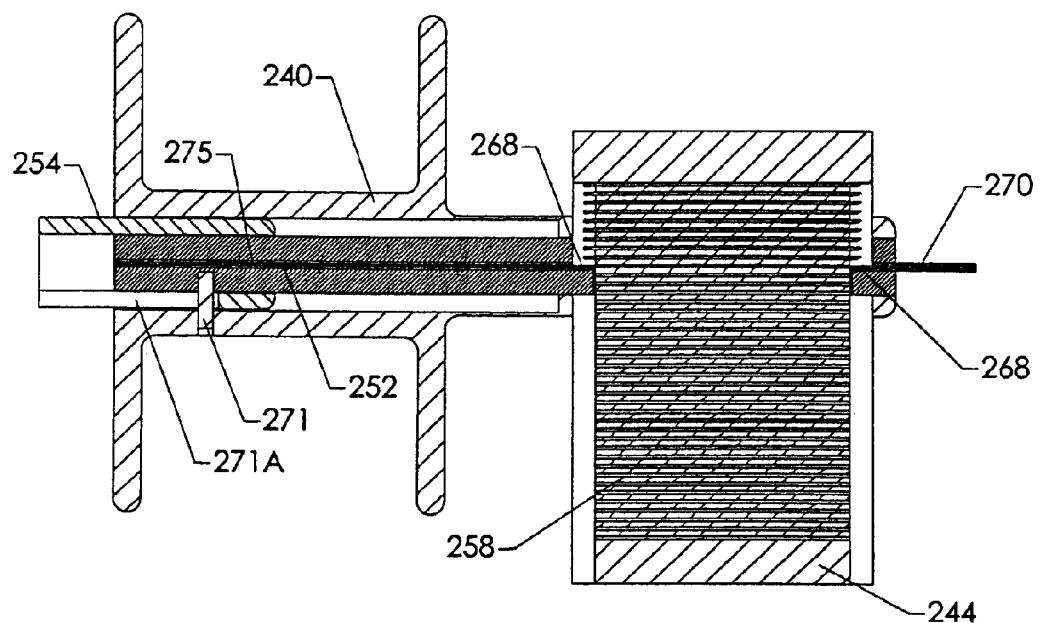
FIG. 57 is an enlarged elevational view of the delivery device of FIG. 56 taken along lines 57-57 in FIG. 56.
Figure 57A:
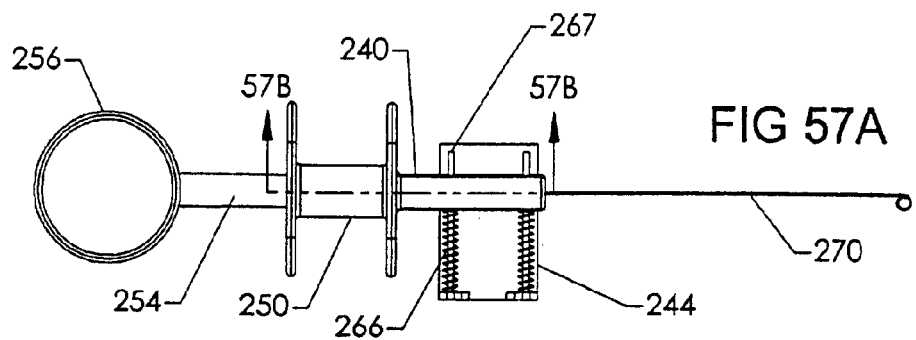
FIG. 57A is an elevational view of the delivery device of FIG. 46 with the cassette inserted into the cassette slot.
Figure 57B:
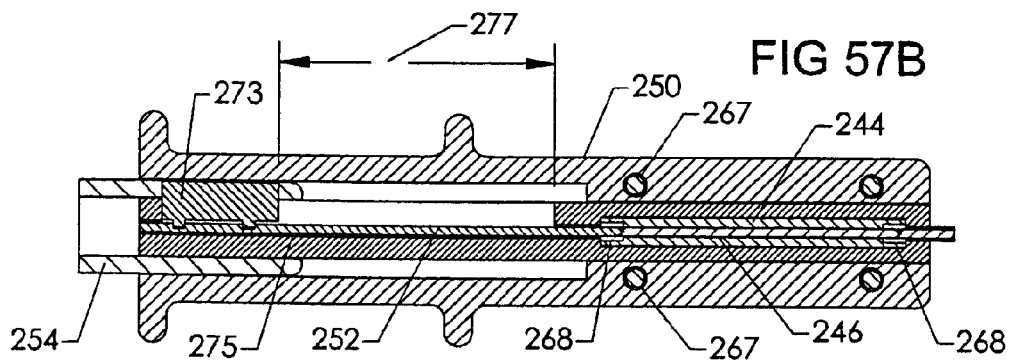
FIG. 57B is an enlarged view in section of the delivery device of FIG. 57A taken along lines 57B-57B of FIG. 57A.
Figure 57C:
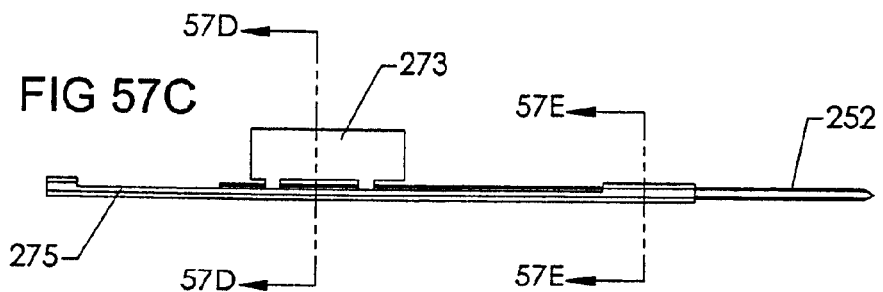
FIG. 57C is a botton view of an advancing ribbon guide, and elonagate element within the guide, of FIG. 58B without the structure surrounding the guide shown for clarity of illustration.
Figure 57D:
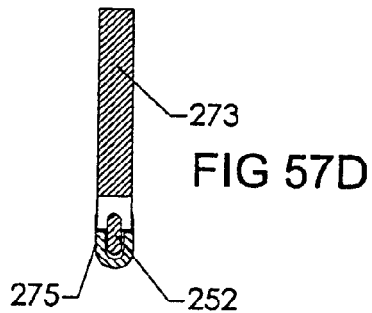
FIG. 57D is a transverse cross sectional view of the advancing ribbon guide of FIG. 57C taken along lines 57D-57D of FIG. 57C.
Figure 57E:
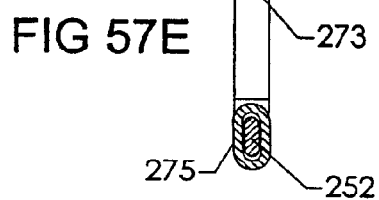
FIG. 57E is a transverse cross sectional view of the advancing ribbon guide of FIG. 57C taken along lines 57E-57E of FIG. 57C.

The delivery device 240 configuration shown in FIGS. 46-57 uses a surgical coil cassette 244 to store a plurality of elongate elements 246 of surgical coils 242. The surgical coil cassette 244 fits into a slot 248 in the delivery actuator 250, as shown in FIG. 47. An advancing ribbon 252 is slidingly disposed within an advancing ribbon guide 275. An advancing shuttle 273 is coupled to a cylindrical actuator 254 with the thumb ring 256 and moves in direct relationship with it. The cassette 244 has multiple slots 258 that accommodate surgical coils 242. The coils 242 are positioned so that the distal end 260 and proximal ends 262 extend into the side grooves 264 of the cassette 244 as shown in FIGS. 54, 55, and 57. Springs 266 shown in FIG. 46, surround spring posts 267 and are in compression and bias the cassette 244 away from the delivery actuator 250, in doing so the ends of the surgical coil 242 are forced to contact the stops 268, as shown in FIG. 57, and in alignment with the lumen of the delivery sheath 270 and advancing ribbon 252. When the thumb ring 256 is moved distally, the cylindrical actuator 254 is advanced distally which in turn advances an advancing shuttle 273. The axial motion of the cylindrical actuator 254 is limited by a limit pin 271 which is secured to the delivery actuator and and engages a slot 271A in the cylindrical actuator. The advancing shuttle, the axial movement of which is shown by arrow 277, engages a slot or slots in the advancing ribbon 252, as shown in FIGS. 57C-57D, and pushes a surgical coil 272 out of the cassette 244 and into the delivery sheath 270. When the thumb rings 256 is returned to the proximal position and the advancing ribbon 252 has been pulled out of the cassette 244 another surgical coil will be brought into contact with the stops 268. This procedure is repeated until the first coil 242 that was pushed out of the cassette 244 is aligned with the distal tip 274 of the delivery sheath 270. The device 240 can then be used to deliver surgical coils 242 to the target site and each full depression of the thumb ring 256 will eject a surgical coil 242.

The drawings shown illustrate an oval cross section of the surgical coils 242 and delivery sheath 270 however, surgical coils 242 made from materials with a round cross-sections that are deployed via a round cross-sections delivery needles can also be used. Surgical coils 242 having a circular cross-section have the disadvantage in that they are not self aligning, however an alignment feature can be provided to ensure that as the surgical coil it is deployed from the delivery sheath 270, it is correctly orientated. If a self-coring tip (also known as hubber tip as shown in FIG. 41) or slots 276 are provided longitudinally along the axis at the distal end of the delivery sheath the coil when it contacts this alignment feature 276 will take the path of least resistance and orient itself.

Delivery devices can be configured to deliver a plurality of surgical coils 10 simultaneously and in a variety of deployment patterns or configurations. Examples can include radial, linear, radial interlocking, linear interlocking, back to back in the same delivery tube, i.e., 2 surgical coils deployed together in opposite directions or back to front in the same delivery sheath, i.e., 2 coils deployed together in the same direction.

In one modality of deployment, FIG. 58 shows a vascular access port 278 secured to a portion of chest muscle 280 by four deployed surgical coils 282. FIGS. 59-62 show the distal end 284 of a delivery device 286 that has 8 delivery sheaths 288 that deploy 8 surgical coils 290 simultaneously to suture an artificial heart valve 292 to the annulus of the atrium 294. The method of use may follow the sequence of the figures, wherein, in FIG. 60 the delivery device 286 is positioned with the delivery sheaths 288 disposed within tissue 294 adjacent the heart valve 292. In FIG. 61, the surgical coils 290 are being deployed from the distal ports (not shown) of the 8 delivery sheaths 288. In FIG. 62, the delivery device has been proximally retracted, and the heart valve 292 secured to the heart tissue 294 by the surgical coils 290.

FIGS. 63-68 show another embodiment of a delivery device 296 and method where the distal end 298 of the delivery device 296 can deploy two surgical coils 300 simultaneously from opposing sides of a tissue cut 302 and can be used as a stapling or suturing device for the closure of tissue incisions or cuts. The method of use can follow the sequence of FIGS. 65-68. FIG. 63 shows a distal portion 304 of a deployment shaft assembly 306 wherein the distal ends of a first delivery sheath 312 and a second delivery sheath 314 are disposed within and radially constrained by an outer sheath 316. FIG. 64 shows the deployment shaft assembly 306 with the outer sheath 316 proximally retracted and the distal ends 308 and 310 of the delivery sheaths 312 and 314 in a radially expanded and relaxed state.

Figure 67:
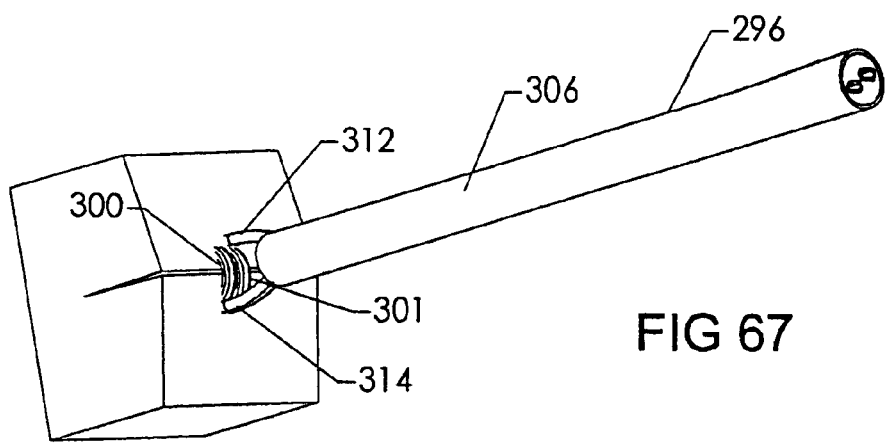
FIG. 67 shows the delivery device of FIG. 66 with 2 surgical coils fully deployed from the distal ends of the delivery sheaths into the tissue across the incision.
Figure 68:
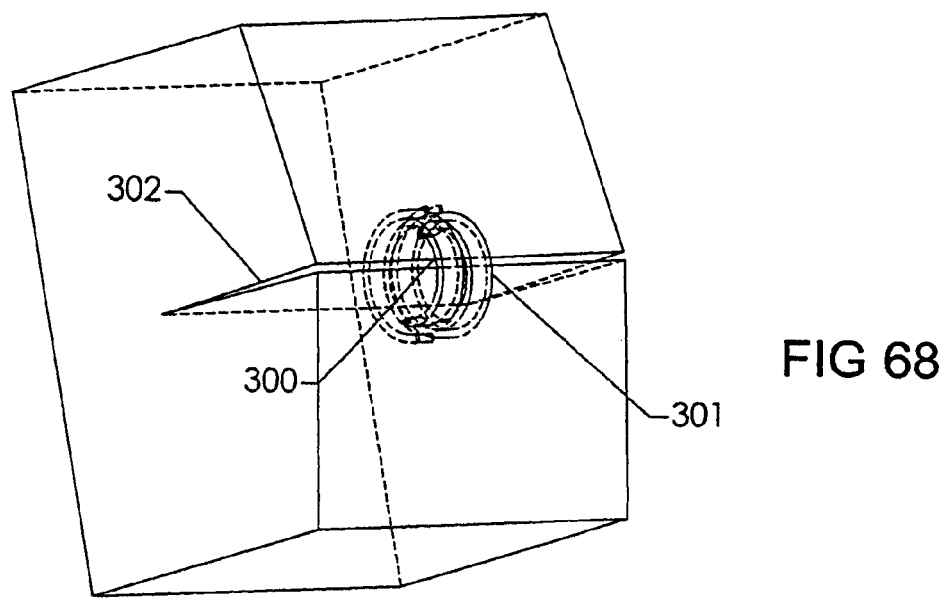
FIG. 68 shows the two deployed surgical coils of FIG. 67 across the incision of the tissue with the delivery device removed.

The deployment shaft assembly 306 is then advanced towards target tissue, such as tissue which has a cut therein. The sharpened distal tips 308 and 310 of the first and second delivery sheaths 312 and 314 are then forced into tissue on opposite sides of the cut and the outer sheath 316 then advanced distally. This motion of the outer sheath 316 reasserts the radial constraint on the distal ends 308 and 310 of the delivery sheaths 312 and 314 and pulls both the distal ends 308 and 310 of the delivery sheaths 312 and 314 and the tissue on opposite sides of the cut closer together as shown in FIG. 66. A first surgical coil 300 and a second surgical coil 301 are then deployed from first and second distal ports 318 and 320 of the delivery sheaths 312 and 314 into the tissue as shown in FIG. 67, with the cut in the tissue being permanently closed at the end of the procedure as shown in FIG. 68. The delivery device 296 has a low profile that facilitates placement through an endoscope, cannula or a confined space. A portion of the coils 300 and 301 are shown exposed on the external surface of the tissue, however, the coils 300 and 301 can be placed deeper and remain completely implanted in the tissue.

FIGS. 69-75 show another embodiment of a delivery device where a distal end of the delivery device can deploy a radial pattern of surgical coils that are not on a specific or fixed radius. The delivery device 322 is a low profile catheter that can be readily passed through a natural body track or channel, e.g., artery, vein, GI tract, urethra etc. A distal portion 324 of the delivery device 322 is configured to be expanded as necessary for a given indication. An expansion member 326, such as an expandable balloon can be used to expand a distal portion of the delivery sheaths 328 of the delivery device 322. A balloon expansion method is shown which allows the delivery device to accommodate anatomical and device size variations.

FIGS. 69-75 show how the delivery device 322 may be used to attach the leg of a stent or stent-graft 330 that may be used to treat an abdominal aortic aneurysm (AAA). The method of use may follow the sequence of the figures. This delivery device 322 is not, however, limited to the AAA application only. For example, the delivery device 322 could also be used to attach vascular grafts to artery walls or place a radial pattern of coils in the GI tract of a patient that could subsequently be used to make a purse string suture prior to cutting away a portion of the patient's colon.

In FIG. 70, the delivery device 322 is shown being advanced into a AAA stent 330 over a guidewire 332. The balloon at the distal end 334 of the delivery device 322, which is disposed within the circumferential configuration of delivery sheaths 328, is then expanded which forces the distal ends of the delivery sheaths 328 against an inside surface 336 of the AAA stent 330 as shown in FIGS. 71, 72 and 73. The AAA stent can be positioned within a patient's artery or other vessel either before or after the balloon 326 is expanded. Once positioned, surgical coils 338 are deployed from distal ports 340 of the delivery sheaths 328 as shown in FIG. 74 and the surgical coils 338 then penetrate the material of the AAA stent 330 and the adjacent tissue of the body vessel 342 as shown in FIG. 75. The surgical coils 338 deployed may penetrate the wall of the vessel 342 completely, or may be embedded in the wall of the vessel 342 and not break an outside surface 343 of the vessel 342.

Figure 76:
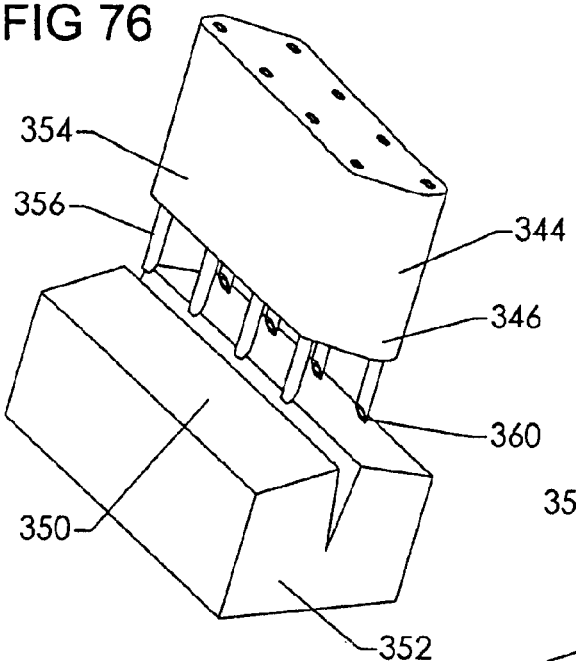
FIG. 76 is a diagrammatic view in perspective of a distal portion of a delivery device configured to deploy 8 surgical coils simultaneoulsly along and across an open incision or cut in tissue adjacent a tissue portion having an open cut.
Figure 77:
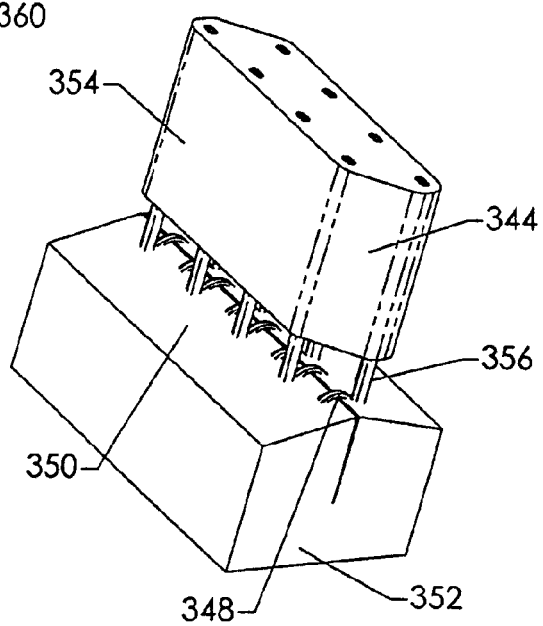
FIG. 77 shows the delivery device of FIG. 76 with distal ends of delivery cannulae of the delivery device engaging and penetrating tissue adjacent the open cut with surgical coils being deployed while pressure is being applied to the tissue to close the cut.
Figure 78:
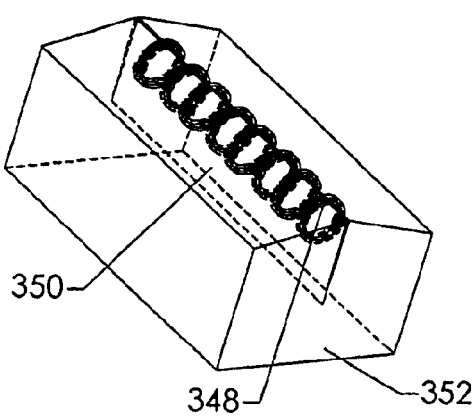
FIG. 78 shows the 8 surgical coils of FIG. 77 deployed in the tissue across the cut securing the cut in a closed configuration.

FIGS. 76-78 show another embodiment of a delivery device 344 where a distal end of delivery device 344 can deploy a linear pattern of surgical coils 348 simultaneously from opposing directions and may be used as a stapling or suturing device for the closure of tissue incisions or cuts. The method of use for the delivery device 344 may follow the sequence of the FIGS. 76-78. The delivery device 344 could be used for rapid closure of cuts or wounds. FIGS. 76-78 show a portion of the surgical coils 348 exposed on an external surface 350 of the tissue, however, the surgical coils 348 can also be placed deeper in the tissue 352 and remain completely implanted beneath a surface of the tissue 352. In FIG. 76 a delivery sheath housing 354 securing 8 delivery sheaths 356 in fixed relation is disposed adjacent a portion of tissue 352 having a cut in the surface thereof. FIG. 77 shows the sharpened distal tips 358 of the delivery sheaths 356 penetrating the tissue 352 with the surgical coils 348 being deployed from distal ports 360 of the delivery sheaths 356. FIG. 78 shows the cut in the tissue 352 secured in a closed position by the 8 surgical coils 348. Note that the configuration of the delivery sheath housing 354 could include an arrangement similar to that of FIG. 63 with an outer sheath 316 that could be activated to squeeze the cut of the tissue 352 closed by advancing same over radially expanded distal portions of the delivery sheaths 356. One alternative of this method is to use manual closure of the wound or cut 352 during deployment of the surgical coils 348.

Embodiments of devices and methods are also contemplated for attaching items to surgical coils in conjunction with a the coil deployment process. Some of the items that can be attached to a surgical coil 10 during deployment include, but are not limited to, suture lines, anchor lines, electrical leads & catheters. These attachments can be attached at the surface of tissue or implanted in tissue at any depth when the coils are placed or deployed as shown in FIG. 45.

FIGS. 79-91 show devices for and methods of making an attachment to a variety of tissue types by use of a surgical coil as an anchor member. The delivery device 362 shown in FIGS. 79-109 can have features similar or identical to features of the delivery device 138 shown in FIGS. 25-41C. The delivery device 362 shown in FIG. 79 has a deployment shaft assembly 364, a delivery actuator housing 366, a delivery sheath actuator 368 slidingly engaged with the delivery actuator housing 366 and a cylindrical actuator 370 slidingly engaged with the delivery sheath actuator 368. Such a delivery device 362 may be used for deployment of a surgical coil attachment 372, where the attachment 372 (for example, a length of flexible suture) may be enclosed within alignment tubes 374 disposed within an outer sheath 376 of the deployment shaft assembly 364. The suture 372 can be fed through a side port 378 of the delivery actuator housing 364 of the delivery device 362 as shown in FIG. 80. The side port 378 feeds into a deployment shaft assembly 364 where it may be placed alongside a surgical coil delivery sheath 380 within an outer sheath 376 of a deployment shaft assembly 364.

FIG. 82 illustrates a stop 382 which is used to control a distal position of distal ends 384 of the alignment tubes 374, which in turn determines the distal position of an attachment loop 386 of the suture 372, relative to a distal port 388 of the surgical coil delivery sheath 380 (see FIG. 83). A distal portion of the alignment tubes 374 may have a pre-bend or other bias towards an outward radial direction and upward direction that is constrained by an inside surface 390 of the outer sheath 376. The bias of the alignment tubes may be configured to position the attachment loop 386 at or near the center of a surgical coil being deployed from the delivery sheath. The deployment shaft assembly 364 may be advanced to a target site while the components at a distal end of the deployment shaft assembly 364 of the delivery device 362 are positioned as shown in FIG. 83. The target site may be accessed by a variety of methods, such as those shown in FIG. 45, as well as others. A sharpened distal tip 394 of the outer sheath 376 of the deployment shaft assembly 364 may be used to penetrate soft tissue in order to access the target site.

When the target site has been accessed, the outer sheath 376 is moved proximally as shown in FIG. 85 and the distal ends 384 of the alignment tubes 374 are then exposed and released from a constrained state. An incision that the outer sheath 376 made prior to being moved proximally allows the alignment tubes 374 to spread as shown in FIG. 86. An elongate element 396 of a surgical coil 398 is then deployed from a distal port 388 of the delivery sheath 380 and captures the attachment loop 386 of the suture as shown in FIG. 88. The delivery device 362 can then be removed, and in doing so, the suture is allowed to pull out of the alignment tubes and is left attached to the surgical coil 398 as shown in FIG. 89. This method provides a means to place and anchor suture lines 372 in tissue at difficult to access or confined places at any desired depth.

Figure 90:
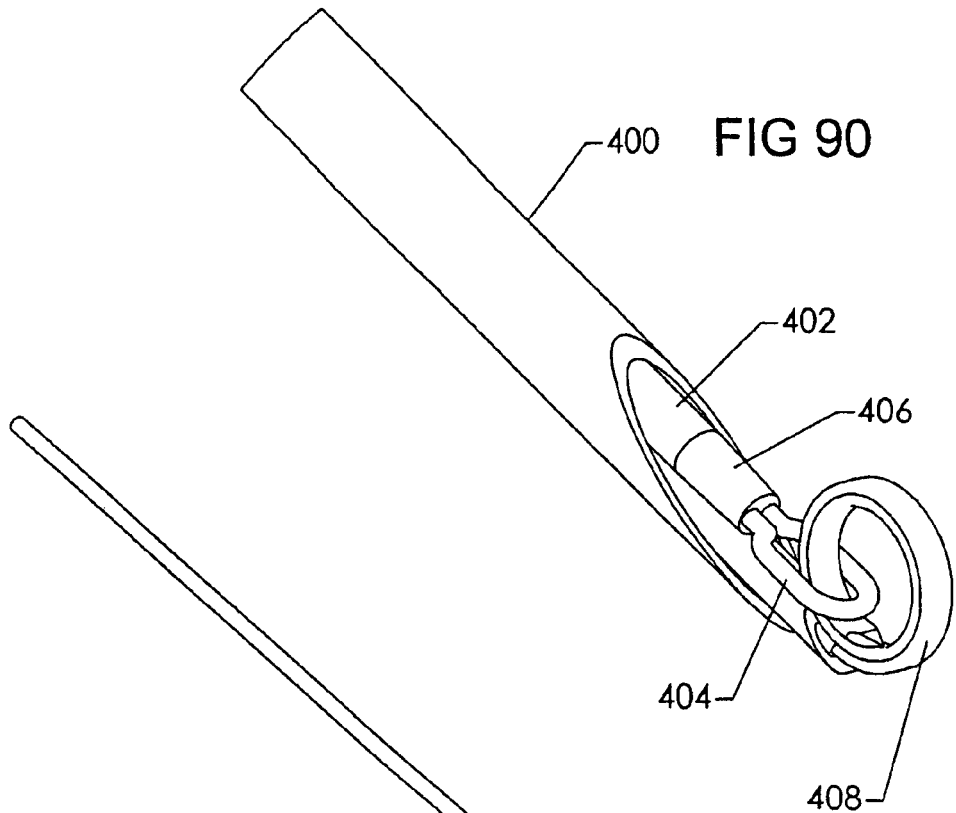
FIG. 90 is an enlarged view in perspective of a distal portion of an alternative embodiment of a delivery device similar to the delivery device of FIG. 79 but wherein the suture alignment tubes and suture are replaced by a single leg attachment line having a fixed loop disposed adjacent a distal end of the delivery sheath with a surgical coil being deployed through the fixed loop.
Figure 91:
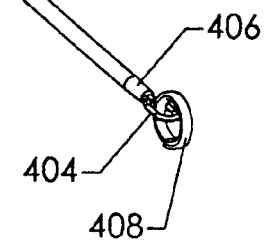
FIG. 91 is a perspective view of the surgical coil and single leg attachment line of FIG. 90 with the surgical coil deployed in tissue (not shown) through the fixed loop of the single leg attachment line.
Figure 92:
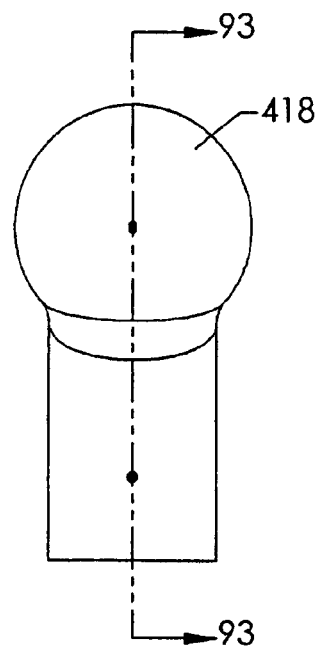
FIG. 92 is an elevational view of a portion of bone tissue of a patient.

FIGS. 90 and 91 show another embodiment of a delivery device 400 where a single leg attachment line 402 with a fixed attachment loop 404 at a distal end 406 thereof, is attached by a similar method but without the need for the alignment tubes 374 of the delivery device 362 shown in FIGS. 79-89 above. The attachment loop 404 may be made of a stiff material (e.g. metals, such as stainless steel or high strength polymers or composites) which ensures that an opening is provided for a surgical coil 408 to pass through during deployment of the surgical coil 408 and thereby be captured. When the delivery device 400 is proximally retracted or removed, the attachment line 402 is allowed to pull through the outer sheath 410 and remain attached to the surgical coil 408. A proximal portion 412 of the attachment 402 can be made of a variety of materials and have a variety of configurations e.g. stainless steel, flexible or stiff plastic, suture material, single or multi filament stand, and the like.

Referring to FIGS. 92-95, a surgical coil anchor 414 can be used in applications such as anchoring ligaments or tendons, when performing soft tissue surgical reconstruction, ruptured tendons, or torn ligaments, and other indications in which a surgeon wants to reconstruct or repair connective tissue with respect to the bone tissue. In one embodiment, a surgical coil anchor 414 is placed through a pre-drilled pilot hole 416 disposed in bone tissue 418 of a patient, having a diameter much smaller than an outer diameter of the surgical coil anchor 414 as shown in FIGS. 92-95. The deployment shaft assembly 364 of the delivery device 362 is subsequently introduced into the pilot hole 416 and the surgical coil anchor 414 is deployed therein along with a suitable attachment member 372 into the bone 418. A ligament or tendon may then be sutured and anchored to the bone tissue 418 using the anchor attachment 414. The anchor attachment 414 can be a piece of suture, wire or the like.

Figure 93:
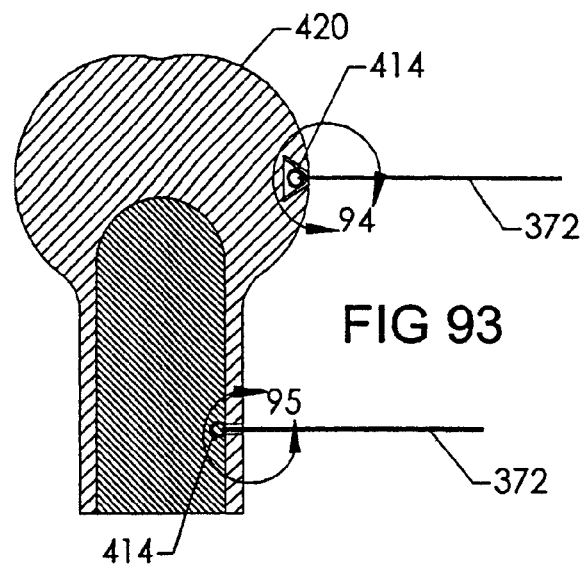
FIG. 93 is a transverse cross sectional view of the bone tissue of FIG. 92 taken along lines 93-93 of FIG. 92 illustrating first and second surgical coils deployed at two different sites on the bone tissue portion with attachment members extending from the bone tissue.

A bone-drilling device (not shown) can be used that permits the drill to adjust its approach angle while maintaining the same entry point at the bone surface 420. Multiple passes of the drill can be made into the bone at the same entry point 418 at varying angles to produce a small round profile hole 416 at the surface 420 of the bone 418 tapering to an incrementally larger oval profile hole or cavity 422 beneath the surface 420 of the bone tissue 418 as seen in FIG. 93. The round entry hole 416 is made large enough to accept a distal end 392 of a delivery device 362 while part of the oval profile cavity 422 beneath the surface 420 of the bone tissue 418 is made large enough to accommodate a surgical coil anchor 414.

Figure 94:
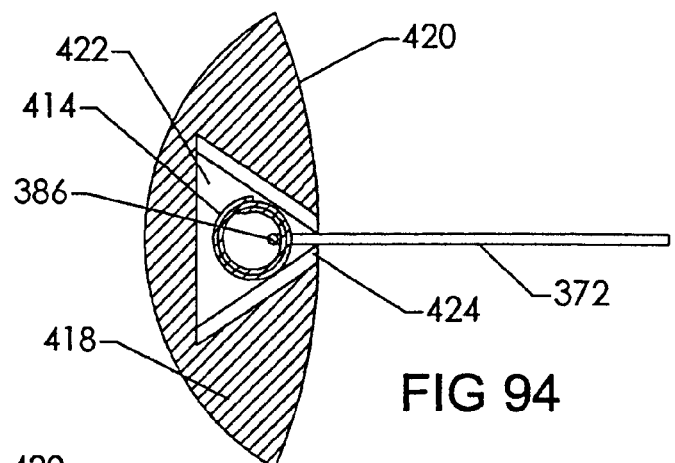
FIG. 94 is an enlarged view of encircled portion 94 of FIG. 93 illustrating the first surgical coil deployed within a cavity of the bone tissue.
Figure 95:
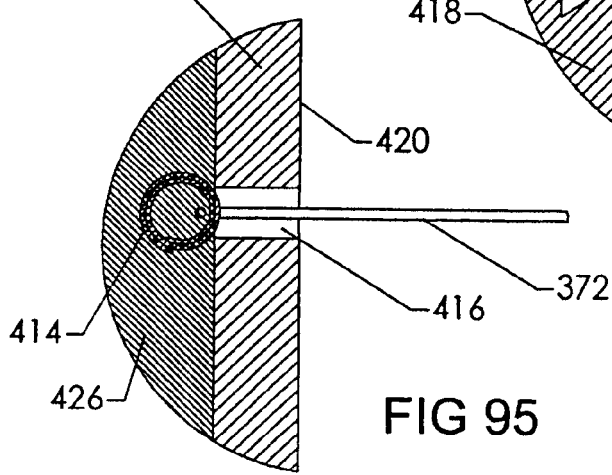
FIG. 95 is an enlarged view of encircled portion 95 of FIG. 93 illustrating the second surgical coil deployed within a cavity of the bone tissue.
Figure 94A:
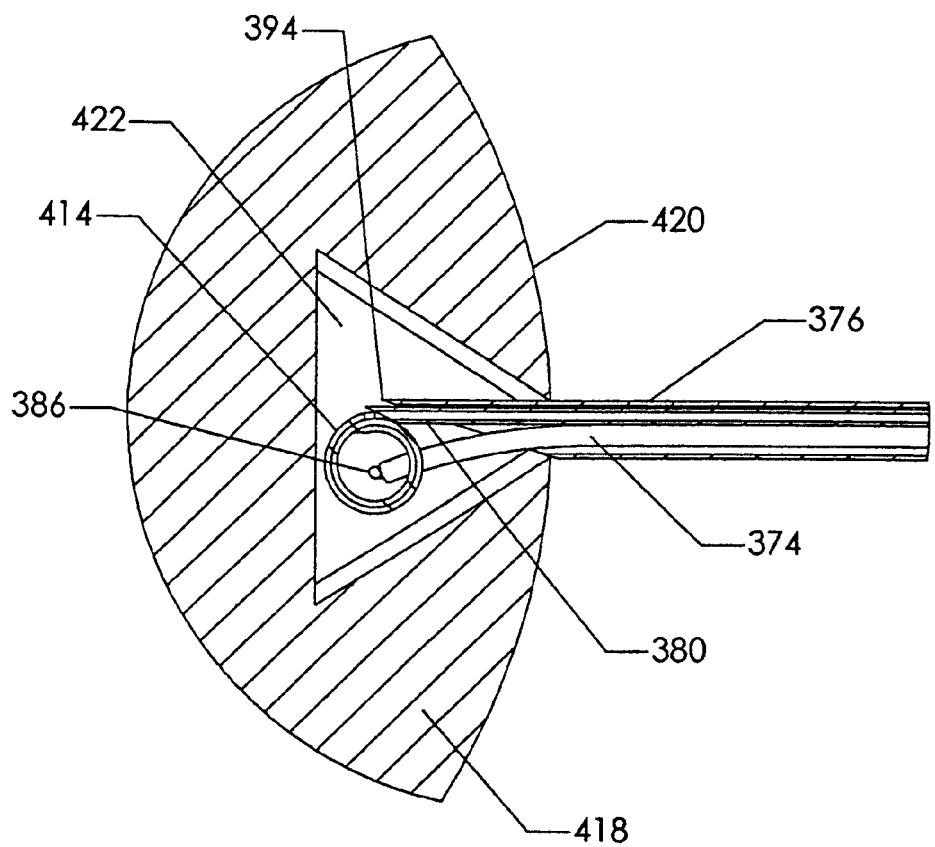
FIG. 94A is an enlarged view of a delivery device deploying a surgical coil about a suture attachment member within a cavity of bone tissue.
Figure 96:
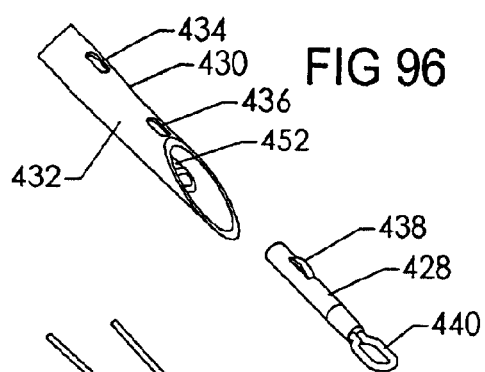
FIG. 96 is a perspective view of a distal portion of a deployment shaft assembly of a delivery device with an attachment member separated distally from the deployment shaft assembly.
Figure 97:
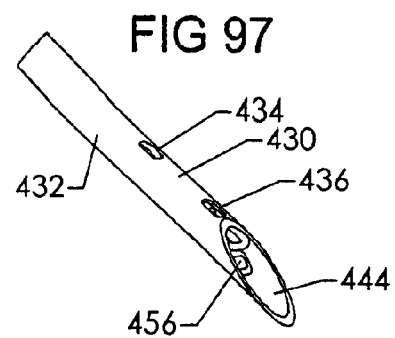
FIG. 97 is a perspective view of the distal portion of the delivery shaft assembly of FIG. 96 with a retainer spring of the attachment member engaged within a proximal slot of the outer sheath.
Figure 98:
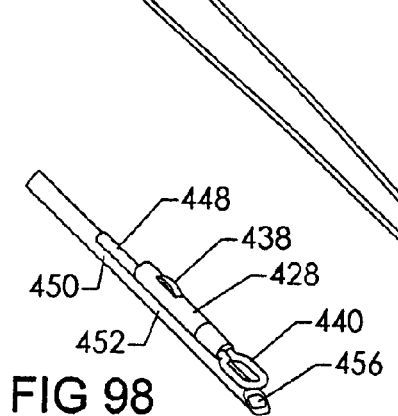
FIG. 98 is a perspective view of the distal portion of the delivery delivery shaft assembly of FIG. 97 (with the outer sheath not shown) illustrating a proximal stop secured to the delivery sheath.

Alternatively a straight pilot hole 424 can be drilled through a thin section of bone tissue 418 and into the bone marrow 426 as shown in FIG. 94. Thereafter, the delivery device 362 can be introduced through the pilot hole 424 into the marrow 426 and the surgical coil anchor 414 deployed along with an attachment member 372 into the bone marrow 426.

Yet another embodiment of a delivery device installs an attachment member from a distal end of the delivery device as shown in FIGS. 96-101. This method allows shorter attachment members 428 to be used, which can optionally be dispensed from a cassette for sterility and convenience if required. The delivery device 362 used for the deployment shaft assembly 430 shown in FIGS. 96-101 can be the same or similar to the delivery device 362 discussed above and shown in FIGS. 79-91. An outer sheath 432 of the deployment shaft assembly 430 has a proximal slot 434 and a distal slot 436 which are configured to engage a retainer spring 438 of the attachment member 428. The attachment member 428 is relatively short in axial length and has an attachment loop 440 at the distal end.

Figure 99:
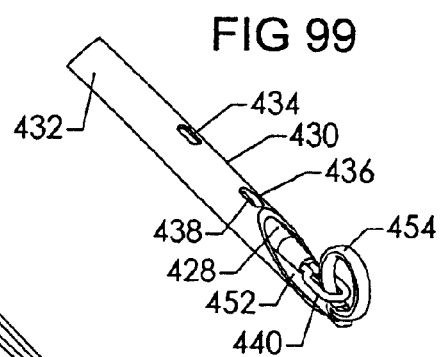
FIG. 99 is perspective view of the distal portion of the deployment shaft assembly of FIG. 97 with the retainer spring engaged in a distal slot of the outer sheath and with a surgical coil being deployed from a distal end of the delivery sheath through a distal loop of the attachment member.
Figure 100:
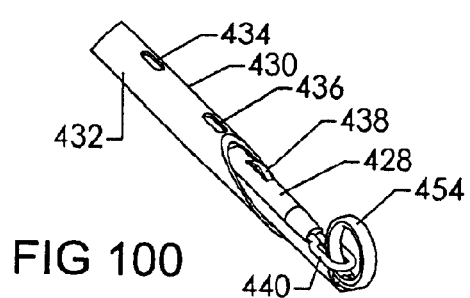
FIG. 100 illustrates a distal portion of the deployment shaft assembly of FIG. 99 with the assembly retracted proximally from the attachment member such that the retainer spring is no longer engaged with the distal slot.
Figure 101:
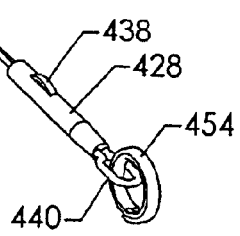
FIG. 101 shows the surgical coil deployed about target tissue (not shown) and deployed about and encircling a distal loop of the attachment member.

The attachment member 442 is loaded into a distal port 444 of the outer sheath 432 until a proximal end of the attachment member 442 rests against a stop 448 which is fixed to an outside surface 450 of a delivery sheath 452 disposed within the outer sheath 432 at which point the retainer spring 438 also engages the proximal slot 434 in the outer sheath 432. The deployment shaft assembly 430 is then advanced to a target site, and the outer sheath 432 retracted relative to the attachment member 428 and delivery sheath 452 until the retainer spring 438 on the attachment member 428 engages the distal slot 436 of the outer sheath 432 as shown in FIG. 99. A surgical coil 454 is then deployed from a distal port 456 of the delivery sheath 452 through the attachment loop 440 of the attachment member 428 as shown in FIG. 99. The deployment shaft assembly 430 is thereafter retracted proximally leaving the attachment member 428 secured to the tissue at the target site or captured by bone tissue 418 if deployed in a cavity 422 formed in bone tissue 418, or the like as shown in FIGS. 100 and 101.

Referring to FIGS. 102-109, another embodiment of a delivery device 458 uses an attachment member 460 that can be joined to multiple surgical coils 462 simultaneously. The delivery device 458 can be used to anchor an attachment member 460 to a target tissue site and allow a surgeon to locate and excise a pathologically suspect tissue mass or other tissue of interest. The attachment member has three resilient attachment loops 459 disposed adjacent distal ports of three respective delivery sheaths 461. When the attachment loops 459 are constrained within an outer sheath 463, they assume a constrained first outer diameter as illustrated in FIG. 106. When released from the constraint of the outer sheath 463, as shown in FIG. 107, the attachment loops then assume a relaxed state having a greater outer diameter, greater than an outer diameter of the outer sheath 463 in some embodiments. The attachment loops are then positioned at or near the center of surgical coils 462 which can then be deployed from the delivery sheaths 461 as shown in FIGS. 105 and 107. Once deployed, the surgical coils 462 will not migrate from the target site. This can be important for certain indications, specifically in breast biopsy procedures where the breast may be compressed during placement of the surgical coils 462. This, movement of the surgical coils 462 is prevented when compression is released from at the breast at the completion of the imaging procedure, or if the attachment leg 464 is inadvertently shifted after the procedure. The attachment leg 464 that extends out of the patient's body can be flexible, making it more tolerable for a patient awaiting surgery.

FIGS. 110-125 show an embodiment of a deflecting delivery device 466. The delivery device 466 may have features that are the same as or similar to those of the delivery devices 138 and 362 discussed above. The method of deployment may follow the sequence in FIGS. 114-121. The delivery device 466 is similar to the low profile single coil needle delivery devices 138 and 362 shown in FIGS. 25 and 46 with the addition of a surgical coil delivery sheath 468 having a preformed curve 470 at a distal end 472 thereof as shown in FIG. 115. The coil delivery sheath 468 can be made from materials that exhibit either great elasticity or shape memory properties. Suitable materials for fabrication of the coil delivery tube include, but are not limited to, nickel titanium alloys (Nitinol), stainless steel, elgiloy, and MP35N.

The delivery device 466 also has an additional outer sheath 474 that has a close sliding fit with the delivery sheath 468. This outer sheath 474 can be moved relative to the delivery sheath 468 by repositioning the finger grip 476 shown in FIGS. 110-113. When the finger grip 476 is in the proximal position the deflecting delivery sheath 468 will be completely covered and straightened by the outer sheath 474. In this position the device 466 can be used in the same manner as the low profile single coil delivery devices 138 and 240. When the finger grip 476 is moved distally, however, the delivery sheath 468 exits a distal end of the outer sheath 474 and is allowed to assume its natural relaxed shape or configuration as shown in FIG. 115. Subsequently, the shape of the delivery sheath 468 will redirect the placement of any surgical coils 478 ejected or deployed relative to the centerline axis of the delivery device 466.

One clinical application that would benefit from this embodiment of the delivery device 466 is the marking of biopsy sites and tissue masses. One method of clinical use is illustrated in FIGS. 122 and 123. A mammatome 480 is a device frequently used to biopsy breast abnormalities. Part of the procedure often entails placing one or more markers 478 in wall of a biopsy cavity 482. Previously used designs of these markers 478 frequently are dislodged from the placement site by the cut out or lateral aperture 484 of the mammatome device 480. In order to prevent this, the deflecting delivery device 466 may place the markers 478 in the tissue 486 around the target tissue 482 of the biopsy site not within the target tissue. Thus, the marker or markers 478 will not be dislodged during the biopsy procedure. This method provides assurance that the marker or markers 478 remain fixed after deployment.

Another method of deploying markers 478 is shown in FIGS. 124 and 125 where a delivery device 466 is placed in a pathologically suspect tissue mass 488. It is often desirable to be able to accurately mark the location prior to surgery to ensure that the suspect mass 488 is totally excised. It has become common practice when dealing with breast cancer to remove not only the suspect mass 488 but also a 1 cm margin surrounding the suspect mass 488. FIGS. 124 and 125 show the deflecting delivery device 466 being used to place surgical coils 478 at this margin boundary 490. Using a single insertion entry site for the delivery device 466, multiple surgical coils 478 can be deployed within a lesion or target tissue 488. The delivery device 466 can be used with the delivery sheath 468 undeflected to mark the anterior and posterior boundary 490, by simply keeping the outer sheath 474 in a distal position as shown in FIG. 113.

The deflecting delivery sheath 468 can then be advanced and a surgical coil 478 placed at both boundaries as shown in FIGS. 124 and 125. The deflection of the delivery sheath 468 is correctly sized in this embodiment to ensure that the surgical coil 478 is position 1 cm off the centerline 500 as shown in FIG. 125. After deployment of a surgical coil 478, the delivery sheath 468 is retracted, the delivery device 466 is rotated, once again the delivery sheath 468 is advanced and another surgical coil 478 deployed at a new location. This process is repeated as many times as is necessary to correctly identify the perimeter 490 of the suspect target tissue mass 488. The maximum deflection angle shown in FIGS. 110-125 is approximately 90 degrees, however, the amount of deflection can be increased or decreased for this or other embodiments.

Referring to FIGS. 126-135, an embodiment of a method and tools for manufacturing surgical coils are illustrated. FIGS. 126-130 illustrate a shape forming jig 502 for shape setting a piece of ribbon material 504, such as metallic Nitinol ribbon material, into a coil configuration. The jig 502 has a cylindrical cavity 506 with an inside diameter that defines an outside diameter of a coil produced by the jig 502. An access slot 508 communicates from the cylindrical cavity 506 to an outer wall 510 of the jig body 502. Both the cylindrical cavity 506 and the access slot 508 are open at a top surface 512 of the jig 502 to facilitate removal of the heat set ribbon 504, as shown in FIG. 130. A post member 514 is positioned in the center of the cylindrical cavity 506 which is cylindrically shaped and together with the cylindrical cavity 506 of the jig 502 body forms a circular slot 516 in communication with the access slot 508.

The access slot 508 meets the circular slot 516 in a tangential orientation which allows a piece of metallic ribbon 504 to be inserted from outside the jig 502, through the access slot 508 and into the circular slot 516 as shown in FIG. 128. As the ribbon material enters the circular slot 504, it begins to follow the curvature of the cylindrical cavity 506 and is bounded radially by an inside surface 518 of the cylindrical cavity 506 and an outside surface 520 of the post member 514. The metallic ribbon 504 is forced into the circular slot 516 until a desired amount of circumferential overlap is formed in the coil configuration of the ribbon material 504. The entire jig 502 and metallic ribbon 504 may then be placed within a heat source so as to heat treat the Nitinol ribbon material 504 to take a set in the coiled configuration and assume the desired mechanical properties for a surgical coil 522.

In some embodiments of surgical coils 522, it is desired that the material of the surgical coil have superelastic properties. Heat treatment parameters that can be used include subjecting the coiled ribbon material 504 in the jig 502 to a temperature of about 400 to about 500 degrees C. for several minutes. More specifically, subjecting the ribbon material 504 to a temperature of about 480 to about 500 degrees C. for about 1 to about 5 minutes. One embodiment of an alloy that can be used for this process includes a Nitinol alloy having about 55.7 to about 55.9 composition by weight nickel, with the remainder or balance being tin. Another Nitinol alloy that is suitable includes an alloy having about 55.5 to about 55.7 composition by weight nickel, with the balance being tin. Such compositions may undergo cold working processes prior to the heat treatment discussed above.

Once the metallic ribbon material 504 has been heat treated and removed from the jig 502, it can then be inserted into a constraint slot 524 of a punch 526 and die 528 as shown in FIGS. 131-135, which is configured to cut the shape-formed ribbon 504, or elongate element 530 to length and produce a proximal end and distal end having a desired configuration. FIG. 131 illustrates the metal punch member 526 and a metal die member 528 which can be manufactured from any appropriate material, such as tool steel or the like. The punch member 526 has a first punch element 536 and a second punch element 538. The first punch element 536 is configured to cut the ribbon material 504 into a sharp wedge tipped configuration in order to form the sharp pointed, tissue penetrating wedge shaped distal tip 540 of an elongate element 530 as discussed above and shown in FIG. 136. The second punch element 538 is configured to cut a wedge shaped "V" in the ribbon material 504 in order to produce the wedge shaped proximal end 542 of an elongate element 530, also as discussed above.

Once the punch 526 and die 528 has been activated and the proximal and distal ends 532 and 534 respectively of a shape formed elongate element 530 are formed, the elongate element 530 can then be forced from the constraint slot 524 of the punch 526 and die 528 with another piece of ribbon 504 or the like. It may be desirable to load the newly formed elongate element 530 of a surgical coil directly into another constraining device configured for storage or sterilization of the elongate element 530.

The apparatus and methods of the present invention may be embodied in other specific forms without departing from its spirit or essential characteristics. Embodiments can be combined to create other embodiments for example combining the deflecting delivery system embodiment with the attachment embodiment to create a defecting attachment coil delivery device. The described embodiments are to be considered in all respects only as illustrative and not restrictive. Accordingly, it is not intended that the invention be limited, except as by the appended claims.

What is claimed is:

1. A method for deploying a surgical coil and attachment member in a patient's body, comprising:
    positioning a distal end of a deployment shaft assembly adjacent a deployment site;
    axially advancing the surgical coil through a delivery sheath of the deployment shaft assembly, out of a distal port of the delivery sheath, into target tissue and around an attachment loop of the attachment member while at least a portion of the attachment member is disposed within an outer sheath of the deployment shaft assembly; and
    continuing to advance the surgical coil into the target tissue allowing an elongate element of the surgical coil to self-form into an enclosed configuration with the elongate element making contact with itself in an overlapped portion and with an element axis of the elongate element on each side of a section of the surgical coil forming an angle of about 90 degrees with respect to a coil axis of the surgical coil and continuing to advance the surgical coil until the overlapped portion has a circumferential overlap of at least about 360 degrees.

2. The method of claim 1 wherein the elongate element is advanced from the delivery sheath until a proximal end of the elongate element is ejected from the delivery sheath and the surgical coil is fully deployed in the target tissue, disconnected from the delivery sheath and encircles the attachment loop of the attachment member.

3. The method of claim 1 wherein the delivery sheath constrains the elongate element to a substantially straight configuration prior to ejection from the distal end of the delivery sheath.

4. The method of claim 1 further comprising proximally withdrawing the deployment shaft assembly leaving the surgical coil in place secured to the attachment loop.

5. The method of claim 1 wherein the deployment shaft assembly further comprises two suture alignment tubes extending within the outer sheath of the deployment shaft assembly and having distal end ports disposed adjacent the distal port of the delivery sheath, wherein the attachment loop comprises a length of suture material extending between distal ports of the suture alignment tubes, and wherein axially advancing the surgical coil comprises axially advancing the surgical coil around the length of suture material.

6. The method of claim 5 wherein the distal ends of the suture alignment tubes have an outward radial bias that can be constrained by the outer sheath when the outer sheath is disposed about said distal ends and further comprising proximally withdrawing the outer sheath and expanding distal ends of the suture alignment tubes in an outward radial orientation prior to deploying the surgical coil from the distal port of the delivery sheath.

7. The method of claim 1 wherein the deployment shaft assembly comprises a plurality of delivery sheaths and a plurality of surgical coils are deployed around a plurality of attachment loops.

8. The method of claim 1 further comprising pre-forming a cavity in the target tissue prior to positioning the distal end of the deployment shaft assembly adjacent a deployment site in the cavity and further comprising deploying the surgical coil within the cavity such that the surgical coil is trapped in the cavity and the attachment member extends from the cavity.

9. The method of claim 8 wherein the cavity is formed in bone tissue and the surgical coil is deployed within and trapped by bone tissue.

10. The method of claim 8 wherein the cavity is formed in bone and bone marrow tissue and the surgical coil is deployed at least partially within the bone marrow tissue.

11. The method of claim 1 wherein the elongate element of the surgical coil includes a minor transverse dimension and a major transverse dimension in cross section and wherein continuing to advance the surgical coil into the target tissue and allowing the elongate element of the surgical coil to self-form into an enclosed configuration with the elongate element making contact with itself in the overlapped portion comprises allowing the elongate element to make contact with itself along the major transverse dimension of the elongate element in the overlapped portion.

* * * * *